(12) United States Patent
Shikanai et al.

(10) Patent No.: US 10,988,468 B2
(45) Date of Patent: Apr. 27, 2021

(54) NITROGEN-CONTAINING 6-MEMBERED CYCLIC COMPOUND

(71) Applicant: Asahi Kasei Pharma Corporation, Tokyo (JP)

(72) Inventors: Daisuke Shikanai, Tokyo (JP); Noriko Ishiguro, Tokyo (JP)

(73) Assignee: ASAHI KASEI PHARMA CORPORATION, Tokyo (JP)

(*) Notice: Subject to any disclaimer, the term of this patent is extended or adjusted under 35 U.S.C. 154(b) by 0 days.

(21) Appl. No.: 16/333,510

(22) PCT Filed: Dec. 25, 2018

(86) PCT No.: PCT/JP2018/047450
§ 371 (c)(1),
(2) Date: Mar. 14, 2019

(87) PCT Pub. No.: WO2019/131582
PCT Pub. Date: Jul. 4, 2019

(65) Prior Publication Data
US 2020/0347046 A1   Nov. 5, 2020

(30) Foreign Application Priority Data
Dec. 25, 2017   (JP) .................... JP2017-248173

(51) Int. Cl.
C07D 417/14    (2006.01)
A61P 41/00     (2006.01)
A61P 19/00     (2006.01)

(52) U.S. Cl.
CPC .......... *C07D 417/14* (2013.01); *A61P 19/00* (2018.01); *A61P 41/00* (2018.01)

(58) Field of Classification Search
CPC .................................................. C07D 417/14
USPC .................................................. 514/222.5
See application file for complete search history.

(56) References Cited

U.S. PATENT DOCUMENTS

| | | |
|---|---|---|
| 6,747,037 B1 | 6/2004 | Old et al. |
| 2005/0020686 A1 | 1/2005 | Maruyama et al. |
| 2007/0060590 A1 | 3/2007 | Shoda et al. |
| 2007/0129327 A1 | 6/2007 | Ohmoto et al. |
| 2008/0021021 A1 | 1/2008 | Okada et al. |
| 2009/0227644 A1 | 9/2009 | Ohmoto et al. |
| 2010/0010222 A1 | 1/2010 | Maruyama et al. |
| 2011/0015238 A1 | 1/2011 | Ohmoto et al. |
| 2011/0059920 A1 | 3/2011 | Ohmoto et al. |
| 2012/0202773 A1 | 8/2012 | Maruyama et al. |
| 2013/0143934 A1 | 6/2013 | Ohmoto et al. |
| 2016/0060216 A1 | 3/2016 | Barrett et al. |

FOREIGN PATENT DOCUMENTS

| | | |
|---|---|---|
| EP | 1847533 A1 | 10/2007 |
| JP | 2016-516050 A | 6/2016 |
| WO | WO 02/24647 A1 | 3/2002 |
| WO | WO 02/42268 A2 | 5/2002 |
| WO | WO 03/007941 A1 | 1/2003 |
| WO | WO 03/009872 A1 | 2/2003 |
| WO | WO 03/035064 A1 | 5/2003 |
| WO | WO 2004/063158 A1 | 7/2004 |
| WO | WO 2004/085430 A1 | 10/2004 |
| WO | WO 2005/053707 A1 | 6/2005 |
| WO | WO 2006/016689 A1 | 2/2006 |
| WO | WO 2006/080323 A1 | 8/2006 |
| WO | WO 2006/129788 A1 | 12/2006 |

OTHER PUBLICATIONS

Cooper et al., "Population-Based Study of Survival After Osteoporotic Fractures", Am. J. Epidemiol., vol. 137, No. 9, 1993, pp. 1001-1005.
International Search Report and Written Opinion of the International Searching Authority for International Application No. PCT/JP2018/047450, dated Mar. 19, 2019.
Zhao et al., "Synthesis and Evaluation of Novel Pyrazolidinone Analogs of PGE$_2$ as EP$_2$ and EP$_4$ Receptors Agonists", Bioorganic & Medicinal Chemistry Letters, vol. 17, Available Sep. 26, 2007, pp. 6572-6575.
Indian Office Action, dated Dec. 31, 2020, for Indian Application No. 202017025430, with an English translation.

*Primary Examiner* — Kahsay Habte
(74) *Attorney, Agent, or Firm* — Birch, Stewart, Kolasch & Birch, LLP

(57) ABSTRACT

A novel compound represented by the following general formula (1), or a salt thereof, which has a superior EP$_4$ receptor agonist activity, and a medicament containing the compound or a salt thereof as an active ingredient, which can be used for promotion of osteogenesis, therapeutic treatment and/or promotion of healing of fracture and the like.

(1)

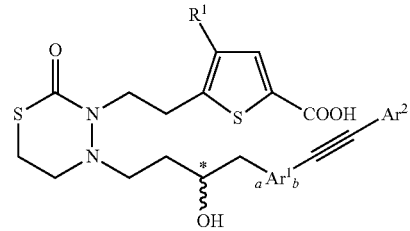

10 Claims, No Drawings

NITROGEN-CONTAINING 6-MEMBERED CYCLIC COMPOUND

TECHNICAL FIELD

The present invention relates to novel nitrogen-containing 6-membered cyclic compounds and medicaments using them as an active ingredient.

BACKGROUND ART

A bone fracture is a condition in which a bone is partially or completely interrupted or deformed by an external force given due to accident or falling down. Bone fractures are classified into complete fracture (break) and incomplete fracture (crack), simple fracture (there is one fracture line) and comminuted fracture (complicated break of bone), closed fracture (fracture part is not exposed out of the body) and open fracture (fracture part is exposed out of the body) or the like. Bone fractures impose serious troubles on patients' daily life activities, and healing thereof takes a considerably long period of time, although it depends on the fracture part and presence or absence of slippage (dislocation) of bone. A condition of bone union without correction of the dislocation is called "malunion". As conditions of bone fracture, although it depends on part and type of bone fracture, there may occur such conditions as "delayed union" in which union is not obtained even 3 to 9 months after being wounded due to various factors such as aging, diabetes, and smoking, and "nonunion" in which union is not obtained even 9 months after being wounded, and arrest of the fracture healing process is suspected. In such cases as malunion, delayed union, and nonunion, pain or discomfort accompanies, normal functional healing of fracture parts is not obtained, and therefore fracture patients' QOL is markedly degraded.

Considered especially serious problems in the fracture treatment are fractures accompanying osteoporosis. Fractures accompanying osteoporosis frequently occur at metaphyses of appendicular bones and spine, and in particular, femoral neck fracture, vertebral compression fracture, fracture of the distal end of radius, and fracture of the proximal end of humerus are regarded as four major fractures observed in osteoporosis. Fractures accompanying osteoporosis have a problem that redintegration thereof is difficult because of the bone fragility, and even if osteosynthesis is performed, sufficient stability can hardly be obtained, and inappropriate fixation causes malunion, delayed union, and also nonunion. Further, since daily activities are restrained during the fracture treatment period, there is induced a negative spiral that disuse bone mass reduction and muscular atrophy are advanced, and they newly invite falling down and fracture. In particular, delay of normal healing from centrum fracture or femoral neck fracture compels patients to be bedridden. The incident rates of various and critical complications such as muscular weakness, joint contracture, decubital ulcer, dementia, urinary tract infection, and cardiopulmonary hypofunction accompanying systemic disuse in these patients are extremely high, and significant reduction of survival rate after wounding has been reported (Non-patent document 1).

As described above, fractures, especially fractures accompanying osteoporosis, induce degradation of QOL, severe complications, and also significant influence on vital prognosis, and therefore they pose extremely serious social problems such as increases of health care cost and burden of caring. Treatments of fractures are currently performed by returning the bone condition to that of anatomically normal position, and performing fixation aiming at obtaining healing to the functional level before the wounding as far as possible by normal bone restoration process mechanism with preventing complications such as malunion, delayed union, and nonunion.

As treatments for positively promoting healing of fractures, ultrasonic fracture treatment apparatuses are used, and as therapeutic drugs, bone morphogenetic protein (BMP) preparations, parathyroid hormone preparations, fibroblast growth factor (FGF) preparations and the like are clinically used, or clinical applications thereof have been attempted. However, in spite of uses or attempts of use of such variety of drugs as mentioned above, the number of patients of bone diseases such as fracture is ever increasing every year, for example, the number of femoral neck fracture patients was presumed to be 1,700,000 all over the world in 1990, and it is predicted to increase to be 6,300,000 in 2050. In this respect, development of innovative new drugs having prophylactic and/or therapeutic effect for bone diseases such as fracture is desired.

It is known that prostaglandin $E_2$ (henceforth abbreviated as $PGE_2$) has various physiological functions such as pain-producing action and oxytocic action, and it is also well known that it plays an important role in bone metabolism. When $PGE_2$ is added to a marrow cell culture system, the alkaline phosphatase activity, which is a marker of calcified bone-like nodule formation and differentiation of osteoblasts, increases. It has been also revealed that when $PGE_2$ is actually administered to laboratory animals such as rats, or humans, osteogenesis rises, and bone mass increases. Further, when $PGE_2$ is topically administered to a bone in the form of sustained release preparation, osteogenesis is promoted at the administration site, and therefore effect of positively promoting osteogenesis systemically or locally can be expected for $PGE_2$.

However, since $PGE_2$ exhibits side reactions such as pain-producing action and oxytocic action as described above, which should be avoided for continuous long-term administration, there is desired a selective $PGE_2$ derivative that safely and effectively acts on bone tissues. For example, as the receptors of $PGE_2$, four kinds of them, $EP_1$, $EP_2$, $EP_3$, and $EP_4$ receptors, have so far been reported for mouse, rat, dog, human and the like, and since expression sites thereof and intracellular signal transduction systems to be activated by them are different, compounds selective for each subtype have been created.

It has been suggested that, among the four kinds of receptors on which $PGE_2$ acts, the $EP_2$ and $EP_4$ receptors play important roles in bone metabolism in cells and animals, and both conjugate with the Gs protein to increase cAMP in osteoblasts. There have been developed $EP_2$-selective agonists, $EP_4$-selective agonist, and $EP_2$/$EP_4$ agonists so far, and significant osteogenesis action or fracture healing-promoting effect thereof have been demonstrated in animal models by systemic or local administration. As compounds that act on the PGE receptors, for example, the compounds described in Patent documents 1 to 8 are known.

PRIOR ART REFERENCES

Patent Documents

Patent document 1: International Patent Publication WO02/24647
Patent document 2: International Patent Publication WO02/42268

Patent document 3: International Patent Publication WO03/007941

Patent document 4: International Patent Publication WO03/035064

Patent document 5: International Patent Publication WO2004/063158

Patent document 6: International Patent Publication WO2004/085430

Patent document 7: U.S. Pat. No. 6,747,037

Patent document 8: International Patent Publication WO2006/080323

Non-Patent Documents

Non-patent document 1: C. Cooper et al., Am. J. Epidemiol., 137, 1001-1005, 1993

SUMMARY OF THE INVENTION

Object to be Achieved by the Invention

An object to be achieved by the present invention is to provide a novel compound having superior $EP_4$ receptor agonist activity. Preferably, the object is to provide a novel compound having a superior $EP_4$ receptor-selective agonist activity. Another object is to provide a novel compound useful as an active ingredient of a medicament for prophylactic and/or therapeutic treatment of a disease relating to the $EP_4$ receptor agonization, for example, a novel compound useful as an active ingredient of a medicament for therapeutic treatment of fracture and/or promoting healing of fracture. Still another object is to provide a medicament containing such a compound.

Means for Achieving the Object

In order to achieve the aforementioned objects, the inventors of the present invention conducted various researches. As a result, they found that the compounds of the present invention represented by the following formula (1) have superior $EP_4$ receptor agonist activity, in particular, the compounds according to a certain embodiment of the present invention have superior $EP_4$ receptor-selective agonist activity, and those compounds are useful for prophylactic and/or therapeutic treatment of a disease relating to the $EP_4$ receptor agonization, for example, therapeutic treatment and/or promotion of healing of fracture, and came to accomplish the present invention. It is considered that it is preferable to provide a compound having an $EP_4$-receptor-selective agonist activity for the following reasons. Namely, while the $EP_4$ receptor is observed in osteoblasts and osteoclasts in human cultured osteoblasts and osseous tissues, expression of the $EP_2$ receptor have not been detected (P. Sarrazin, G et al. Prostaglandins Leukot. Essent. Fatty Acids, 64, 203-210, 2001; I. Fortier et al., Prostaglandins Leukot. Essent. Fatty Acids, 70, 431-439, 2004), and therefore it is considered that the most important target of $PGE_2$ for the action in osseous tissues is the $EP_4$ receptor, and an $EP_4$ receptor-selective agonist can be a safe and effective medicament for osteoanagenesis treatment. Of course, compounds having an $EP_2$ receptor agonist activity are not excluded from the compounds of the present invention.

The present invention thus provides the followings.

[1] A compound represented by the following general formula (1);

(1)

[Formula 1]

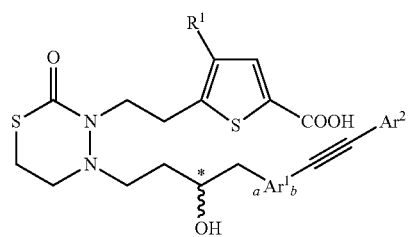

[wherein, in the formula (1), $R^1$ represents —H, or halogen;

$Ar^1$ represents any substituent selected from the group which may be substituted with 1 to 3 of the same or different substituents selected from the group consisting of —F and methyl (provided that

[Formula 2]

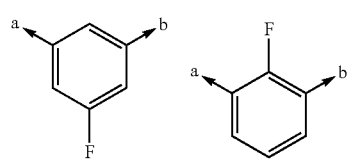

are excluded), wherein the group $G^1$ is a group consisting of

[Formula 3]

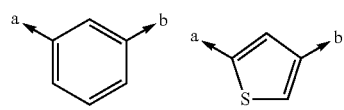

(a and b represent binding direction);

$Ar^2$ represents any substituent selected from the group $G^2$, which may be substituted with 1 to 3 of the same or different substituents selected from the group consisting of cyano, —Cl, methyl, methoxy, and phenyl (provided that

[Formula 4]

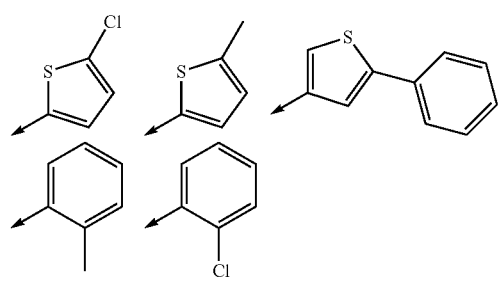

are excluded), wherein the group $G^2$ is a group consisting of phenyl, thienyl, furyl, and thiazolyl; and

* represents an asymmetric carbon], or a salt thereof.

[2] The compound or a salt thereof according to [1] mentioned above, wherein $R^1$ is —H, —Cl, or —Br.

[3] The compound or a salt thereof according to [2] mentioned above, wherein $Ar^1$ is any substituent selected from the group consisting of

[Formula 5]

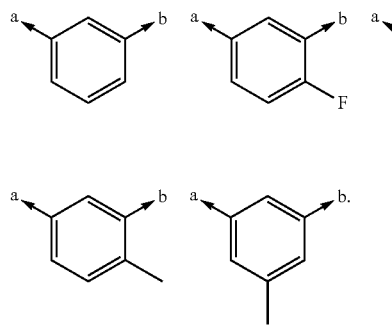

[3-2] The compound or a salt thereof according to [1] or [2] mentioned above, wherein $Ar^1$ is any substituent selected from the group consisting of

[Formula 6]

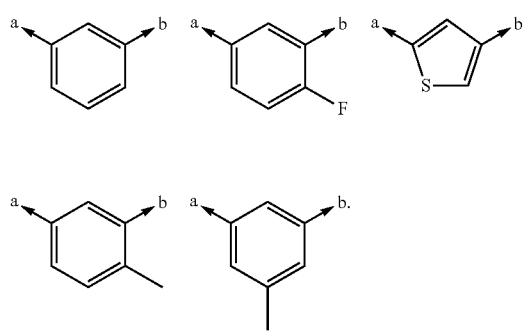

[3-3] The compound or a salt thereof according to [1] or [2] mentioned above, wherein $Ar^1$ is any substituent selected from the group consisting of

[Formula 7]

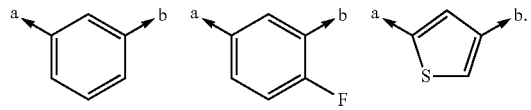

[4] The compound or a salt thereof according to [2] mentioned above, wherein $Ar^1$ is

[Formula 8]

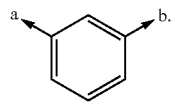

[4-2] The compound or a salt thereof according to [1] or [2] mentioned above, wherein $Ar^1$ is

[Formula 9]

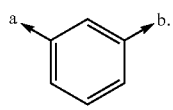

[4-3] The compound or a salt thereof according to [1] or [2] mentioned above, wherein $Ar^1$ is

[Formula 10]

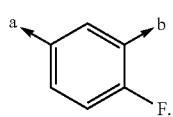

[4-4] The compound or a salt thereof according to [1] or [2] mentioned above, wherein $Ar^1$ is

[Formula 11]

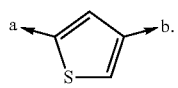

[5] The compound or a salt thereof according to [3] or [4] mentioned above, wherein $Ar^2$ is any substituent selected from the group consisting of

[Formula 12]

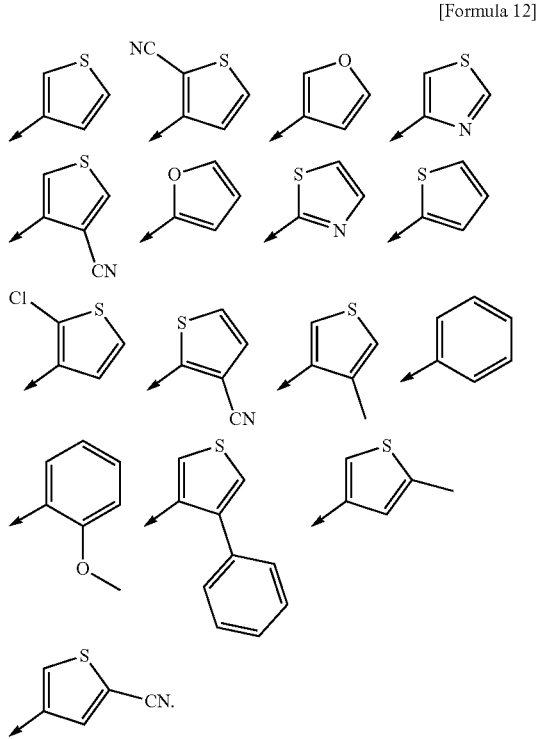

[5-2] The compound or a salt thereof according to any one of [1] to [4-4] mentioned above, wherein Ar² is any substituent selected from the group consisting of

[Formula 13]

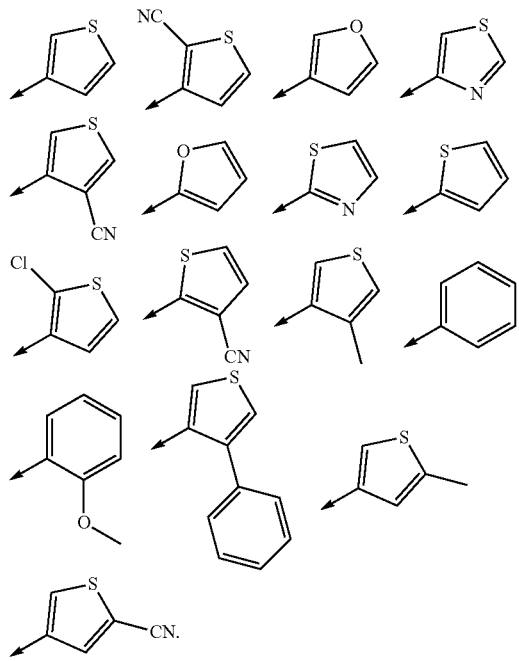

When the cited item numbers are indicated with such a range as [1] to [4-4] mentioned above, and the range includes an item indicated with a number having a subnumber such as [3-2], it is meant that the item indicated with the number having a subnumber such as [3-2] is also cited. The same shall apply to the following definitions.

[6] The compound or a salt thereof according to [3] or [4] mentioned above, wherein Ar² is any substituent selected from the group consisting of

[Formula 14]

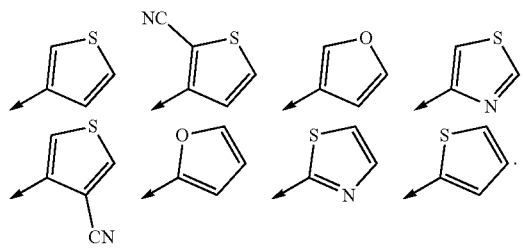

[6-2] The compound or a salt thereof according to any one of [1] to [4-4] mentioned above, wherein Ar² is any substituent selected from the group consisting of

[Formula 15]

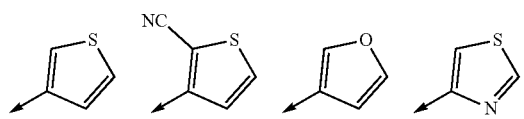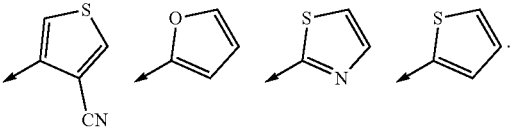

[7] The compound or a salt thereof according to [3] or [4] mentioned above, wherein Ar² is any substituent selected from the group consisting of

[Formula 16]

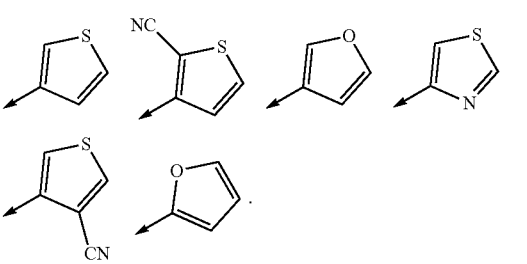

[7-2] The compound or a salt thereof according to any one of [1] to [4-4] mentioned above, wherein Ar² is any substituent selected from the group consisting of

[Formula 17]

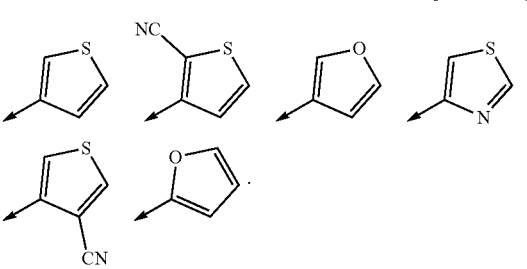

[7-3] The compound or a salt thereof according to any one of [1] to [4-4] mentioned above, wherein Ar² is any substituent selected from the group consisting of

[Formula 18]

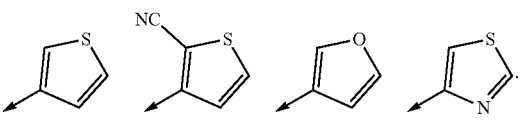

[7-4] The compound or a salt thereof according to any one of [1] to [4-4] mentioned above, wherein Ar² is

[Formula 19]

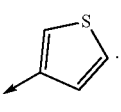

[7-5] The compound or a salt thereof according to any one of [1] to [4-4] mentioned above, wherein Ar² is

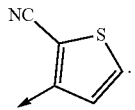
[Formula 20]

[7-6] The compound or a salt thereof according to any one of [1] to [4-4] mentioned above, wherein Ar² is

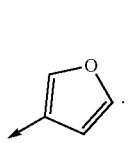
[Formula 21]

[7-7] The compound or a salt thereof according to any one of [1] to [4-4] mentioned above, wherein Ar² is

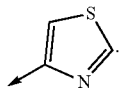
[Formula 22]

[8] The compound or a salt thereof according to [7] mentioned above, wherein R¹ is —H.

[8-2] The compound or a salt thereof according to any one of [1] to [7-7] mentioned above, wherein R¹ is —H.

[9] The compound or a salt thereof according to [7] mentioned above, wherein R¹ is —Cl.

[9-2] The compound or a salt thereof according to any one of [1] to [7-7] mentioned above, wherein R¹ is —Cl.

[10] The compound or a salt thereof according to [7] mentioned above, wherein R¹ is —Br.

[10-2] The compound or a salt thereof according to any one of [1] to [7-7] mentioned above, wherein R¹ is —Br.

[11] The compound or a salt thereof according to [1] mentioned above, wherein R¹ is —H, —Cl, or —Br;

Ar¹ is any substituent selected from the group consisting of

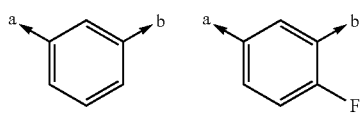
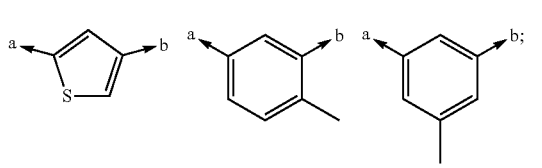
[Formula 23]

and

Ar² is any substituent selected from the group consisting of

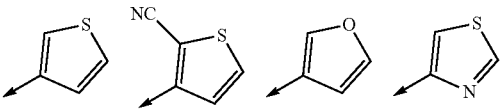
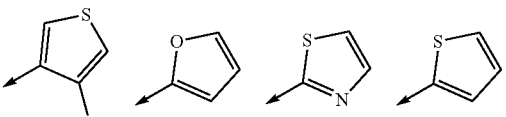
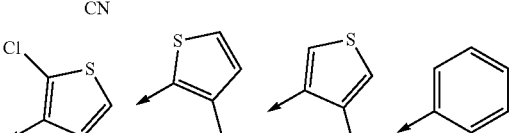
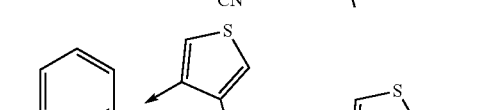
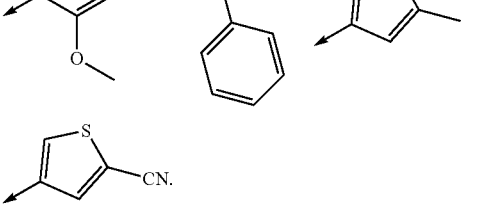
[Formula 24]

[11-2] The compound or a salt thereof according to [1] mentioned above, wherein R¹ is —H, —Cl, or —Br;

Ar¹ is any substituent selected from the group consisting of

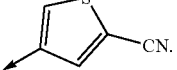
[Formula 25]

and

Ar² is any substituent selected from the group consisting of

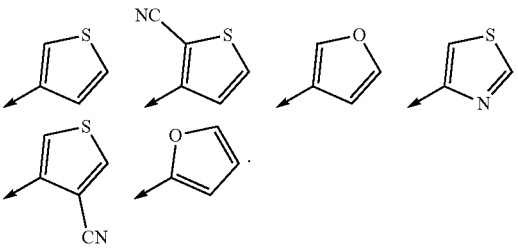
[Formula 26]

[11-3] The compound or a salt thereof according to [1] mentioned above, wherein R¹ is —H, —Cl, or —Br;

Ar¹ is any substituent selected from the group consisting of

[Formula 27]

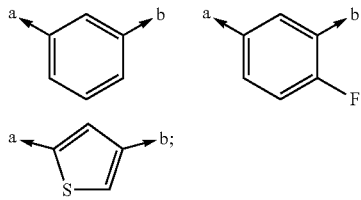

and

Ar² is any substituent selected from the group consisting of

[Formula 28]

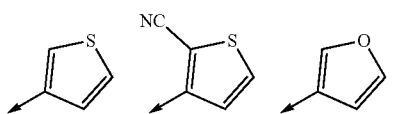

[11-4] The compound or a salt thereof according to [1] mentioned above, wherein R¹ is —H, —Cl, or —Br;

Ar¹ is any substituent selected from the group consisting of

[Formula 29]

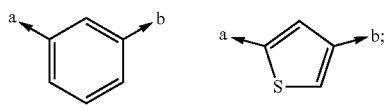

and

Ar² is any substituent selected from the group consisting of

[Formula 30]

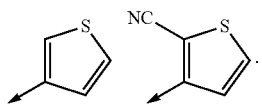

[12] Any compound selected from the following group, or a salt thereof;

[Formula 31]

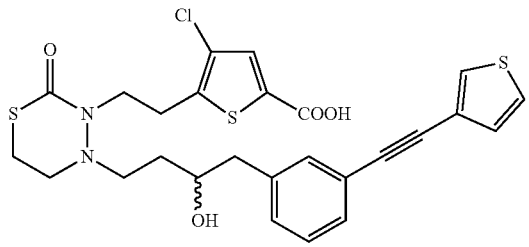

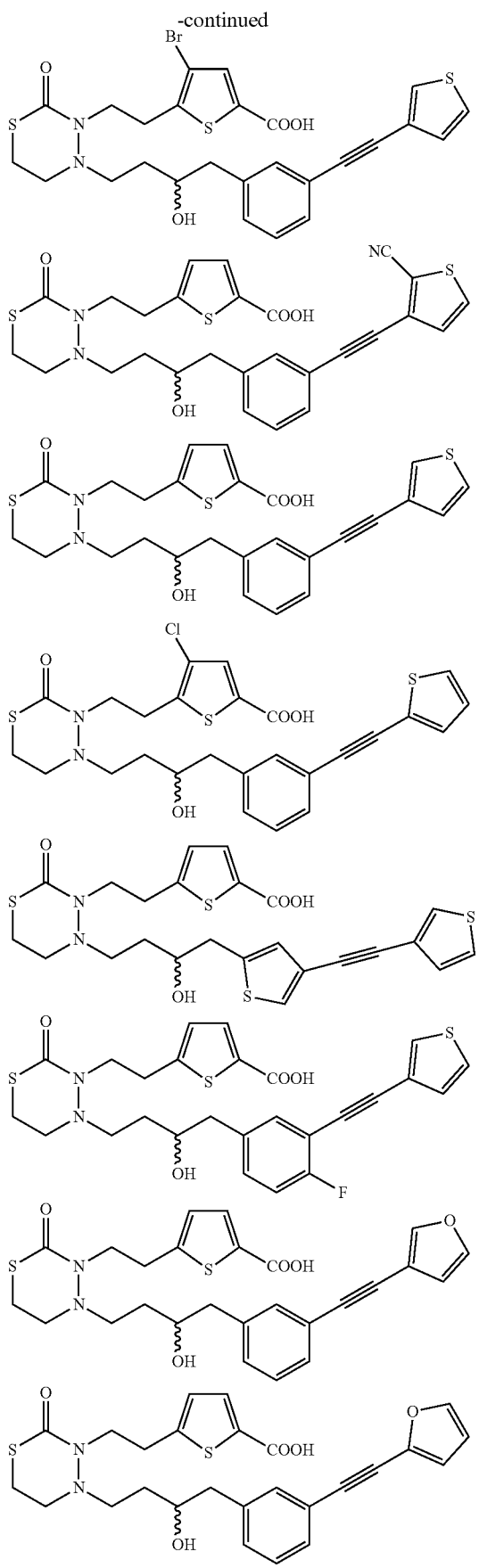

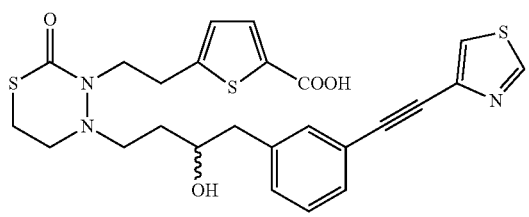
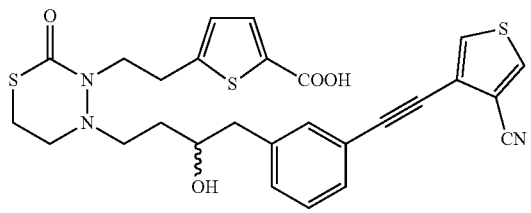
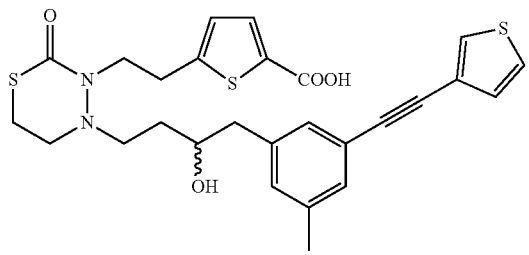
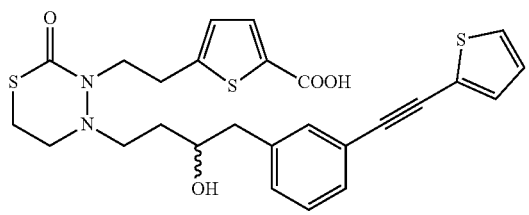
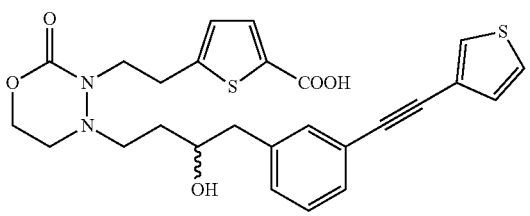
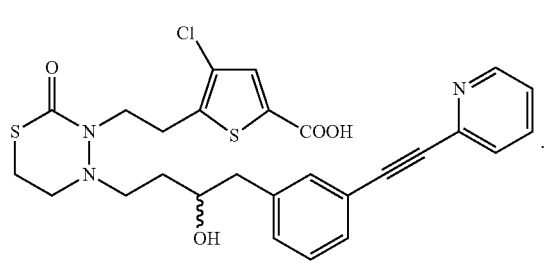
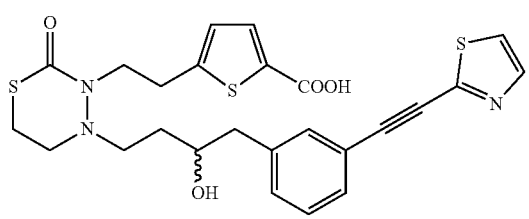
[13] The compound mentioned below, or a salt thereof;
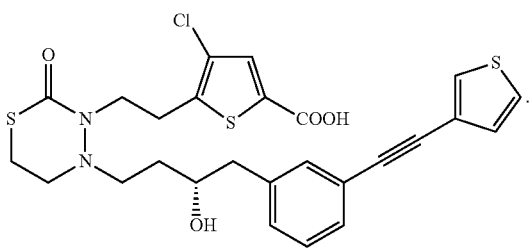 [SMILES: O=C(O)c1cc(Cl)c(CCN2C(=O)SCCN2CC[C@@H](O)Cc2cccc(C#Cc3ccsc3)c2)s1]
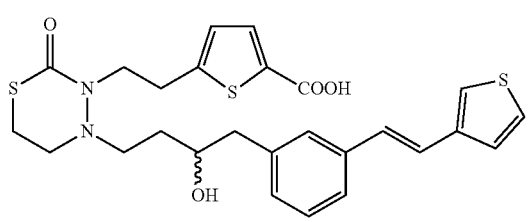
[14] The compound mentioned below, or a salt thereof;
[Formula 33]
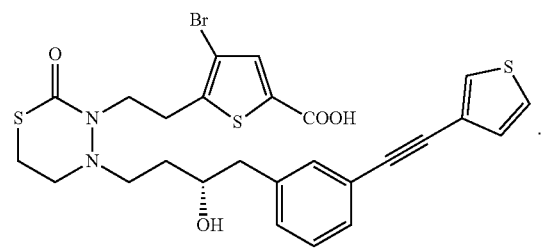
[15] The compound mentioned below, or a salt thereof;
[Formula 34]
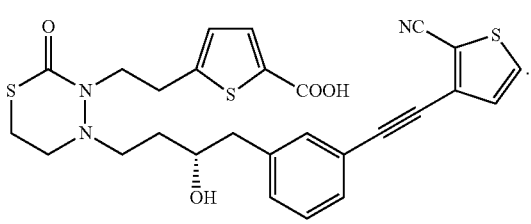

[16] The compound mentioned below, or a salt thereof;

[Formula 35]

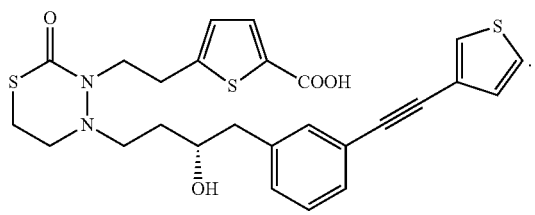

[17] The compound mentioned below, or a salt thereof;

[Formula 36]

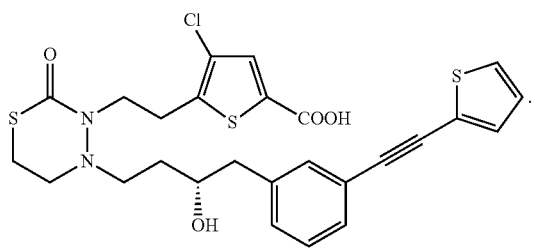

[18] The compound mentioned below, or a salt thereof;

[Formula 37]

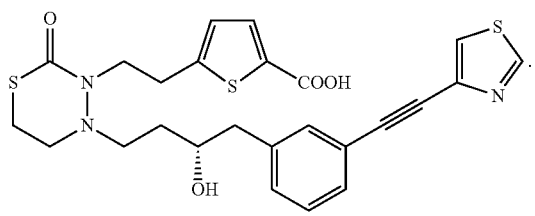

[19] The compound mentioned below, or a salt thereof;

[Formula 38]

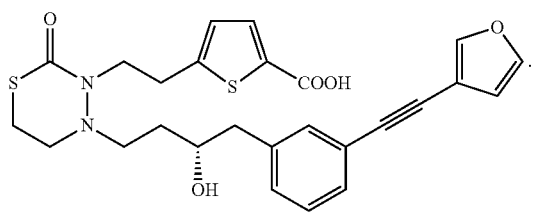

[20] A medicament containing the compound according to any one of [1] to [19] mentioned above or a pharmaceutically acceptable salt thereof as an active ingredient.
[21] The medicament according to [20] mentioned above, which is for prophylactic and/or therapeutic treatment of a disease relating to $EP_4$ receptor agonization.
[22] The medicament according to [20] mentioned above, which is for promotion of osteogenesis.
[23] The medicament according to [20] mentioned above, which is for therapeutic treatment and/or promotion of healing of fracture.
[24] The medicament according to [20] mentioned above, which is for therapeutic treatment and/or promotion of healing of bone defect.
[25] The medicament according to [20] mentioned above, which is for promotion of bone union.
[25-2] The medicament according to [25] mentioned above, which is for promotion of bone union in spinal fusion surgeries.
[26] An $EP_4$ agonist containing the compound according to any one of [1] to [19] mentioned above or a pharmaceutically acceptable salt thereof as an active ingredient.
[27] A pharmaceutical composition for therapeutic treatment of fracture, which contains the compound according to any one of [1] to [19] mentioned above or a pharmaceutically acceptable salt thereof, and a pharmaceutically acceptable carrier.
[28] A microsphere preparation containing the compound according to any one of [1] to [19] mentioned above or a pharmaceutically acceptable salt thereof, and a lactic acid/glycolic acid copolymer.
[29] The compound according to any one of [1] to [19] mentioned above or a pharmaceutically acceptable salt thereof, which is used for therapeutic treatment of fracture.
[30] A method for therapeutic treatment of fracture in a mammal, which comprises the step of administrating an effective amount of the compound according to any one of [1] to [19] mentioned above or a pharmaceutically acceptable salt thereof to the mammal.

Effect of the Invention

The "compounds represented by the formula (1) and salts thereof" (henceforth also referred to simply as "the compounds of the present invention") have a superior $EP_4$ receptor agonist activity. The compounds of the present invention can be used as an active ingredient of a medicament for prophylactic and/or therapeutic treatment of a disease relating to $EP_4$ receptor agonization, for example, therapeutic treatment and/or promotion of healing of fracture. As another embodiment, the compounds of the present invention can be used as a reagent having an $EP_4$ receptor agonist activity.

MODES FOR CARRYING OUT THE INVENTION

Hereafter, the present invention will be specifically explained.

In the present specification, carbon atom may be simply represented as "C", hydrogen atom as H", oxygen atom as "O", sulfur atom as "S", and nitrogen atom as N". Further, carbonyl group may be simply represented as "—C(O)—", carboxyl group as "—COO—", sulfinyl group as "—S(O)—", sulfonyl group as "—S(O)$_2$—", ether bond as "—O—", and thioether bond as "—S—" (each "—" in these groups indicates a bond).

In the present specification, the alkyl having 1 to 4 carbon atoms means methyl, ethyl, propyl, butyl, or an isomer thereof [normal (n), iso, secondary (sec), tertiary (t) and the like].

In the present specification, the acyl having 2 to 6 carbon atoms means acetyl, propanoyl, butanoyl, pentanoyl, hexanoyl, or an isomer thereof.

In the present specification, the alkoxy having 1 to 4 carbon atoms means methoxy, ethoxy, propoxy, butoxy, or an isomer thereof.

In the present specification, the halogen means fluoro (—F), chloro (—Cl), bromo (—Br), or iodo (—I).

In the present invention, all isomers are included, unless specifically indicated. For example, the alkyl, alkenyl, alkynyl, alkoxy, alkylthio, alkylene, alkenylene, and alkynylene include linear and branched groups. Further, any of isomers based on a double bond, ring, or condensed ring (E- or Z-isomers, or cis- or trans-isomers), isomers based on the presence of an asymmetric carbon and the like (R- or S-isomer, an isomer based on α- or β-configuration, enantiomers, diastereomers and the like), optically active substances showing optical rotation (D- or L-isomers, or d- or l-isomers), isomers based on polarity in chromatographic separation (high polarity isomers or low polarity isomers), equilibrated compounds, rotational isomers, mixtures of these isomers at arbitrary ratios, and racemates fall within the scope of the present invention.

In the present specification, as apparent for those skilled in the art, the symbol:
[Formula 39]
,,,,\\
indicates that the bond is on the back of the plane (i.e., α-configuration), the symbol:
[Formula 40]

indicates that the bond is in front of the plane (i.e., β-configuration), the symbol:
[Formula 41]

means α-configuration or β-configuration, or a mixture thereof, and the symbol:
[Formula 42]

means α mixture of α-configuration and 6-configuration, unless especially indicated.

Hereafter, the compounds represented by the formula (1), or salts thereof will be explained in detail.

$R^1$ is, for example, —H, or halogen. According to another embodiment, $R^1$ is, for example, —H, —Cl, or —Br. According to further another embodiment, $R^1$ is, for example, —H.

$Ar^1$ is, for example, any substituent selected from the group $G^1$, which may be substituted with 1 to 3 of the same or different substituents selected from the group consisting of —F and methyl (provided that

[Formula 43]

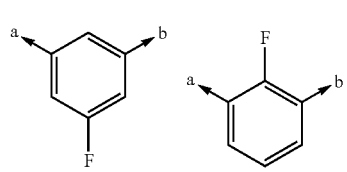

are excluded), wherein the group $G^1$ is a group consisting of

[Formula 44]

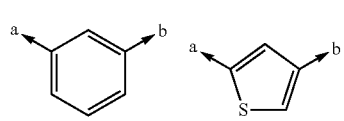

(a and b represent binding direction).

According to another embodiment of the group consisting of —F and methyl mentioned above, the group consists of, for example, —F, and according to further another embodiment, the group consists of, for example, methyl.

According to another embodiment of the group $G^1$, the group consists of, for example,

[Formula 45]

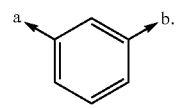

According to another embodiment of $Ar^1$, $Ar^1$ is, for example, any substituent selected from the group consisting of

[Formula 46]

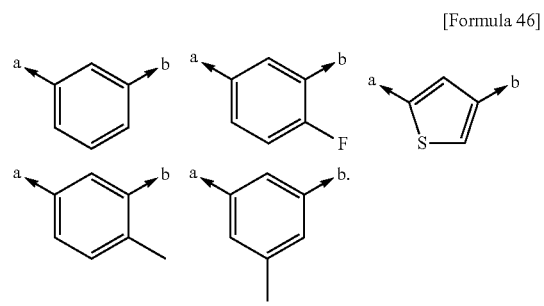

According to further another embodiment of $Ar^1$, $Ar^1$ is, for example, any substituent selected from the group consisting of

[Formula 47]

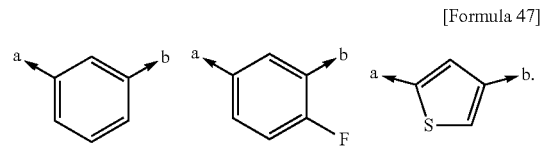

According to further another embodiment of $Ar^1$, $Ar^1$ is, for example,

[Formula 48]

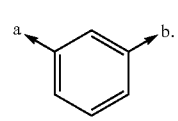

According to further another embodiment of $Ar^1$, $Ar^1$ is, for example,

[Formula 49]

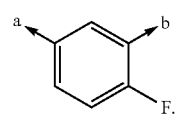

According to further another embodiment of $Ar^1$, $Ar^1$ is, for example,

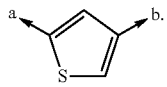

[Formula 50]

When $Ar^1$ is substituted with 1 to 3 of the same or different substituents selected from the group consisting of —F and methyl, according to another embodiment, $Ar^1$ is, for example, substituted with 1 or 2 of the same or different substituents selected from the group consisting of —F and methyl, and according to further another embodiment, $Ar^1$ is, for example, substituted with one of —F or methyl. Unsubstituted $Ar^1$ is also one of preferred embodiments.

$Ar^2$ is, for example, any substituent selected from the group $G^2$, which may be substituted with 1 to 3 of the same or different substituents selected from the group consisting of cyano, —Cl, methyl, methoxy, and phenyl (provided that

[Formula 51]

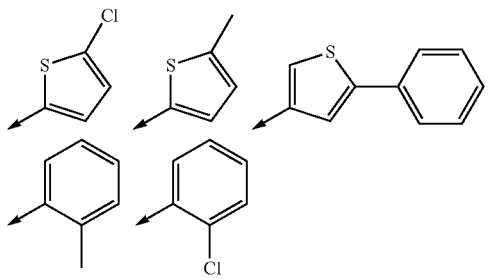

are excluded).

The group $G^2$ mentioned above is a group consisting of phenyl, thienyl, furyl, and thiazolyl.

According to another embodiment of the group consisting of cyano, —Cl, methyl, methoxy, and phenyl, the group consists of, for example, cyano.

According to another embodiment of the group $G^2$, $G^2$ is, for example, a group consisting of thienyl and furyl.

According to further another embodiment of the group $G^2$, the group consists of, for example, thienyl.

According to another embodiment of $Ar^2$, $Ar^2$ is, for example, any substituent selected from the group consisting of

[Formula 52]

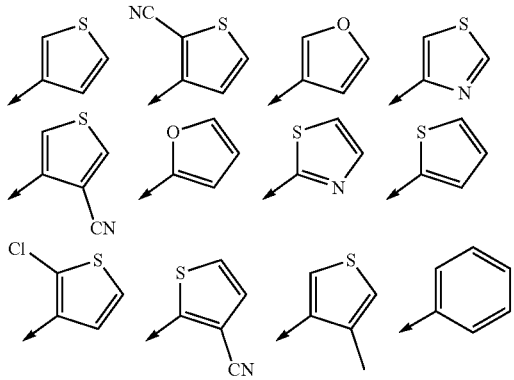

-continued

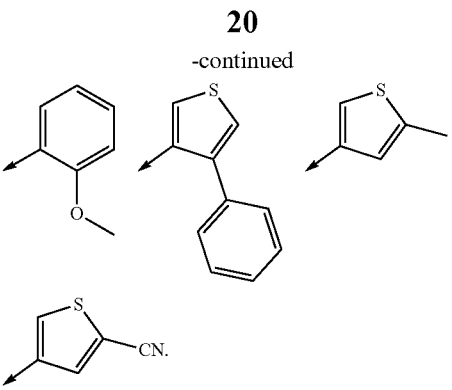

According to further another embodiment of $Ar^2$, $Ar^2$ is, for example, any substituent selected from the group consisting of

[Formula 53]

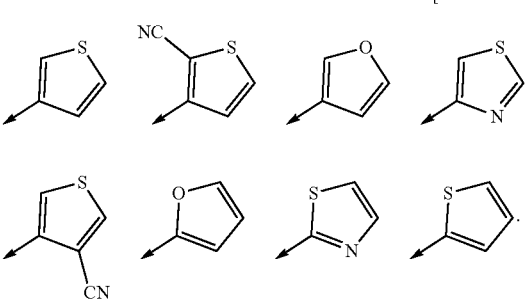

According to further another embodiment of $Ar^2$, $Ar^2$ is, for example, any substituent selected from the group consisting of

[Formula 54]

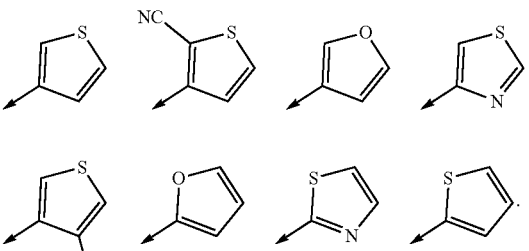

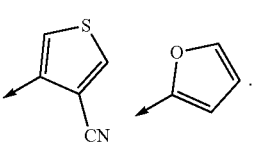

According to further another embodiment of $Ar^2$, $Ar^2$ is, for example, any substituent selected from the group consisting of

[Formula 55]

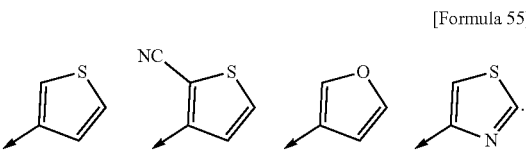

According to further another embodiment of Ar², Ar² is, for example,

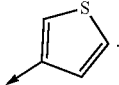

[Formula 56]

According to further another embodiment of Ar², Ar² is, for example,

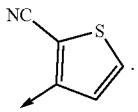

[Formula 57]

According to further another embodiment of Ar², Ar² is, for example,

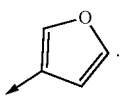

[Formula 58]

According to further another embodiment of Ar², Ar² is, for example,

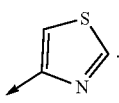

[Formula 59]

When Ar² is substituted with 1 to 3 of the same or different substituents selected from the group consisting of cyano, —Cl, methyl, methoxy, and phenyl, according to another embodiment, Ar² is, for example, substituted with 1 or 2 of the same or different substituents selected from the group consisting of cyano, —Cl, methyl, methoxy, and phenyl, and according to further another embodiment, Ar² is, for example, substituted with 1 of cyano, —Cl, methyl, methoxy, or phenyl. Unsubstituted Ar² is also one of preferred embodiments.

As specific compounds falling within the scope of the present invention, the following compounds can be exemplified.

[Formula 60]

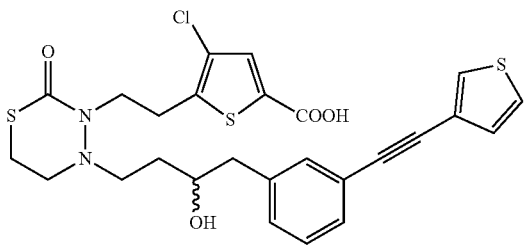

-continued

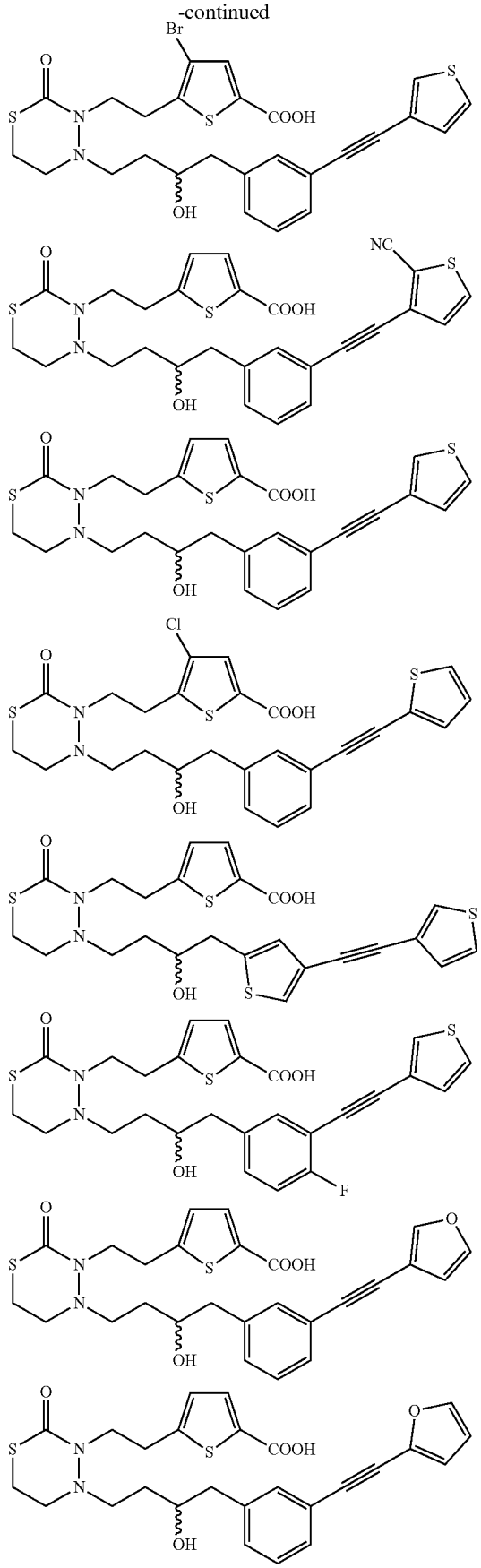

23
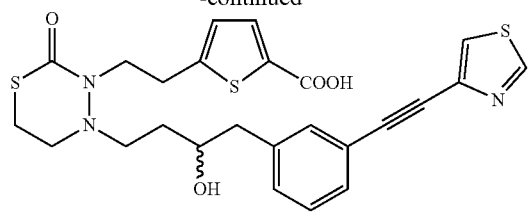
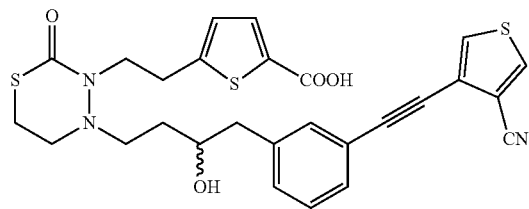
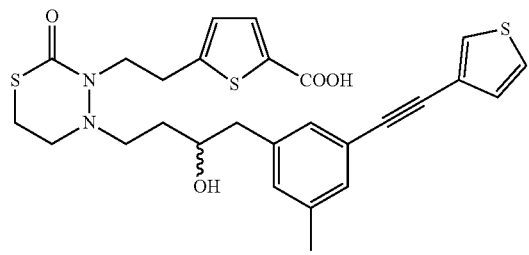
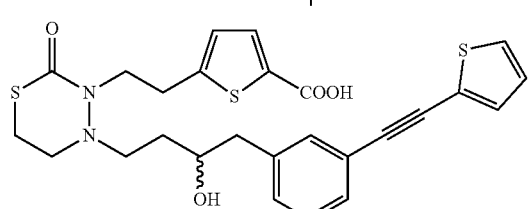
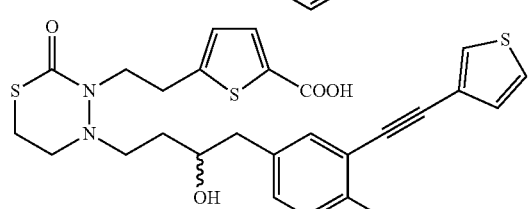
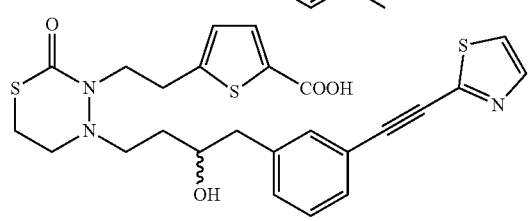
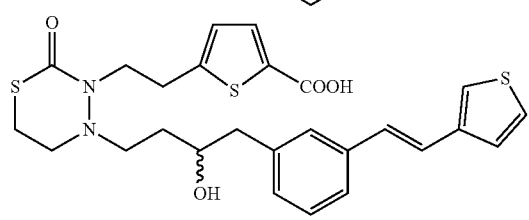
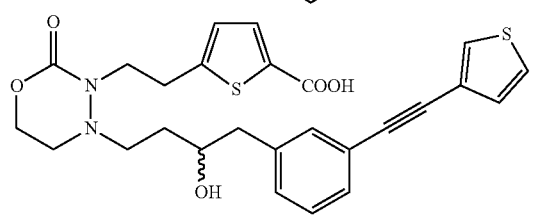
24
-continued
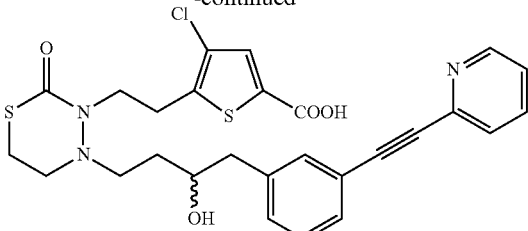
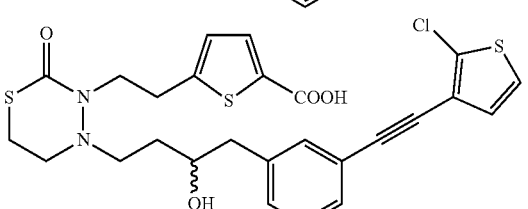
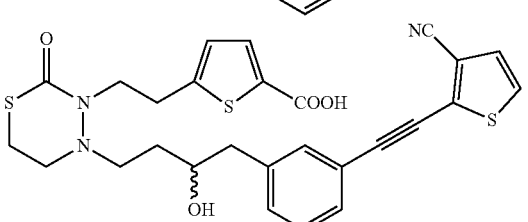
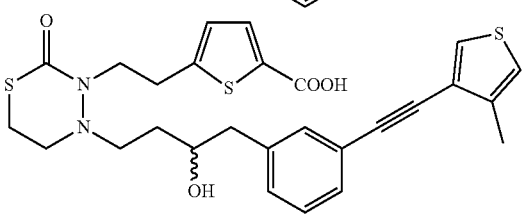
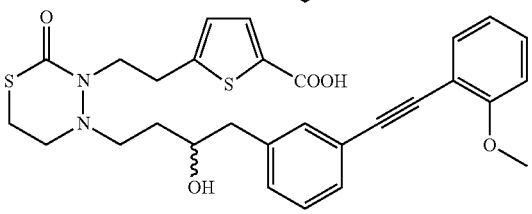
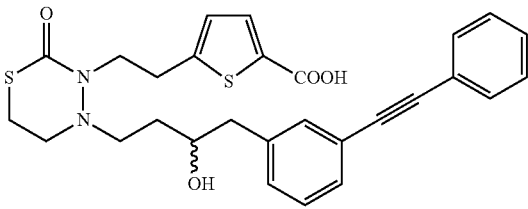
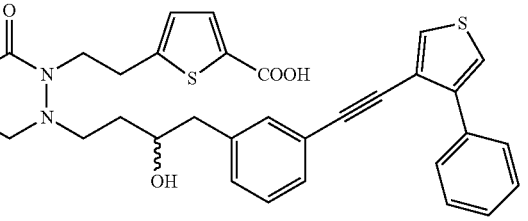
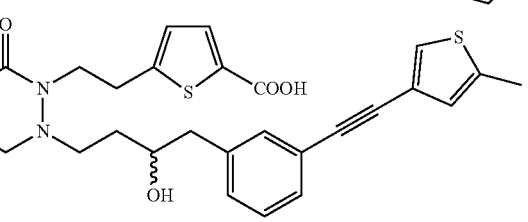

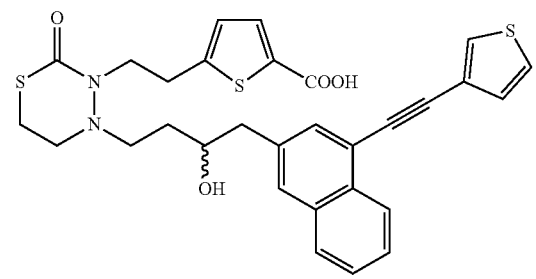
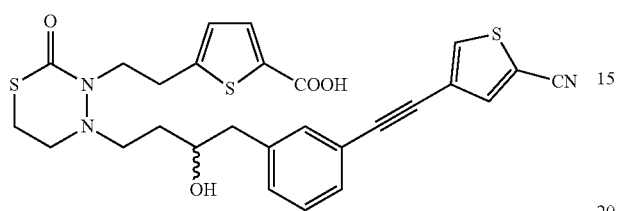
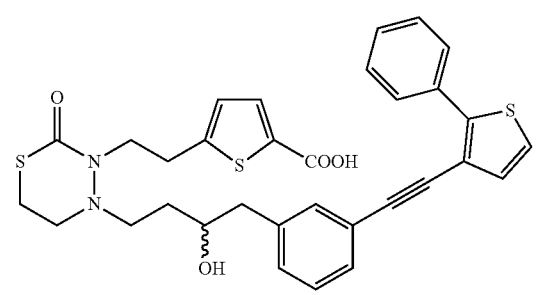
As further other specific examples of the compounds falling within the scope of the present invention, the following compounds can be exemplified.
[Formula 61]
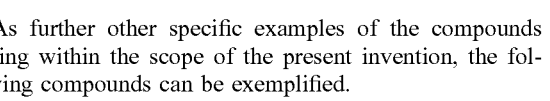
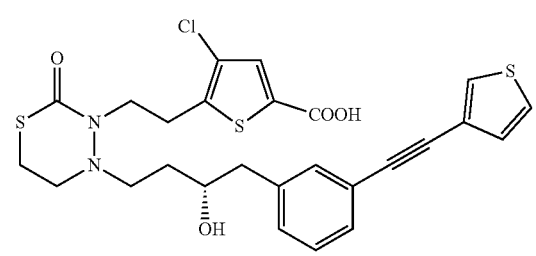
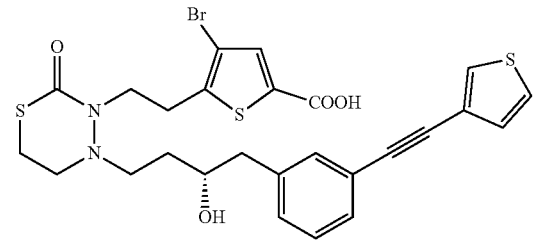
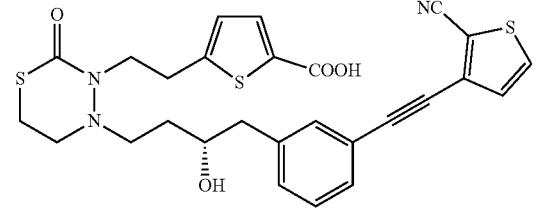
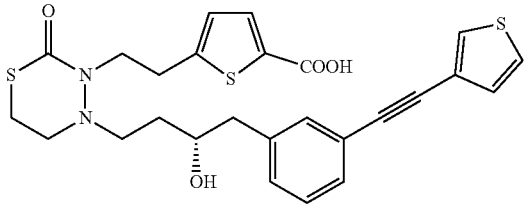
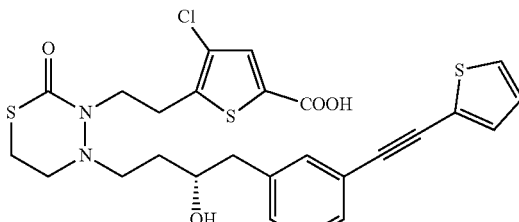
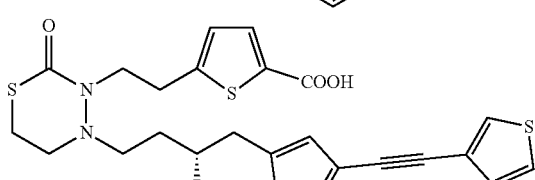
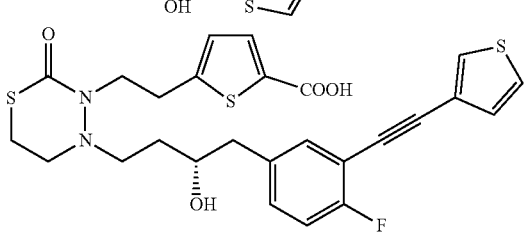
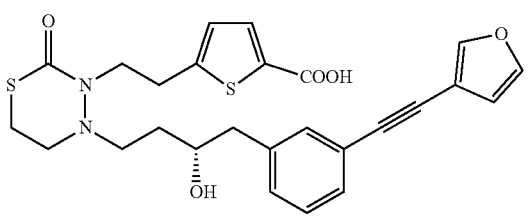
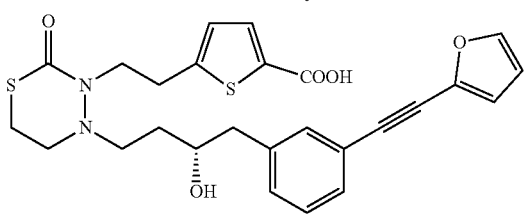
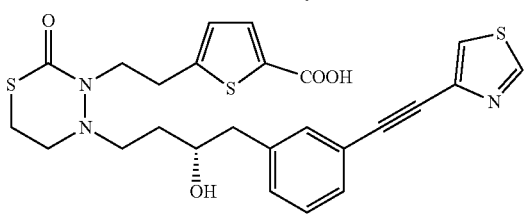

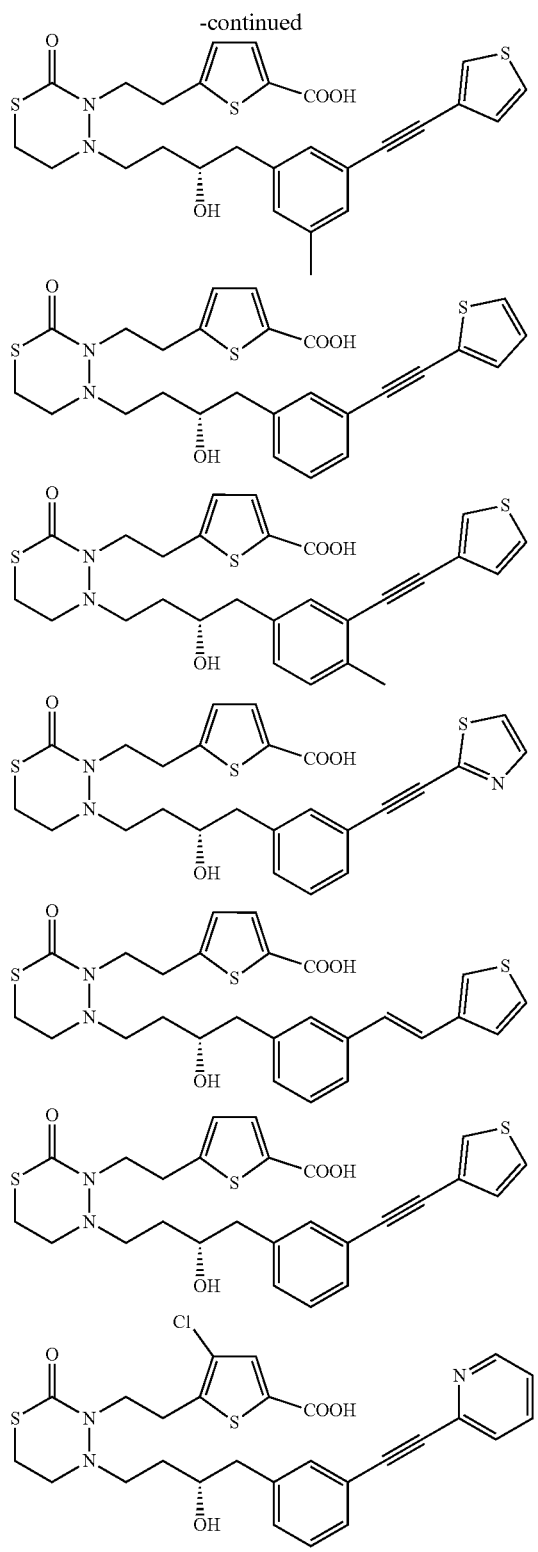

In this specification, the "compounds represented by the formula (1)" is generally understood as the compounds represented by the formula (1) in the free form. Examples of the salt thereof include the following salts.

The type of the salt of the compounds represented by the formula (1) is not particularly limited, and it may be an acid addition salt, or a base addition salt, and may be in the form of an intramolecular counter ion. In particular, when the salt is used as an active ingredient of a medicament, the salt is preferably a pharmaceutically acceptable salt. When disclosure is made for use as a medicament in this specification, the salt of the compounds represented by the formula (1) is usually understood as a pharmaceutically acceptable salt. Acid addition salts include, for example, acid addition salts with an inorganic acid such as hydrochloric acid, hydrobromic acid, hydroiodic acid, sulfuric acid, nitric acid, and phosphoric acid, and acid addition salts with an organic acid such as formic acid, acetic acid, propionic acid, oxalic acid, malonic acid, succinic acid, methanesulfonic acid, ethanesulfonic acid, benzenesulfonic acid, citric acid, malic acid, tartaric acid, dibenzoyltartaric acid, mandelic acid, maleic acid, fumaric acid, aspartic acid, and glutamic acid. As base addition salts, for example, base addition salts with an inorganic base such as sodium, potassium, magnesium, calcium, and aluminum, base addition salts with an organic base such as methylamine, 2-aminoethanol, arginine, lysine, and ornithine and the like can be exemplified. However, the type of the salt is not limited to these, and it can of course be appropriately selected by those skilled in the art.

The compounds of the present invention may be in the form of hydrate. The compounds of the present invention may also be in the form of anhydride.

The compounds of the present invention may be in the form of solvate. The compounds of the present invention may also be in the form of non-solvate.

The compounds of the present invention may be in the form of crystal. The compounds of the present invention may also be in an amorphous form.

More specifically, the compounds of the present invention include anhydrides and non-solvates of the "compounds represented by the formula (1)", hydrates and/or solvates thereof, and crystals thereof.

The compounds of the present invention also include anhydrides and non-solvates of "salts of the compounds represented by the formula (1)", hydrates and/or solvates of the salts, and crystals thereof.

The compounds of the present invention may also be a pharmaceutically acceptable prodrug of "the compounds represented by the formula (1)". The pharmaceutically acceptable prodrug is a compound having a group that can be changed into amino group, hydroxyl group, carboxyl group or the like by solvolysis or under physiological conditions. For example, as a group that forms a prodrug for hydroxy group, or amino group, for example, an acyl group and an alkoxycarbonyl group are exemplified. As a group that forms a prodrug for carboxyl group, for example, methyl group, ethyl group, n-propyl group, isopropyl group, n-butyl group, isobutyl group, s-butyl group, t-butyl group, amino group, methylamino group, ethylamino group, dimethylamino group, and diethylamino group are exemplified.

Such a prodrug can be prepared by, for example, appropriately introducing a group that forms a prodrug into any of the compounds of the present invention at one or more arbitrary groups selected from hydroxyl group and amino group using a prodrug-forming reagent such as a corresponding halide in a conventional manner, then, if desired, appropriately isolating and purifying the compound in a conventional manner. A group that forms a prodrug can also be appropriately introduced into the compound of the present invention at carboxyl group by using such a prodrug-forming reagent as a corresponding alcohol or amine in a conventional manner.

The compounds of the present invention may have an asymmetric carbon. The steric configuration of such an asymmetric carbon is not particularly limited, and it may be in the S-configuration or R-configuration, or a mixture of the both. Any optically active substances based on such an asymmetric carbon in a pure form, stereoisomers such as diastereoisomers, arbitrary mixtures of stereoisomers, racemates and the like all fall within the scope of the compounds of the present invention.

In particular, the steric configuration of the asymmetric carbon indicated with "*" in the formula (1) is not particularly limited. However, the configuration shown below is one of the preferred embodiments.

[Formula 62]

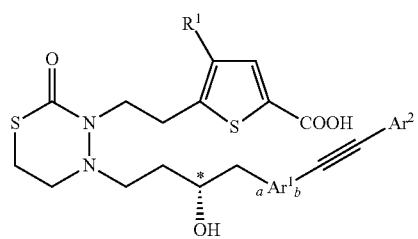

When Ar¹ is benzene ring among the groups of the group G¹, the steric configuration in the above formula is the S-configuration, and when Ar¹ is thiophene ring among the groups of the group G¹, the steric configuration in the above formula is the R-configuration.

<Preparation Methods of the Compounds of the Present Invention>

The compounds of the present invention are novel compounds not described in literature. Although the compounds of the present invention can be prepared by, for example, the following methods, the preparation method of the compounds of the present invention is not limited to the following methods.

Although reaction time in each of the reactions is not particularly limited, progress of the reactions can be easily monitored by analysis methods described later, and therefore the reactions may be terminated when the maximum yield of objective substance is obtained. Each of the reactions can be performed in an inert gas atmosphere, for example, under a nitrogen flow or an argon flow, as required. When protection with a protective group and subsequent deprotection are needed in each of the reactions, the reactions can be appropriately performed by utilizing the methods described below.

Examples of the protective group used in the present invention include the following groups: protective groups for carboxyl group (—COOH), protective groups for hydroxyl group (—OH), protective groups for an alkynyl group, protective groups for amino group (—NH₂) and the like.

Examples of the protective group for carboxyl group include, for example, an alkyl having 1 to 4 carbon atoms, an alkenyl having 2 to 4 carbon atoms, an alkyl having 1 to 4 carbon atoms and substituted with an alkoxy having 1 to 4 carbon atoms, an alkyl having 1 to 4 carbon atoms and substituted with 1 to 3 halogens and the like. Specific examples include methyl, ethyl, t-butyl, allyl, methoxyethyl, trichloroethyl and the like.

Examples of the protective groups for hydroxyl group include, for example, an alkyl having 1 to 4 carbon atoms, an alkenyl having 2 to 4 carbon atoms, an alkyl having 1 to 4 carbon atoms and substituted with an alkoxy having 1 to 4 carbon atoms, an alkyl having 1 to 4 carbon atoms and substituted with 1 to 3 halogens, a silyl substituted with three of the same or different alkyls having 1 to 4 carbon atoms or phenyls, tetrahydropyranyl, tetrahydrofuryl, propargyl, trimethylsilylethyl group and the like. Specific examples include methyl, ethyl, t-butyl, allyl, methoxymethyl (MOM), methoxyethyl (MEM), trichloroethyl, phenyl, methylphenyl, chlorophenyl, benzyl, methylbenzyl, chlorobenzyl, dichlorobenzyl, fluorobenzyl, trifluoromethylbenzyl, nitrobenzyl, methoxyphenyl, N-methylaminobenzyl, N,N-dimethylaminobenzyl, phenacyl, trityl, 1-ethoxyethyl (EE), tetrahydropyranyl (THP), tetrahydrofuryl, propargyl, trimethylsilyl (TMS), triethylsilyl (TES), t-butyldimethylsilyl (TBDMS), t-butyldiphenylsilyl(TBDPS), acetyl (Ac), pivaloyl, benzoyl, allyloxycarbonyl (Alloc), 2,2,2-trichloroethoxycarbonyl (Troc) and the like.

Examples of the protective groups for alkynyl include trimethylsilyl, 2-hydroxy-2-propyl and the like.

Examples of the protective groups for amino group include, for example, benzyl, methylbenzyl, chlorobenzyl, dichlorobenzyl, fluorobenzyl, trifluoromethylbenzyl, nitrobenzyl, methoxyphenyl, N-methylaminobenzyl, N,N-dimethylaminobenzyl, phenacyl, acetyl group, trifluoroacetyl, pivaloyl, benzoyl, allyloxycarbonyl, 2,2,2-trichloroethoxycarbonyl, benzyloxycarbonyl, t-butoxycarbonyl (Boc), 1-methyl-1-(4-biphenyl)ethoxycarbonyl (Bpoc), 9-fluorenylmethoxycarbonyl, benzyloxymethyl (BOM), 2-(trimethylsilyl)ethoxymethyl (SEM) and the like.

By removing these protective groups simultaneously with the preparation or stepwise during the preparation process or at the final step, protected compounds can be converted into objective compounds. The protection and deprotection reactions can be performed according to known methods such as the methods described in, for example, Protective Groups in Organic Synthesis, published by John Wiley and Sons (2007) and the like, and they can be performed by, for example, the methods of (1) to (6) mentioned below and the like.

(1) The deprotection reaction by alkali hydrolysis is performed by, for example, reacting a protected compound with a base in a polar solvent. Examples of the base used in this reaction include, for example, alkali metal bases such as sodium hydroxide, potassium hydroxide, lithium hydroxide, barium hydroxide, calcium hydroxide, sodium carbonate, potassium carbonate, sodium methoxide, and potassium t-butoxide, and organic bases such as triethylamine. For example, they are usually used in an amount of 1 to 20 fold moles, preferably 1 to 10 fold moles, based on the reactant, when an alkali metal base is used, or 1 fold mole to a large excess amount, when an organic base is used. As for the reaction solvent, it is usually preferred that the reaction is performed in an inactive medium that does not inhibit the reaction, preferably a polar solvent. Examples of the polar solvent include water, methanol, ethanol, tetrahydrofuran, dioxane and the like, and these can be used as a mixture as required. As the reaction temperature, a suitable temperature, for example, from −10° C. to the reflux temperature of the solvent, is chosen. The reaction time is, for example, usually 0.5 to 72 hours, preferably 1 to 48 hours, when an alkali metal base is used, or usually 5 hours to 14 days, when an organic base is used. However, the progress of the reaction can be monitored by thin layer chromatography (TLC), high performance liquid chromatography (HPLC) or the like, and accordingly, the reaction may usually be terminated when the maximum yield of the objective compound is obtained.

(2) The deprotection reaction under an acidic condition is performed, for example, in an organic solvent (dichloromethane, chloroform, dioxane, ethyl acetate, anisole and the like) in the presence of an organic acid (acetic acid, trifluoroacetic acid, methanesulfonic acid, p-toluenesulfonic acid and the like), a Lewis acid (boron tribromide, boron trifluoride, aluminum bromide, aluminum chloride and the like), or an inorganic acid (hydrochloric acid, sulfuric acid and the like), or a mixture thereof (hydrogen bromide/acetic acid and the like) at a temperature of −10 to 100° C. There is also a method of adding ethanethiol, 1,2-ethanedithiol or the like as an additive.

(3) The deprotection reaction by hydrogenolysis is performed, for example, in a solvent [ether type solvents (tetrahydrofuran, dioxane, dimethoxyethane, diethyl ether and the like), alcohol type solvents (methanol, ethanol and the like), benzene type solvents (benzene, toluene and the like), ketone type solvents (acetone, methyl ethyl ketone and the like), nitrile type solvents (acetonitrile and the like), amide type solvents (dimethylformamide and the like), ester type solvents (ethyl acetate and the like), water, acetic acid, mixtures of two or more types of those solvents and the like] in the presence of a catalyst (palladium/carbon powder, platinum oxide ($PtO_2$), activated nickel and the like) and a hydrogen source such as hydrogen gas of ordinary pressure or under pressurization, ammonium formate, or hydrazine hydrate at a temperature of −10 to 60° C.

(4) The deprotection reaction of silyl group is performed, for example, by using tetra-n-butylammonium fluoride or the like in a water-miscible organic solvent (tetrahydrofuran, acetonitrile and the like) at a temperature of −10 to 60° C.

(5) The deprotection reaction using a metal is performed, for example, in an acidic solvent (acetic acid, buffer of pH 4.2 to 7.2, a mixture of such a solution and an organic solvent such as tetrahydrofuran) in the presence of zinc powder with or without ultrasonication at a temperature of −10 to 60° C.

(6) The deprotection reaction using a metal complex is performed, for example, in an organic solvent (dichloromethane, dimethylformamide, tetrahydrofuran, ethyl acetate, acetonitrile, dioxane, ethanol and the like), water, or a mixture thereof in the presence of a trap reagent (tributyltin hydride, triethylsilane, dimedone, morpholine, diethylamine, pyrrolidine and the like), an organic acid (acetic acid, formic acid, 2-ethylhexanoic acid and the like) and/or an organic acid salt (sodium 2-ethylhexanoate, potassium 2-ethylhexanoate and the like) in the presence or absence of a phosphine type regent (triphenylphosphine and the like) by using a metal complex [tetrakistriphenylphosphine palladium(0), bis(triphenylphosphine)palladium(II) dichloride, palladium(II) acetate, tris(triphenylphosphine) rhodium(I) chloride and the like] at a temperature of −10 to 60° C.

The compounds of the present invention represented by the formula (1) can be prepared, for example, according to the following reaction pathways. In the following schemes, "STEP" means each step, for example, "STEP 1-1" means Step 1-1.

Step 1-1

[Formula 63]

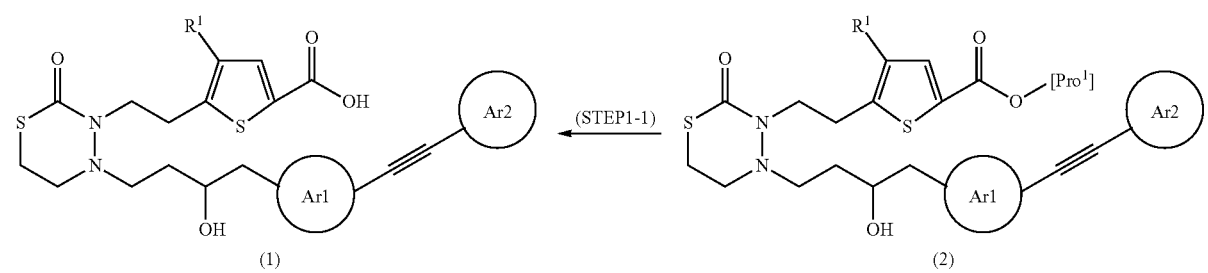

The compounds represented by the formula (1) can be prepared by deprotection of a compound represented by the formula (2) [in the formula (2), "Pro" represents a protective group of carboxyl in the formula (1)] for the protective group Pro¹. The deprotection reaction can be carried out according to known methods, for example, the methods described in Protective Groups in Organic Synthesis, published by John Wiley and Sons (2007) and the like.

Pro¹ is not particularly limited so long as it is the protective group of carboxyl mentioned above, and examples thereof include, for example, an alkyl having 1 to 4 carbon atoms.

[Formula 64]

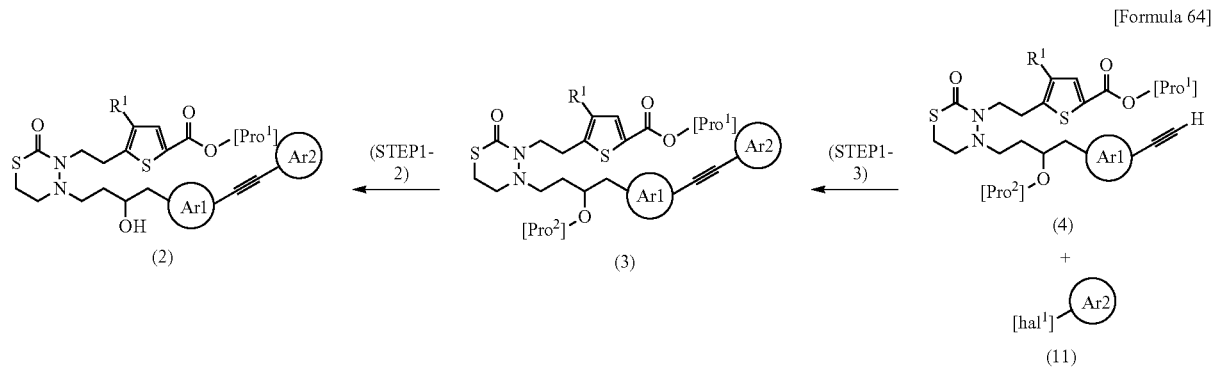

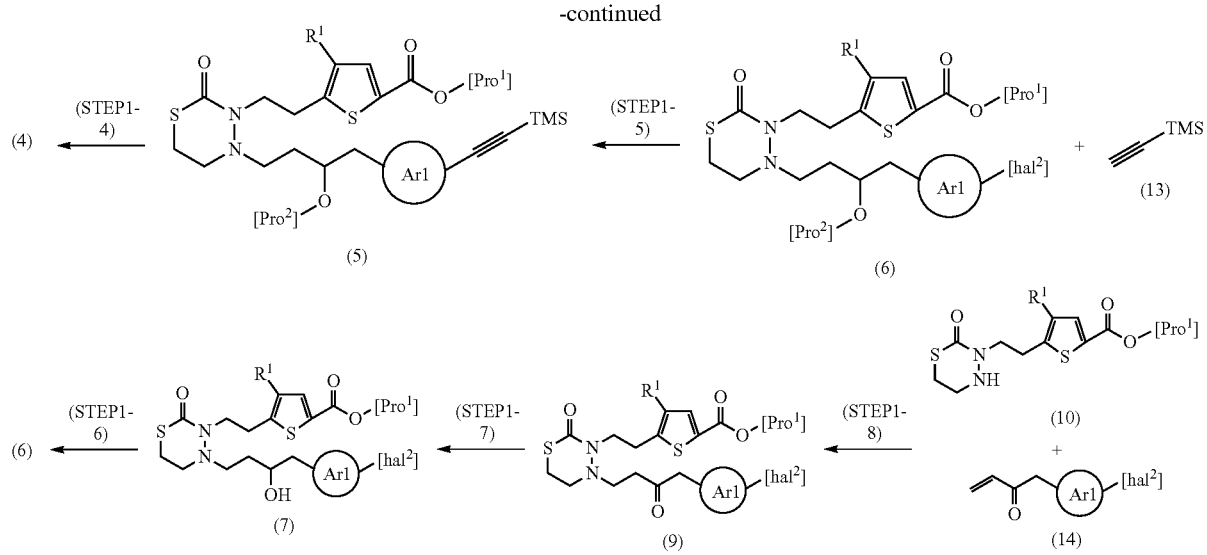

Step 1-2

The compounds represented by the formula (2) can be prepared by deprotection of a compound represented by the formula (3) [in the formula (3), "Pro²" represents a protective group of hydroxyl group in the formula (1), and "Pro¹" has the same meaning as that defined above] for the protective group of the compound represented by the formula (3). The deprotection reaction can be carried out according to known methods, for example, the methods described in Protective Groups in Organic Synthesis, published by John Wiley and Sons (2007) and the like.

Although Pro² is not particularly limited so long as it is the aforementioned protective group of hydroxyl group, Pro² is preferably a group other than TMS in order to selectively perform deprotection for Pro² with respect to TMS in the formula (5). Examples of Pro² include, for example, tert-butyl group, MOM group, MEM group, THP group, acetyl group, and TBDMS group.

Step 1-3

The compounds represented by the formula (3) can be prepared by coupling a compound represented by the formula (4) [in the formula (4), "Pro¹" and "Pro²" have the same meanings as those defined above], and a compound represented by the formula (11) [in the formula (11), "hal¹" represents bromo or iodo] in the presence of a base and a palladium catalyst. As for the amount of the compound represented by the formula (11) used in the reaction of the compound represented by the formula (4) and the compound represented by the formula (11), ⅕ to 20 equivalents, preferably ½ to 10 equivalents, more preferably 1 to 5 equivalents of the compound represented by the formula (11) can be used with respect to the compound represented by the formula (4). However, the amount of the compound represented by the formula (11) to be used can be appropriately determined in consideration of purity, yield, purification efficiency and the like of the compound represented by the formula (4).

As the base, for example, cesium carbonate, sodium carbonate, potassium carbonate and the like can be used, and cesium carbonate is preferred. As for the amount of the base to be used, it can be used in an amount of from equivalent amount to excess amount, for example, 1 to 10 equivalents, preferably 1 to 5 equivalents, with respect to the compound represented by the formula (4), which serves as the starting material.

As the palladium catalyst, for example, marketed catalysts such as tetrakis(triphenylphosphine)palladium, tetrakis(m-ethyldiphenylphosphine)palladium, dichlorobis(triphenylphosphine)palladium, dichlorobis(tri-o-tolylphosphine) palladium, dichlorobis(tricyclohexylphosphine)palladium, dichlorobis(triethylphosphine)-palladium, palladium acetate, palladium chloride, bis(acetonitrile)palladium chloride, bis(dibenzylideneacetone)palladium, tris(dibenzylideneacetone)dipalladium, and bis(diphenylphosphinoferrocene)palladium chloride may be added to the reaction system as they are, or a catalyst separately prepared from palladium acetate, tris(dibenzylideneacetone)dipalladium or the like, and an arbitrary ligand, and isolated may be added. A catalyst considered to actually participate in the reaction may be prepared in the reaction system by mixing palladium acetate, tris(dibenzylidene-acetone)dipalladium or the like, and an arbitrary ligand. The valence of palladium may be 0 or +2. In particular, bis(acetonitrile)palladium chloride can be mentioned as a preferred example.

As the ligand used for preparing a palladium catalyst from an arbitrary ligand, there are exemplified phosphine ligands such as triphenylphosphine, tri(o-tolyl)-phosphine, tri(cyclohexyl)phosphine, tri(t-butyl)phosphine, dicyclohexylphenylphosphine, 1,1'-bis(di-t-butylphosphino)ferrocene, 2-dicyclohexylphosphino-2'-dimethylamino-1,1'-biphenyl, 2-(di-t-butylphosphino)biphenyl, 2-(dicyclohexyl-phosphino)biphenyl, 2,2'-bis(diphenylphosphino)-1,1'-binaphthyl, xantphos, and tri(tert-butyl)phosphine. There are also exemplified 2-dicyclohexylphosphino-2',6'-dimethoxybiphenyl, 2-dicyclohexylphosphino-2',4',6'-triisopropylbiphenyl, 1,2,3,4,5-pentamethyl-1'-(di-t-butylphosphino)ferrocene) and the like, and 2-dicyclohexyl-2',4',6'-triisopropylbiphenyl can be preferably mentioned.

Although the amount in equivalence of the palladium catalyst to be used may be an equivalent amount or catalytic amount, it is preferably 0.01 mol % or more, more preferably, especially 0.10 to 50.0 mol %, based on the amount of the starting compound. Examples of the solvent used for the reaction include, for example, N,N-dimethylformamide, N,N-dimethylacetamide, acetonitrile, xylene, toluene, 1,4-dioxane, and tetrahydrofuran, and preferred examples include acetonitrile. Two or more kinds of these solvents can also be used as a mixture. As for the reaction temperature, the reaction can be performed usually at −40 to 100° C., preferably at −20° C. to 60° C. Although the reaction time is not particularly limited, it is, for example, usually 0.5 to 48 hours, preferably 1 to 24 hours.

Step 1-4

The compounds represented by the formula (4) can be prepared by selective deprotection of TMD of a compound represented by the formula (5) [in the formula (5), "Pro$^1$" and "Pro$^2$" have the same meanings as those defined above]. The deprotection reaction can be carried out according to known methods, for example, the methods described in Protective Groups in Organic Synthesis, published by John Wiley and Sons (2007) and the like.

Specifically, the compounds can be prepared by, for example, allowing an inorganic base to act on a compound represented by the formula (5) in an organic solvent. As the inorganic base, for example, sodium hydroxide, potassium hydroxide, cesium carbonate, sodium carbonate, potassium carbonate or the like can be used, and potassium carbonate is preferred. As for the amount of the base to be used, the base can be used in an amount of from equivalent amount to excess amount with respect to the compound represented by the formula (5), which serves as a starting material, and the amount is, for example, 1 to 10 equivalents, preferably 1 to 5 equivalents. Examples of the solvent used for the reaction include methanol and ethanol, and preferred examples include methanol. As for the reaction temperature, the reaction can be performed usually at −20 to 60° C., preferably at 0 to 40° C. Although the reaction time is not particularly limited, it is, for example, usually 0.5 to 48 hours, preferably 1 to 24 hours.

Step 1-5

The compounds represented by the formula (5) can be prepared by coupling a compound represented by the formula (6) [in the formula (6), "Pro$^1$" and "Pro$^2$" have the same meanings as those defined above, and "hal$^2$" represents bromo or iodo] with a compound represented by the formula (13) in an organic solvent in the presence of an inorganic base. The compounds can be prepared in the same manner as that of the Step 1-3. In this preparation, the compound represented by the formula (13) can be used in an amount of ⅕ to 20 equivalents, preferably ½ to 10 equivalents, more preferably 1 to 5 equivalents, with respect to the compound represented by the formula (6).

Step 1-6

The compounds represented by the formula (6) can be prepared by protecting the hydroxyl group of a compound represented by the formula (7) [in the formula (7), "Pro$^1$" and "hal$^2$" have the same meanings as those defined above]. The protection reaction for hydroxyl group can be carried out according to known methods, for example, the methods described in Protective Groups in Organic Synthesis, published by John Wiley and Sons (2007) and the like. Although the protective group of hydroxyl group is not particularly limited so long as the aforementioned protective group of hydroxyl group is chosen, for example, tert-butyl group, MOM group, MEM group, THP group, acetyl group, TBDMS group and the like can be used.

Step 1-7

The compounds represented by the formula (7) can be prepared by allowing a reducing agent to act on a compound represented by the formula (9) [in the formula (9), "Pro$^1$" and "hal$^2$" have the same meanings as those defined above] in an organic solvent. As the reducing agent, for example, sodium borohydride, lithium borohydride, triacetoxyborohydride, cyanoborohydride and the like can be used, and sodium borohydride is preferred. As for the amount of the reducing agent to be used, it can be used in an amount of ¼ equivalent to excess amount with respect to the compound represented by the formula (9), which serves as the starting material, and the amount is, for example, ¼ to 10 equivalents, preferably 1 to 5 equivalents. Examples of the organic solvent used for the reaction include methanol, ethanol, isopropanol, and a mixed solvent of these with tetrahydrofuran, and preferred examples include methanol. As for the reaction temperature, the reaction can be performed usually at −20 to 60° C., preferably at 0 to 40° C. Although the reaction time is not particularly limited, it is, for example, usually 0.5 to 48 hours, preferably 1 to 24 hours.

Step 1-8

The compounds represented by the formula (9) can be prepared by allowing a compound represented by the formula (14) [in the formula (14), "hale" has the same meaning as that defined above] to act on a compound represented by the formula (10) [in the formula (10), "Pro$^1$" has the same meaning as that defined above]. As for the amount of the compound represented by the formula (14) to be used, it can be used in an amount of from equivalent amount to excess amount with respect to the compound represented by the formula (10), which serves as the starting material, and the amount is, for example, equivalent amount to 10 equivalents, preferably 1 to 5 equivalents. Examples of the solvent used for the reaction include methanol, ethanol, isopropanol, and a mixed solvent of these with water, and preferred examples include ethanol. As for the reaction temperature, the reaction can be performed usually at 0 to 120° C., preferably at 40 to 100° C. Although the reaction time is not particularly limited, it is, for example, usually 0.5 to 48 hours, preferably 1 to 24 hours.

Step 1-9

[Formula 65]

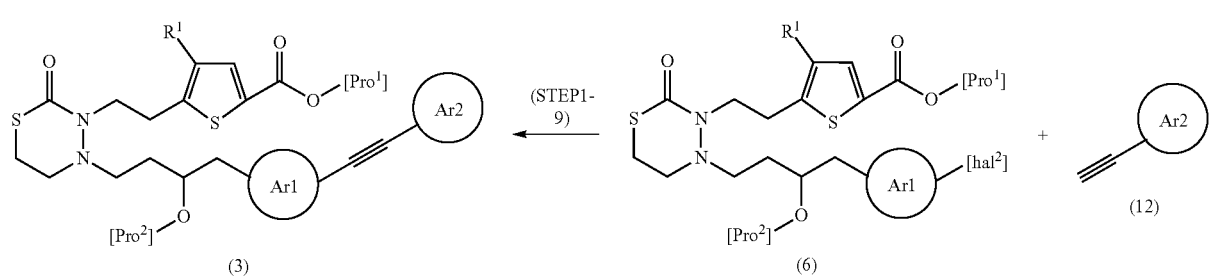

The compounds represented by the formula (3) may also be prepared from a compound represented by the formula (6) [in the formula (6), "Pro¹", "Pro²", and "hal²" have the same meanings as those defined above], and a compound represented by the general formula (12) in the same manner as that of the method of Step 1-3. As for the amount of the compound represented by the formula (12) used in this case, it can be used in an amount of ⅕ to 20 equivalents, preferably ½ to 10 equivalents, more preferably 1 to 5 equivalents, with respect to the compound represented by the formula (6).

Step 1-10 eridine, pyridine and the like can be used, and diester amines are preferred. As for the amount of the base to be used, it can be used in an amount of from equivalent amount to excess amount, for example, 1 to 10 equivalents, preferably 1 to 5 equivalents, with respect to the compound represented by the formula (9), which serves as the starting material.

Examples of the copper catalyst include, for example, copper(I) iodide, copper(I) bromide, copper(I) chloride and the like, and copper(I) iodide is preferred.

Although the amount in equivalence of the copper catalyst to be used may be an equivalent amount or catalytic amount,

[Formula 66]

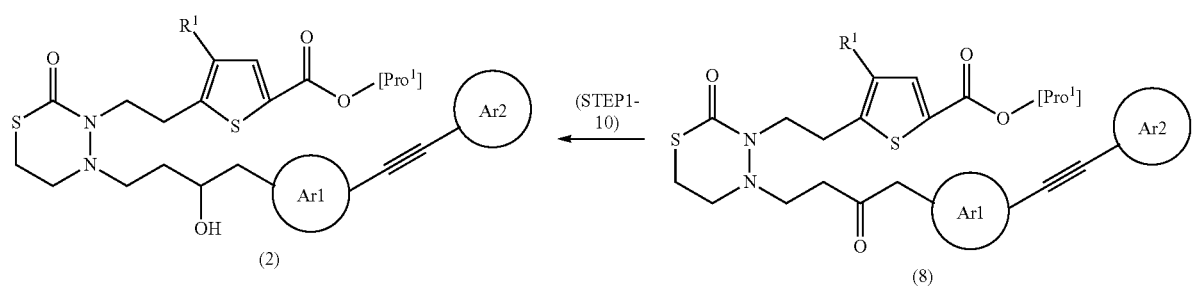

The compounds represented by the formula (2) may also be prepared from a compound represented by the formula (8) [in the formula (8), "Pro¹" has the same meaning as that defined above] in the same manner as the method of Step 1-7.

Step 1-11 it is preferably 0.01 mol % or more, particularly preferably 0.10 to 50.0 mol %, based on the starting material compound.

As the palladium catalyst, for example, marketed catalysts such as tetrakis(triphenylphosphine)palladium, tetrakis(methyldiphenylphosphine)palladium, dichlorobis(triph-

[Formula 67]

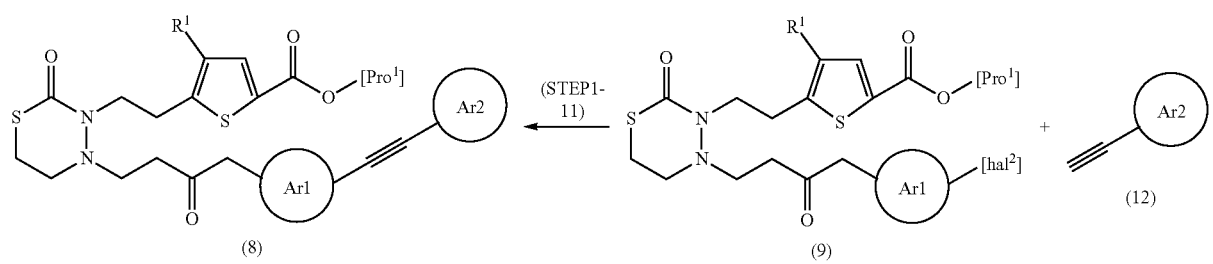

The compounds represented by the formula (8) are prepared by coupling a compound represented by the formula (9) wherein "hal²" is iodine atom [in the formula (9), "Pro¹" has the same meaning as that defined above], and a compound represented by the formula (12) in the presence of a base, a copper catalyst, and a palladium catalyst. As for the amount of the compound represented by the formula (12) used in the reaction of the compound represented by the formula (9), and the compound represented by the formula (12), it can be used in an amount of ⅕ to 20 equivalents, preferably ½ to 10 equivalents, more preferably 1 to 5 equivalents, with respect to the compound represented by the formula (9), but it may be appropriately determined in consideration of purity, yield, purification efficiency and the like of the compound represented by the formula (8).

As the base, for example, triethylamine, diethylamine, diisopropylamine, diisopropylethylamine, morpholine, pipenylphosphine)palladium, dichlorobis(tri-o-tolylphosphine) palladium, dichlorobis(tricyclohexylphosphine)palladium, dichlorobis(triethylphosphine)-palladium, palladium acetate, palladium chloride, bis(acetonitrile)palladium chloride, bis(dibenzylideneacetone)palladium, tris(dibenzylideneacetone)dipalladium, and bis(diphenylphosphinoferrocene)palladium chloride may be added to the reaction system as they are, or a catalyst separately prepared from palladium acetate, tris(dibenzylideneacetone)dipalladium or the like, and an arbitrary ligand and isolated may be added. A catalyst considered to actually participate in the reaction may be prepared in the reaction system by mixing palladium acetate, tris(dibenzylidene-acetone)dipalladium or the like, and an arbitrary ligand. The valence of palladium may be 0 or +2. In particular, tetrakis(triphenylphosphine)palladium can be mentioned as a preferred example. When the palladium catalyst is prepared from an arbitrary ligand, the same ligands as the ligands exemplified for Step 1-3 can be used.

Although the amount in equivalence of the palladium catalyst to be used may be equivalent amount or a catalytic amount, it is preferably 0.01 mol % or more, more preferably, especially 0.10 to 50.0 mol %, based on the starting material compound.

Examples of the solvent used for the reaction include, for example, N,N-dimethylformamide, N,N-dimethylacetamide, acetonitrile, xylene, toluene, 1,4-dioxane, tetrahydrofuran and the like, or the reaction can also be performed without solvent. The reaction performed without solvent is a preferred example. As for the reaction temperature, the reaction can be performed usually at −40 to 100° C., preferably at −20 to 60° C. Although the reaction time is not particularly limited, it is, for example, usually 0.5 to 48 hours, preferably 1 to 24 hours.

Step 1-12

[Formula 68]

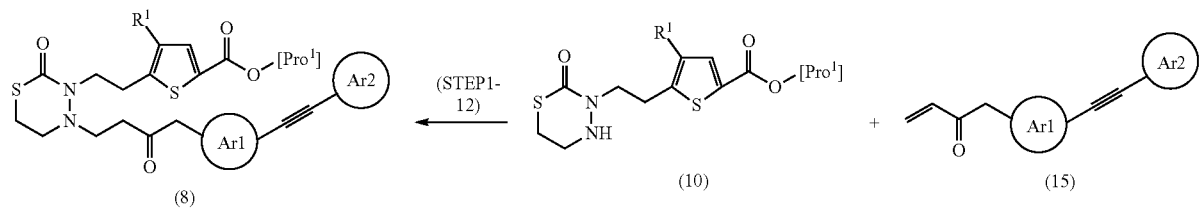

The compounds represented by the formula (8) may also be prepared from a compound represented by the formula (10) [in the formula (10), "Pro$^1$" has the same meaning as that defined above], and a compound represented by the formula (15) in the same manner as that of Step 1-8.

[Formula 69]

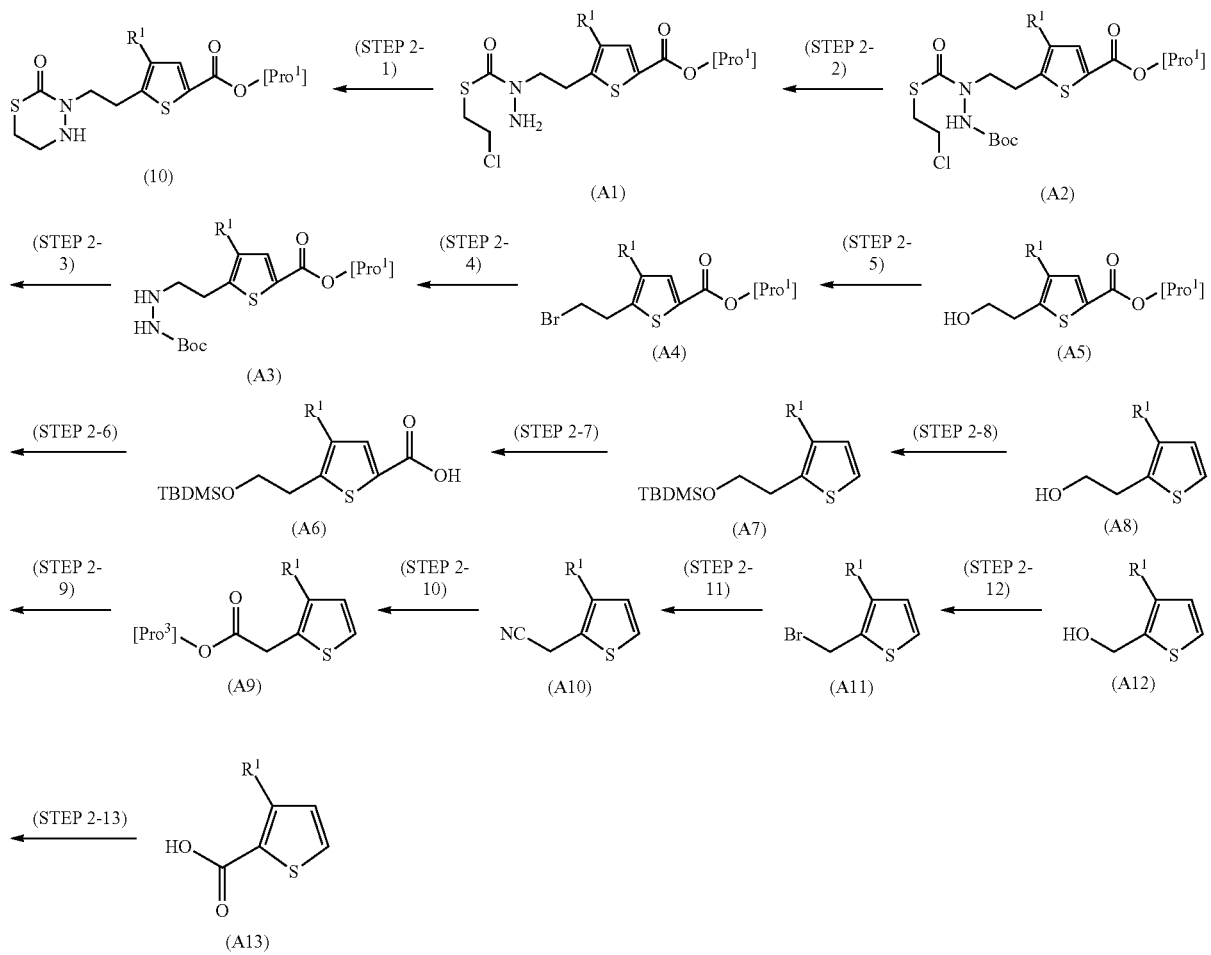

Step 2-1

The compounds represented by the formula (10) can be prepared by allowing a base to act on a compound represented by the formula (A1) [in the formula (A1), "Pro$^1$" has the same meaning as that defined above] in an organic solvent. As the base, for example, sodium hydroxide, potassium hydroxide, cesium carbonate, sodium carbonate, sodium hydrogencarbonate, potassium carbonate and the like can be used, and sodium hydrogencarbonate is preferred. The base can be used in an amount of equivalent amount to an excess amount, for example, 1 to 20 equivalents, preferably 1 to 10 equivalents, with respect to the compound represented by the formula (10), which serves as the starting material. Sodium iodide can be used as an additive, and can be used in an amount of equivalent amount to an excess amount, for example, 1 to 10 equivalents, preferably 1 to 5 equivalents, with respect to the compound represented by the formula (10), which serves as the starting material. Examples of the organic solvent used for the reaction include N,N-dimethylformamide, N,N-dimethylacetamide, acetonitrile, toluene, tetrahydrofuran, 1,4-dioxane, diethyl ether, and mixed solvents of these, and preferred examples include acetonitrile. As for the reaction temperature, the reaction can be performed usually at 0 to 100° C., preferably at 20 to 60° C. Although the reaction time is not particularly limited, it is, for example, usually 0.5 to 48 hours, preferably 1 to 24 hours.

Step 2-2

The compounds represented by the formula (A1) can be prepared by deprotection of a compound represented by the formula (A2) [in the formula (A2), "Pro" has the same meaning as that defined above] for the protective group. The deprotection reaction can be carried out according to known methods, for example, the methods described in Protective Groups in Organic Synthesis, published by John Wiley and Sons (2007) and the like.

Step 2-3

The compounds represented by the formula (A2) can be prepared by allowing a chlorothioformic acid ester such as 2-chloroethyl chlorothioformate to act on a compound represented by the formula (A3) [in the formula (A3), "Pro" has the same meaning as that defined above] in the presence of a base. The chlorothioformic acid ester can be used in an amount of from equivalent amount to excess amount, for example, 1 to 5 equivalents, preferably 1 to 2 equivalents, with respect to the compound represented by the formula (A2), which serves as the starting material. As the base to be used, for example, sodium carbonate, potassium carbonate, sodium hydrogencarbonate, cesium carbonate, sodium hydroxide, diisopropylethylamine, triethylamine and the like can be used, and sodium hydrogencarbonate is preferred. Examples of the solvent used for the reaction include dichloromethane, toluene, tetrahydrofuran, 1,4-dioxane, acetonitrile and the like, and dichloromethane is preferred. As for the reaction temperature, the reaction can be performed at 0 to 100° C., preferably at 10 to 30° C. Although the reaction time is not particularly limited, it is, for example, usually 1 to 24 hours, preferably 2 to 4 hours.

Step 2-4

The compounds represented by the formula (A3) can be prepared by allowing t-butoxycarbonylhydrazine to act on a compound represented by the formula (A4) [in the formula (A4), "Pro$^1$" has the same meanings as that defined above] in the presence of a base. As the base to be used, for example, sodium carbonate, potassium carbonate, sodium hydrogencarbonate, cesium carbonate, sodium hydroxide, diisopropylethylamine, triethylamine and the like can be used, and sodium hydrogencarbonate is preferred. The amount of the base to be used is, for example, 1 to 20 equivalents, preferably 3 to 5 equivalents, with respect to the compound represented by the formula (A4), which serves as the starting material. Sodium iodide or the like can be used as an additive. Examples of the solvent used for the reaction include acetonitrile, propionitrile, N,N-dimethylformamide, dimethyl sulfoxide, N-methylpyrrolidone and the like can be used, and preferred examples include acetonitrile. As for the reaction temperature, the reaction can be performed usually at room temperature to 150° C., preferably at 70° C. to 100° C. Although the reaction time is not particularly limited, it is, for example, 3 to 36 hours, preferably 3 to 18 hours.

Step 2-5

The compounds represented by the formula (A4) can be prepared by substituting bromine atom for the hydroxyl group of a compound represented by the formula (A5) [in the formula (A5), "Pro$^1$" has the same meaning as that defined above]. The reaction for substituting bromine atom can be performed by allowing carbon tetrabromide, N-bromosuccinimide or the like to act on the compound in the presence of triphenylphosphine or the like. The amount of triphenylphosphine to be used is, for example, 1 to 5 equivalents, preferably 1 to 2 equivalents, with respect to the compound represented by the formula (A5), which is the starting material. The amount of carbon tetrabromide or the like to be used is, for example, 1 to 5 equivalents, preferably 1 to 2 equivalents, with respect to the compound represented by the formula (A5), which is the starting material. Examples of the solvent used for the reaction include dichloromethane, toluene, tetrahydrofuran, 1,4-dioxane, acetonitrile and the like, and dichloromethane is preferred. As for the reaction temperature, the reaction can be performed usually at −20 to 40° C., preferably at −10 to 10° C. Although the reaction time is not particularly limited, it is, for example, usually 3 to 36 hours, preferably 12 to 20 hours.

Step 2-6

The compounds represented by the formula (A5) can be prepared by deprotection of a compound represented by the formula (6A) for the protective group of the hydroxyl group. The deprotection can be carried out according to known methods, for example, the methods described in Protective Groups in Organic Synthesis, published by John Wiley and Sons (2007) and the like.

Step 2-6

The compounds represented by the formula (A5) can be prepared by converting the carboxylic acid of a compound represented by the formula (A6) into ester, and performing deprotection to remove the protective group of the hydroxyl group. The reaction can be advanced in an alcohol solvent in the presence of an acid. Examples of the acid used for the reaction include sulfuric acid, hydrogen chloride, methanesulfonic acid, p-toluenesulfonic acid, trifluoroacetic acid and the like, and preferred examples include sulfuric acid. As the solvent, methanol, ethanol or the like can be used, and preferred examples include methanol. As for the reaction temperature, the reaction can be performed usually at room temperature to 140° C., preferably at 50 to 80° C. Although the reaction time is not particularly limited, it is, for example, usually 2 to 24 hours, preferably 8 to 16 hours.

Step 2-7

The compounds represented by the formula (A6) can be prepared by allowing a strong base, and then carbon dioxide to act on a compound represented by the formula (A7). As the strong base, lithium amide such as diisopropyl lithium amide or lithium hexamethyl disilazide can be used. When R$^1$ is hydrogen, a lower alkyllithium such as n-butyllithium, s-butyllithium, and n-propyllithium can also be used, and diisopropyl lithium amide is preferably used. The amount of the strong base used is, for example, 1 to 3 equivalents, preferably 1 to 2 equivalents, with respect to the compound represented by the formula (A7), which is the starting material. Examples of the solvent used for the reaction include tetrahydrofuran, diethyl ether, 1,4-dioxane and the like, and tetrahydrofuran is preferred. As for the temperature for the reaction with the strong base, the reaction can be performed usually at −100 to −20° C., preferably at −80 to −60° C. The following reaction with carbon dioxide or the like can usually be performed at −40 to 40° C., and preferably −20 to 10° C. Although the reaction time of the reaction with the strong base is not particularly limited, it is, for example, 0.2 to 3 hour, preferably 0.5 to 1 hours. Although the reaction time of the reaction with carbon dioxide or the like is not particularly limited, it is, for example, usually 0.5 to 24 hours, preferably 0.75 to 2 hours.

Step 2-8

The compounds represented by the formula (A7) can be prepared by protecting the hydroxyl group of a compound represented by the formula (A8) with TBDMS. The protection of the hydroxyl group can be performed by using a method similar to that of Step 1-6.

The compound of the formula (A8) wherein $R^1$ is H is a marketed compound (2-(thiophen-2-yl)ethanol, Tokyo Chemicals). Therefore, when $R^1$ in the formula (A8) is H, the following steps are not required.

Step 2-9

The compounds represented by the formula (A8) can be prepared by reducing the ester group of a compound represented by the formula (A9) [in the formula (A9), "$Pro^3$" represents a protective group of the carboxyl of the compound of the formula (A8)]. That is, as $Pro^3$, for example, alkyl having 1 to 4 carbon atoms can be used.

As the reducing agent, for example, lithium aluminum hydride, diisobutylaluminum hydride, lithium hydride-triethylborane and the like can be used, and lithium aluminum hydride is preferred. The amount of the reducing agent to be used is, for example, 0.5 to 5 mol equivalents, preferably 1 to 2 mol equivalents, with respect to the compound represented by the formula (A9), which serves as the starting material.

Examples of the solvent used for the reaction include tetrahydrofuran, diethyl ether, toluene, and mixed solvents of these, and preferred examples include tetrahydrofuran and diethyl ether. As for the reaction temperature, the reaction can be performed usually at −10 to 20° C., preferably at −5 to 5° C. Although the reaction time is not particularly limited, it is, for example, usually 0.08 to 0.5 hour, preferably 0.15 to 0.3 hour.

Step 2-10

The compounds represented by the formula (A9) can be prepare by, for example, carrying out solvolysis of a compound represented by the formula (A10) in an alcohol in the presence of an acid. As the acid, sulfuric acid, methanesulfonic acid, hydrogen chloride and the like can be used, and sulfuric acid is preferred. The amount of sulfuric acid to be used is, for example, 0.0001 to 0.005 mol equivalent, preferably 0.0002 to 0.001 mol equivalent, with respect to the compound represented by the formula (A10), which serves as the starting material. As the alcohol used as the solvent, for example, ethanol, methanol, n-propanol, n-butyl alcohol, isobutyl alcohol and the like can be used. Although the reaction time is not particularly limited, it is, for example, usually 6 to 48 hours, preferably 16 to 24 hours.

Step 2-11

The compounds represented by the formula (A10) can be prepared by allowing a cyanide to act on a compound represented by the formula (A11). As the cyanide, for example, sodium cyanide, potassium cyanide and the like can be used. The amount of the cyanide to be used is, for example, 1 to 5 equivalents, preferably 1 to 2 equivalents, with respect to the compound represented by the formula (A10), which is the starting material. As the solvent used for the reaction, tetrahydrofuran, acetonitrile, dimethyl sulfoxide, N,N-dimethylacetamide, N,N-dimethylformamide and the like can be used, and preferred examples include a mixed solvent of acetonitrile and dimethyl sulfoxide. As for the reaction temperature, the reaction can be performed usually at 0 to 60° C., preferably 10 to 40° C. Although the reaction time is not particularly limited, it is, for example, usually 0.5 to 20 hours, preferably 2 to 6 hours.

Step 2-12

The compounds represented by the formula (A11) can be prepared by converting the hydroxyl group of a compound represented by the formula (A12) into bromine atom. The conversion into bromine atom may be performed in the same manner as that of Step 2-5.

Step 2-13

The compounds represented by the formula (A12) can be prepared by reducing the carboxyl group of a marketed compound represented by the formula (A13) into hydroxyl group. As the reducing agent, for example, borane-dimethyl sulfide, borane-tetrahydrofuran and the like can be used, and borane-tetrahydrofuran is preferred. The amount of the reducing agent to be used is, for example, 1 to 5 mol equivalents, preferably 1 to 2 mol equivalents, with respect to the compound represented by the formula (A13), which serves as the starting material.

As the solvent used for the reaction, tetrahydrofuran, diethyl ether and the like can be used, and preferred examples include tetrahydrofuran. As for the reaction temperature, the reaction can be performed usually at 0 to 60° C., preferably at 10 to 40° C. Although the reaction time is not particularly limited, it is, for example, usually 4 to 24 hours, preferably 10 to 18 hours.

Examples of the marketed compound represented by the formula (A13) include, for example, 3-chlorothiophene-2-carboxylic acid, 3-bromothiophene-2-carboxylic and the like, and they can be purchased from, for example, Sigma-Aldrich.

Step 3-1

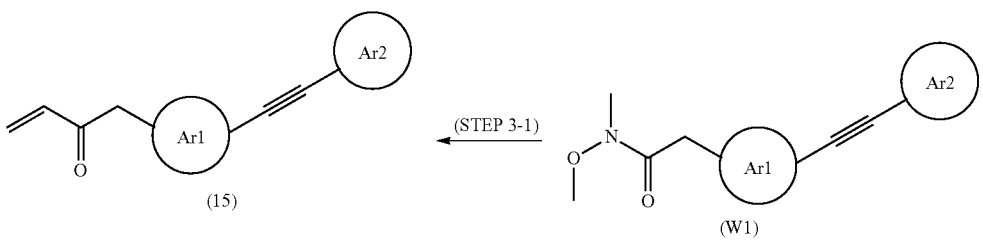

[Formula 70]

The compounds represented by the formula (15) can be prepared by allowing a vinylation regent to act on a compound represented by the formula (W1) in an organic solvent. As the vinylation reagent, for example, vinylmagnesium bromide, vinylmagnesium chloride, vinyllithium and the like can be used, and vinylmagnesium bromide and vinylmagnesium chloride are preferred. Vinylmagnesium bromide and vinylmagnesium chloride can be used as a solution in tetrahydrofuran, diethyl ether, or toluene, and a tetrahydrofuran solution is preferred. As for the amount of the vinylation reagent to be used, the reagent may used in an amount of from equivalent amount to an excess amount, for example, 1 to 10 equivalents, preferably 1 to 5 equivalents, with respect to the compound represented by the formula (W1), which serves as the starting material. Examples of the solvent used for the reaction include toluene, tetrahydrofuran, 1,4-dioxane, diethyl ether, 1,2-dimethoxyethane, and mixed solvents of these, and preferred examples include tetrahydrofuran and 1,2-dimethoxyethane. As for the reaction temperature, the reaction can be performed usually at −78 to 0° C., preferably at −50 to 0° C. Although the reaction time is not particularly limited, it is for example, usually 0.5 to 24 hours, preferably 1 to 12 hours.

Step 3-2

N,O-dimethylhydroxylamine hydrochloride may be equivalent amount to excess amount, for example, 1 to 10 equivalents, preferably 1 to 5 equivalents, with respect to the compound represented by the formula (W3), but the amount can be appropriately determined in consideration of purity, yield, purification efficiency and the like of the compound represented by the formula (W3).

As the base, for example, triethylamine, diisopropylethylamine, 1,4-diazabicyclo[2,2,2]octane, N,N-dimethyl-4-aminopyridine and the like can be used, and diisopropylethylamine is preferred. The amount of the base to be used may be equivalent amount to excess amount, for example, 1 to 10 equivalents, preferably 1 to 5 equivalents, with respect to the sum of the equivalent of the compound represented by the formula (W3), which serves as the starting material, and the equivalent of N,O-dimethylhydroxylamine hydrochloride.

As the dehydration condensation agent, there can be used N,N'-dicyclohexylcarbodiimide, 1-ethyl-3-(3-dimethylaminopropyl)carbodiimide, N,N'-diisopropylcarbodiimide, N-cyclohexyl-N'-(2-morpholinoethyl)carbodiimide p-toluenesulfonate, N,N'-carbonyldiimidazole, 4-(4,6-dimethoxy-1,3,5-triazin-2-yl)-4-methylmorpholinium chloride, 1H-benzotriazol-1-yloxy-tris(dimethylphosphonium)

[Formula 71]

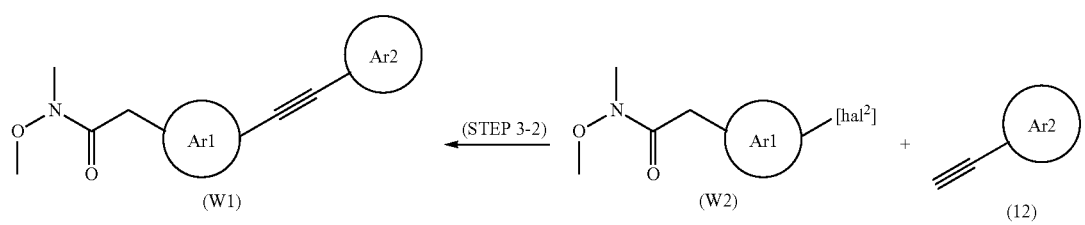

The compounds represented by the formula (W1) can be prepared from a compound represented by the formula (W2) [in the formula (W2), "hal$^2$" has the same meaning as that defined above] and a compound represented by the formula (12) in the same manner as that of Step 1-3. In this reaction, the compound represented by the formula (12) can be used in an amount of ⅕ to 20 equivalents, preferably ½ to 10 equivalents, more preferably 1 to 5 equivalents, with respect to the compound represented by the formula (W2).

Step 3-3

[Formula 72]

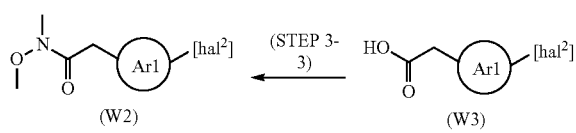

The compounds represented by the formula (W2) can be prepared by reacting a compound represented by the formula (W3) [in the formula (W3), "hal$^2$" has the same meaning as that defined above] with N,O-dimethylhydroxylamine hydrochloride in an organic solvent in the presence of a base and a dehydration condensation agent. The amount of N,O-dimethylhydroxylamine hydrochloride used in the reaction of the compound represented by the formula (W3) and hexafluorophosphate, 1H-benzotriazol-1-yloxy-tripyrrolidinophosphonium hexafluorophosphate, O-(benzotriazol-1-yl)-N,N,N',N'-tetramethyluronium hexafluorophosphate, O-(7-aza-benzotriazol-1-yl)-N,N,N',N'-tetramethyluronium hexafluorophosphate and the like, and 1-ethyl-3-(3-dimethylaminopropyl)carbodiimide is preferred. The amount of the dehydration condensation agent to be used may be equivalent amount to excess amount, for example, 1 to 10 equivalents, preferably 1 to 5 equivalents, with respect to the equivalent of the compound represented by the formula (W3), which serves as the starting material.

As an activator, N,N-dimethyl-4-aminopyridine or the like can be added. The amount of the activator to be used may be a catalytic amount to excess amount, for example, 0.01 to 5 equivalents, preferably 0.1 to 1 equivalent, with respect to the equivalent of the compound represented by the formula (W3), which serves as the starting material.

Examples of the solvent used for the reaction include, for example, N,N-dimethylformamide, N,N-dimethylacetamide, acetonitrile, xylene, toluene, 1,4-dioxane, dichloromethane, chloroform, 1,2-dichloroethane, tetrahydrofuran and the like, and preferred examples include dichloromethane. Two or more kinds of these solvents can also be used as a mixture. As for the reaction temperature, the reaction can be performed usually at 0 to 100° C., preferably at 20 to 60° C. Although the reaction time is not particularly limited, it is, for example, usually 0.5 to 48 hours, preferably 1 to 24 hours.

Step 3-4

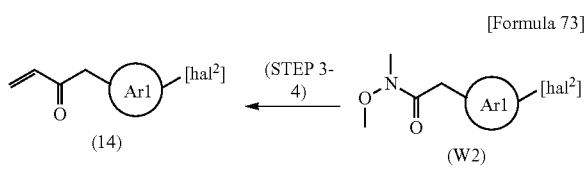
[Formula 73]

The compounds represented by the formula (14) can be prepared from a compound represented by the formula (W2) [in the formula (W2), "hal²" has the same meaning as that defined above] in the same manner as that of the method of the step 3-1.

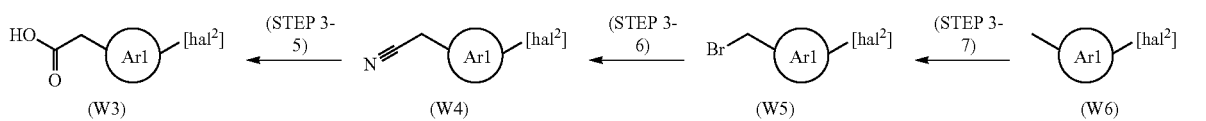
[Formula 74]

Step 3-5

The compounds represented by the formula (W3) can be prepared by heating a compound represented by the formula (W4) [in the formula (W4), "hal²" has the same meaning as that defined above] in diluted sulfuric acid. As the diluted sulfuric acid used for the reaction, appropriately diluted concentrated sulfuric acid or diluted sulfuric acid can be used, and the concentration thereof is, for example, 0.1 to 15 mol/l, preferably 1 to 10 mol/l. The amount of the diluted sulfuric acid to be used can be excess amount for the compound represented by the formula (W4), and it may be determined in consideration of yield, purification efficiency and the like. As for the reaction temperature, the reaction can be performed usually at 20 to 100° C., preferably at 60 to 100° C. Although the reaction time is not particularly limited, it is, for example, usually 0.5 to 48 hours, preferably 1 to 24 hours.

Among the compounds represented by the formula (W3), 3-bromophenylacetic acid, 3-iodophenylacetic acid, and 3-bromo-4-fluorophenylacetic acid are marketed compounds, and can be obtained from Tokyo Chemical Industry. 2-(4-Bromothiophen-2-yl)acetic acid is a marketed compound, and can be obtained from APOLLO.

Step 3-6

The compounds represented by the formula (W4) can be prepared by allowing a cyanide to act on a compound represented by the formula (W5) [in the formula (W5), "hal²" has the same meaning as that defined above]. As the cyanide, sodium cyanide, potassium cyanide, copper cyanide and the like can be used, and sodium cyanide and potassium cyanide are preferred. The amount of the cyanide to be used may be equivalent amount to excess amount, for example, 1 to 10 equivalents, preferably 1 to 5 equivalents, with respect to the compound represented by the formula (W5), which serves as the starting material. Examples of the solvent used for the reaction include, for example, methanol, ethanol, isopropanol, water, mixed solvents of these and the like, and preferred examples include a mixed solvent of ethanol and water at a ratio of 2:1. As for the reaction temperature, the reaction can be performed usually at 0 to 100° C., preferably at 20 to 100° C. Although the reaction time is not particularly limited, it is, for example, usually 0.5 to 24 hours, preferably 1 to 12 hours.

Step 3-7

The compounds represented by the formula (W5) can be prepared by brominating a compound represented by the formula (W6) [in the formula (W6), "hal²" has the same meaning as that defined above]. Examples of the brominating agent include N-bromosuccinimide, and 1,3-dibromo-5,5-dimethylhydantoin, and N-bromosuccinimide is preferred. The amount of the brominating agent to be used may be equivalent amount to excess amount, for example, 1 to 10 equivalents, preferably 1 to 5 equivalents, with respect to the compound represented by the formula (W6), which serves as the starting material. Examples of an activator to be added together with the brominating agent include benzoyl peroxide, tert-butylhydroperoxide, and azobisisobutyronitrile, and benzoyl peroxide is preferred. The amount of the activator to be used may be a catalytic amount to excess amount, for example, 0.01 to 2 equivalents, preferably 0.05 to 1 equivalent, with respect to the compound represented by the formula (W6), which serves as the starting material. Examples of the solvent used for the reaction include, for example, carbon tetrachloride, chloroform, 1,2-dichloroethane, mixed solvents of these and the like, and preferred examples include carbon tetrachloride. As for the reaction temperature, the reaction can be performed usually at 20 to 90° C., preferably at 60 to 90° C. Although the reaction time is not particularly limited, it is, for example, usually 0.5 to 24 hours, preferably 1 to 12 hours.

Examples of the compound represented by the formula (W6) include 2-bromo-1,4-dimethylbenzene, 1-bromo-3,5-dimethylbenzene and the like, and these can be purchased as marketed compounds from, for example, Tokyo Chemical Industry.

Step 3-8

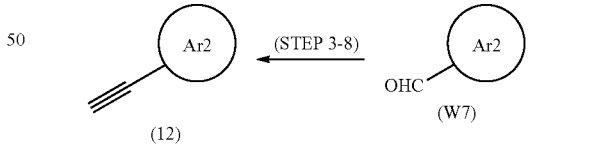
[Formula 75]

The compounds represented by the formula (12) can be prepared by allowing an α-diazophosphonate compound to act on a compound represented by the formula (W7) together with an inorganic base. Examples of the combination of the α-diazophosphonate compound and the inorganic base include, for example, combinations of dimethyl(diazomethyl)phosphonate and potassium tert-butoxide, dimethyl(diazomethyl)phosphonate and sodium tert-butoxide, dimethyl(1-diazo-2-oxopropyl)phosphonate and potassium carbonate, and dimethyl(1-diazo-2-oxopropyl)phosphonate and sodium carbonate, and combination of dimethyl(1-diazo-2-oxopropyl)phosphonate and potassium carbonate is preferred. The amount of the α-diazophosphonate to be used may be equivalent amount to excess amount, for example, 1 to 10 equivalents, preferably 1 to 5 equivalents, with respect to the compound represented by the formula (W7), which serves as the starting material. The amount of the inorganic base to be used may be equivalent amount to excess amount, for example, 1 to 5 equivalents, preferably 1 to 3 equivalents, with respect to the α-diazophosphonate to be used. Examples of the solvent used for the reaction include, for example, methanol, ethanol, isopropanol, tert-butanol, mixed solvents of these and the like, and preferred examples include methanol. As for the reaction temperature, the reaction can be performed usually at −20 to 80° C., preferably at 0 to 60° C. Although the reaction time is not particularly limited, it is, for example, usually 0.5 to 24 hours, preferably 1 to 12 hours.

Among the compounds represented by the formula (12), 3-ethynylthiophene and 2-ethynylthiophene are marketed compounds, and can be obtained from Tokyo Chemical Industry.

Step 3-9

4-Phenylthiophene-3-carboaldehyde as the compound represented by the formula (W7) can be prepared by reacting 4-formylthiophene-3-boronic acid and bromobenzene in a solvent in the presence of a base and a palladium catalyst.

As the palladium catalyst, for example, marketed catalysts such as tetrakis(triphenylphosphine)palladium, tetrakis(m-ethyldiphenylphosphine)palladium, dichlorobis(triphenylphosphine)palladium, dichlorobis(tri-o-tolylphosphine) palladium, dichlorobis(tricyclohexylphosphine)palladium, dichlorobis(triethylphosphine)-palladium, palladium acetate, palladium chloride, bis(acetonitrile)palladium chloride, bis(dibenzylideneacetone)palladium, tris(dibenzylideneacetone)dipalladium, and bis(diphenylphosphinoferrocene)palladium chloride may be added to the reaction system as they are, or a catalyst separately prepared from palladium acetate, tris(dibenzylideneacetone)dipalladium or the like, and an arbitrary ligand, and isolated may be added. A catalyst considered to actually participate in the reaction may be prepared in the reaction system by mixing palladium acetate, tris(dibenzylidene-acetone)dipalladium or the like, and an arbitrary ligand. The valence of palladium may be 0 or +2. In particular, tris(dibenzylideneacetone)dipalladium (0), palladium(II) acetate and the like can be mentioned as preferred examples.

As the ligand used for preparing a palladium catalyst from an arbitrary ligand, there are exemplified phosphine ligands such as triphenylphosphine, tri(o-tolyl)phosphine, tri(cyclohexyl)phosphine, tri(t-butyl)phosphine, dicyclohexyl-phenylphosphine, 1,1'-bis(di-t-butylphosphino)ferrocene, 2-dicyclohexylphosphino-2'-dimethylamino-1,1'-biphenyl, 2-(di-t-butylphosphino)biphenyl, 2-(dicyclohexyl-phosphino)biphenyl, 2,2'-bis(diphenylphosphino)-1,1'-binaphthyl, xantphos, tri(tert-butyl)phosphine, 2-dicyclohexylphosphino-2',6'-dimethoxybiphenyl, 2-dicyclohexyl-2',4',6'-triisopropylbiphenyl, and 1,2,3,4,5-pentamethyl-1'-(di-t-butylphosphino)-ferrocene), and preferred examples include 2-dicyclohexylphosphino-2',6'-dimethoxybiphenyl and the like.

Although the equivalent number of the palladium catalyst to be used may be equivalent amount or a catalytic amount, it is preferably 0.01 mol % or more, particularly preferably 0.10 to 50.0 mol %, based on the starting material compound. Examples of the base include, for example, sodium tert-butoxide, cesium carbonate, potassium phosphate and the like, and potassium phosphate is preferred. The equivalent number of the base to be used may be equivalent amount or excess amount, for example, 1 to 5 equivalents, preferably 1 to 3 equivalents. Examples of the solvent used for the reaction include, for example, ether type solvents such as tetrahydrofuran, 1,4-dioxane, and 1,2-dimethoxyethane, toluene, N,N-dimethylformamide, N,N-dimethylacetamide, n-butanol, water, mixed solvents of these and the like, and a mixed solvent of n-butanol and water at a ratio of 5:1 can be mentioned as a preferred example. As for the reaction temperature, the reaction can be performed usually at −20 to 120° C., preferably at 0 to 100° C. Although the reaction time is not particularly limited, it is, for example, usually 0.5 to 48 hours, preferably 1 to 24 hours.

The preparation methods of the compounds of the present invention are not limited to the methods described herein. For example, the compounds of the present invention can be prepared by modifying or converting substituents of compounds as precursors of the compounds of the present invention using one or a combination of two or more of reactions described in ordinary chemical articles and the like.

Examples of the preparation method for the compounds of the present invention which contain an asymmetric carbon include a preparation method based on asymmetric reduction, a method of using a commercially available starting material (or starting material that can be prepared by a known method or a method similar to a known method) of which moiety corresponding to the asymmetric carbon is originally optically active and the like. A method is also available in which a compound of the present invention or a precursor thereof is separated as an optically active isomer by a conventional method. Examples of such a method include, for example, a method utilizing high performance liquid chromatography (HPLC) using a chiral column, the classical fractional crystallization for separation of optically active substances comprising formation of a salt with an optically active regent, separation by fractional crystallization or the like, and conversion of the salt into a compound of free form, a method comprising condensation with an optically active regent to form a diastereomer, followed by separation, purification, and decomposition of the produced diastereomer and the like. When a precursor is separated to obtain an optically active substance, an optically active compound of the present invention can then be prepared by performing the aforementioned preparation methods.

When a compound of the present invention contains an acidic functional group such as carboxyl group, phenolic hydroxyl group, or tetrazole ring, the compound can be converted into a pharmaceutically acceptable salt (e.g., inorganic salts with sodium and the like, or organic salts with triethylamine and the like) by a known means. For example, when an inorganic salt is to be obtained, it is preferable to dissolve the compound of the present invention in water containing at least 1 equivalent of hydroxide, carbonate, bicarbonate or the like corresponding to the desired inorganic salt. For the reaction, a water-miscible inactive organic solvent such as methanol, ethanol, acetone, and dioxane may be mixed. For example, by using sodium hydroxide, sodium carbonate, or sodium hydrogencarbonate, a solution of sodium salt can be obtained.

When a compound of the present invention contains amino group, another basic functional group, or an aromatic ring which itself has a basic property (e.g., pyridine ring and the like), the compound can also be converted into a pharmaceutically acceptable salt (e.g., salt with an inorganic acid such as hydrochloric acid, or salt with an organic acid such as acetic acid) by a known means. For example, when a salt with an inorganic acid is to be obtained, it is preferable to dissolve the compound of the present invention in water containing at least 1 equivalent of a desired inorganic acid. For the reaction, a water-miscible inactive organic solvent such as methanol, ethanol, acetone, and dioxane may be mixed. For example, by using hydrochloric acid, a solution of hydrochloride can be obtained.

If a solid salt is desired, the solution may be evaporated, or a water-miscible organic solvent having polarity to some extent, such as n-butanol or ethyl methyl ketone, can be added to the solution to obtain a solid salt.

The various compounds disclosed by the present invention can be purified by known methods such as variety of chromatography techniques (column chromatography, flash column chromatography, thin layer chromatography, high performance liquid chromatography).

The compounds of the present invention according to a certain embodiment have an $EP_4$ agonist activity, and can be used as $EP_4$ agonist. That is, the compounds of the present invention according to a certain embodiment can be used as a medicament for prophylactic and/or therapeutic treatment of a disease relating to $EP_4$ receptor agonization. The disease relating to $EP_4$ receptor agonization is, more precisely, a disease for which $EP_4$ receptor agonization is effective, and more specifically, it is not particularly limited so long as it is a disease that can be prevented and/or treated by raising the cAMP production amount in osteoblasts.

The $EP_4$ agonist activity can be measured by, for example, the methods described below. That is, a method of confirming promotion of the cAMP production in a human $EP_4$ receptor-expressing cell can be mentioned. As another embodiment, a method of confirming osteogenesis-promoting action based on promotion of cAMP production in the presence of cyclooxygenase 2 (COX-2) inhibitor in rat marrow cells can be mentioned. As still another embodiment, a method of confirming activity of binding to the human $EP_4$ receptor can be mentioned. As the method for confirming osteogenesis-promoting action based on promotion of the cAMP production, specifically, the method described in Test Examples 1 mentioned later can be exemplified.

The $EP_4$ agonist activity that can be confirmed by the method described in Test Example 1 is, for example, 10 nM or lower, preferably 1 nM or lower, more preferably 0.6 nM or lower, still more preferably 0.3 nM or lower, particularly preferably 0.1 nM or lower, most preferably 0.05 nM or lower.

The compounds of the present invention according to a certain embodiment show high specificity (selectivity) for $EP_4$. The selectivity for $EP_4$ can be evaluated by, for example, performing measurement of agonist activity and receptor binding test using cells that express each of human $EP_1$, $EP_2$, and $EP_3$ receptors to calculate ratio of the $IC_{50}$ values (concentration of the compound of the present invention at which the binding of [$^3$H]PGE$_2$ and the receptor is suppressed by 50%), or the Ki values. Specifically, the method described in Test Example 2 can be exemplified.

Ratio of $IC_{50}$ value(time)=$IC_{50}$ for each receptor/$IC_{50}$ for $EP_4$

Ratio of $Ki$ value(time)=Dissociation constant $Ki$ for each receptor/Dissociation constant $Ki$ for $EP_4$ In order to avoid side reactions, it is preferred that the compounds of the present invention according to a certain embodiment show high specificity for $EP_4$. For example, the ratio of the $IC_{50}$ value or Ki value should be 10 times or larger, preferably 100 times or larger, more preferably 1,000 times or larger, further preferably 3000 times or larger, particularly preferably 10,000 times or larger.

It is also preferred that the compounds of the present invention according to a certain embodiment selectively act on or bind to the $EP_4$ receptor, but do not act on or bind to the $EP_1$ receptor, $EP_2$ receptor, and $EP_3$ receptor, as well as DP receptor, FP receptor, IP receptor, TP receptor, PPARα receptor, PPARδ receptor, PPARγ receptor, S1P receptors (e.g., S1P1 receptor, S1P2 receptor, S1P3 receptor and the like), LTB4 receptors (e.g., BLT1, BLT2 and the like), LPA receptors (e.g., LPA1 receptor, LPA2 receptor, LPA3 receptor and the like), and cannabinoid receptors (e.g., CB1 receptor, CB2 receptor and the like), or act on or bind to these more weakly compared with the action on or binding to the $EP_4$ receptor.

The disease relating to the $EP_4$ receptor agonization is not particularly limited so long as it is a disease for which agonization of the $EP_4$ receptor is effective, and specific examples include, for example, bone fracture and bone defect.

The compounds of the present invention according to a certain embodiment have an osteogenesis-promoting action as shown in the test examples mentioned later, and are useful as an active ingredient of a medicament. The compounds of the present invention according to a certain embodiment are used for, in particular, therapeutic treatment and/or promotion of healing of fracture or bone defect, and preferably used for therapeutic treatment and/or promotion of healing of fracture. As another embodiment, they are also preferably used for therapeutic treatment and/or promotion of healing of bone defect.

Usefulness of the medicament of the present invention according to a certain embodiment for therapeutic treatment and/or promotion of healing of fracture or bone defect can be confirmed by using a closed fracture model or a partial or most long bone defect model. Specifically, the method described in Test Example 5 is exemplified.

The medicament of the present invention according to a certain embodiment can be expected to exhibit a systemic bone density-increasing action and bone strength-increasing action, or local bone regeneration/osteoanagenesis-promoting action. The osteogenesis-promoting action of the compounds of the present invention according to a certain embodiment can be evaluated by, for example, using bone marrow cells isolated from experimental animals such as rats, or human, and cultured, and using number of formed calcified bone-like nodules, alkaline phosphatase activity, which is a differentiation marker of osteoblasts or the like as a marker. It can also be evaluated by using pathological model animals such as reduced bone mass model rats subjected to sciatic nerve resection and ovariectomy or the like, and bone density or bone strength of the appendicular skeletons or the like as a marker. It can also be evaluated by using a rat long bone closed fracture model or bone cut model prepared by invasive operation, a model in which bone defect is created in an arbitrary region or the like, and osteogenesis, bone union rate, bone strength of restored bone or the like as a marker.

Fracture means a condition that a bone is partially or completely interrupted or deformed caused by an external force. The bone that may suffer from fracture is not particularly limited, so long as it is of a patient whose osseous tissue is damaged, and examples include, for example, facial bones (orbital bone, cheek bone, mandible), trunk bones (rib, pelvis, cervical vertebra, thoracic vertebra, lumbar vertebra, sacral bone, coccygeal bone), bones of the upper limb (scapula, clavicle, humerus, elbow, radius, ulna, scaphoid, hamatum, metacarpus, phalanx), bones of the lower limb (hip joint, femur, tibia, fibula, ankle joint, calcaneus, scaphoid, metatarsus) and the like, and the objective bone may be of any part. The type of the damage of osseous tissue is not particularly limited, and promotion of union of bones in fracture (complete fracture, incomplete fracture, simple fracture, comminuted fracture and the like), or bone intentionally cut in osteotomy or bone extension surgery adapted as one of the surgical treatment means is also included. Femoral neck fracture, vertebral compression fracture, fracture of the distal radius, fracture of humerus proximal end and the like, of which causative disease is osteoporosis, are also included in the scope of the fracture mentioned above.

Bone defect means various bone diseases themselves such as osteoncus, osteomyelitis, traumatic injury, chronic articular disease, prolonged healing after fracture, and slack of artificial joint, or a condition that a defect of a bone is formed by surgically excising a lesion in a treatment of such diseases. The part thereof is not particularly limited, so long as it is of a patient who has been obliged to have a bone defect. Examples include facial bones (orbital bone, cheek bone, mandible), trunk bones (rib, pelvis, cervical vertebra, thoracic vertebra, lumbar vertebra, sacral bone, coccygeal bone), bones of the upper limb (scapula, clavicle, humerus, elbow, radius, ulna, scaphoid, hamatum, metacarpus, phalanx), bones of the lower limb (hip joint, femur, tibia, fibula, ankle joint, calcaneus, scaphoid, metatarsus) and the like, and the objective bone may be of any part. The type of bone defect is not particularly limited, and bone defects of any type such as a condition that intermediate part of a bone is extensively defective, and a condition that a bone becomes partially defective because of comminuted fracture are included.

The medicament of the present invention according to a certain embodiment can be used as a bone union-promoting agent at the time of surgical therapeutic interventions. For example, it can be used in spine (cervical vertebra, thoracic vertebra, and lumbar vertebra) fixation, denatured scoliosis surgery, joint replacement, vertebral canal expansion, osteotomy, bone extension surgery, cranial bone defect compensation, cranioplasty, ilium spacer fixation with bony support, heterologous bone grafting, homologous bone grafting, autologous bone grafting, and bone graft substitute therapy, as well as bone restoration and/or bone reconstruction after surgical extraction of primary malignant tumor or bone metastasis lesion, which are exemplified as medical interventions.

The medicament of the present invention according to a certain embodiment is preferably used as an osteogenesis-promoting agent. The medicament of the present invention according to a certain embodiment is more preferably used for therapeutic treatment and/or promotion of healing of fracture or bone defect. Further, the medicament of the present invention according to a certain embodiment is extremely preferably used for prophylactic and/or therapeutic treatment of fracture. In addition, it can be easily understood by those skilled in the art that a medicament for preventing or suppressing progress of a pathological condition falls within the scope of the medicament for prophylactic and/or therapeutic treatment referred to in the present invention, as the case may be.

The medicament of the present invention according to a certain embodiment can be prepared as a medicament containing a compound represented by the formula (1) or a pharmaceutically acceptable salt thereof as an active ingredient, and for example, a medicament containing a compound or a pharmaceutically acceptable salt thereof that is metabolized in a living body to produce the compound represented by the formula (1) or a pharmaceutically acceptable salt thereof when it is administered as a prodrug also falls within the scope of the medicament of the present invention.

Although administration route of the medicament of the present invention according to a certain embodiment is not particularly limited, the administration scheme can be appropriately selected from, for example, oral administration, subcutaneous administration, intracutaneous administration, intramuscular injection, intravenous administration, pernasal administration, intravaginal administration, intrarectal administration, local administration to an affected part and the like. The local administration to an affected part is one of the preferred administration schemes.

As the medicament of the present invention, a compound represented by the formula (1) or a pharmaceutically acceptable salt thereof, per se, may be used. However, it is preferable to add one or more kinds of pharmaceutically acceptable carriers to the compound represented by the formula (1) or a pharmaceutically acceptable salt thereof to prepare a pharmaceutical composition and administer the composition. Further, as the active ingredient of the medicament of the present invention, a hydrate or solvate of a compound represented by the general formula (I) or a pharmaceutically acceptable salt thereof may be used.

Examples of dosage form used for preparing the aforementioned pharmaceutical composition include tablet, powder, granule, syrup, suspension, capsule, inhalant, injection and the like. For the manufacture of them, various carriers suitable for these preparations are used. For example, examples of the carrier for oral preparations include excipients, binders, lubricants, fluid accelerators, and colorants. Examples of the method for using the composition as an inhalants include a method of inhaling powder of the pharmaceutical composition or a liquid dosage form prepared by dissolving or suspending the pharmaceutical composition in a solvent as it is, a method of inhaling mist thereof by using a sprayer called atomizer or nebulizer and the like. When the composition is formulated as an injection, distilled water for injection, physiological saline, glucose aqueous solution, vegetable oil for injection, propylene glycol, polyethylene glycol and the like can generally be used as a diluent. Disinfectants, antiseptics, stabilizers, isotonic agents, soothing agents and the like may be further added, as required. A clathrate compound in which the compound of the present invention is clathrated in cyclodextrin may be prepared, and used as the medicament of the present invention.

When the medicament of the present invention according to a certain embodiment is administered, an appropriate dosage form can be suitably chosen and administered via an appropriate route. For example, it can be orally administered in the form of tablet, powder, granule, syrup, suspension, capsule or the like. The medicament can also be administered via the respiratory tract in the form of an inhalant. In addition, the medicament can be subcutaneously, intracutaneously, intravascularly, intramuscularly, or intraperitoneally administered in the form of an injection including drip infusion. Furthermore, the medicament can be transmucosally administered in the form of sublingual tablet, suppository or the like, and can be percutaneously administered in the form of gel, lotion, ointment, cream, spray or the like. In addition, the medicament can also be administered as a prolonged action drug, for example, a sustained-release injection, or an embedding formulation (e.g., film formulation and the like).

When the medicament of the present invention according to a certain embodiment is locally administered, the medicament can be directly administered to a local site such as fracture part. In such a case, the compound can be directly injected to the local site together with an appropriate non-hydrophilic solvent, or the compound can also be formulated in an appropriate carrier such as biodegradable polymers, and used as a medicament molded into a rod shape, needle shape, spherical shape, film shape or the like, or in the form of ointment, cream, or gel, or sustained release preparation by embedding or injecting the medicament in a local site such as fracture part. Examples of the biodegradable high molecular polymer include, for example, aliphatic acid polyesters (polymers and copolymers of one or more kinds of α-hydroxycarboxylic acids, hydroxydicarboxylic acids, lactic acid/caprolactone, valerolactone and the like, and mixtures thereof), derivatives thereof (polylactic acids, polyglycolic acids, block polymers of polyethylene glycol and the like), poly-α-cyanoacrylic acid esters, poly-β-hydroxybutyric acids, polyalkylene oxalates, polyortho-esters, polyortho-carbonates, polyocarbonates, polyamino acids, hyaluronic acid esters, polystyrene groups, polymethacrylic acids, copolymers of acrylic acid and methacrylic acid, polyamino acids, decyne stearate, ethylcellulose, acetylcellulose, nitrocellulose, maleic anhydride copolymers, ethylene vinyl acetate copolymers, polyvinyl acetates, polyacrylamides, collagen, gelatin, fibrin, bone meal, bone cement and the like.

The biodegradable high molecular polymer may consist of one kind of substance, or a copolymer, a complex, or a simple mixture of two or more kinds of substances, and the polymerization scheme thereof may be any of random, block, and graft polymerizations.

The medicament of the present invention according to a certain embodiment can also be applied or adsorbed on an artificial bone (implant) consisting of a highly biocompatible material (metal, calcium, ceramics, polymer materials and the like), bone prosthesis (hydroxyapatite, β-tricalcium phosphate and the like) or the like together with an appropriate solvent or carrier, or embedded therein, and administered to a local site.

The administration period of the medicament of the present invention according to a certain embodiment is not particularly limited. In principle, the medicament is administered during a period where it is judged that clinical symptoms of a disease are expressed, and it is common to continue the administration for several weeks to one year. However, it is also possible to extend the administration period depending on pathological conditions, or continue the administration even after recovery from the clinical symptoms. The medicament may also be prophylactically administered by a decision of a clinician even if any clinical symptom is not expressed. The dose of the medicament of the present invention according to a certain embodiment is not particularly limited. When the medicament of the present invention is directly administered to a local site such as fracture part, 0.01 to 1,000 µg of the active ingredient can be administered to an adult per each administration. As for administration frequency in the above case, the medicament may be administered at a frequency of every 6 months to every day, and the medicament may preferably be administered once per 3 months to once per month, or once per week.

The daily dose and/or dose per one time, administration period, and administration frequency may be suitably increased or decreased depending on various conditions such as age, weight, degree of physical healthiness of a patient, type and severity of a disease to be treated, administration route, and dosage form (sustained release property of carrier for active ingredient and the like).

When the medicament of the present invention according to a certain embodiment is used for therapeutic treatment and/or promotion of healing of fracture or bone defect, or prophylactic and/or therapeutic treatment of fracture, the medicament of the present invention according to a certain embodiment can be used together with one or more kinds of medicaments selected from the group consisting of bone-activating agents, osteogenesis-promoting agents, bone resorption-suppressing agents, bone metabolism-improving agents, sexual hormone preparations, and calcium preparations, simultaneously or at different times. Further, the medicament of the present invention according to a certain embodiment can also be prepared as a so-called combined drug together with the medicaments exemplified above, and then administered. The aforementioned combined drug may be in a dosage form as a complete mixture of the active ingredients similar to typical compositions of such type, as well as a dosage form, kit, or package including a non-mixed combination of ingredients separately administered from two or more containers each of which contains each active ingredient.

Examples of the bone-activating agents usable in combination with the medicament of the present invention according to a certain embodiment include, for example, vitamin D or vitamin D derivatives such as calcitriol, alfacalcidol, OCT, 2MD, and ED-71, examples of the osteogenesis-promoting agents include, for example, menatetrenone, teriparatide, somatropin, insulin-like growth factor-I (IGF-I), bone morphogenetic proteins (BMPs), basic fibroblast growth factor (bFGF), transforming growth factor-β (TGF-β), $EP_2$ agonist, LRP5 agonist, anti-SOST antibody, GSK-3 inhibitor, Dkk1 inhibitor, calcilytics, growth hormone secretagogues and the like, examples of the bone resorption-suppressing agents include, for example, elcatonin, calcitonin salmon, etidronate, pamidronate, clodronate, alendronate, incadronate, risedronate, minodronate, ibandronate, cathepsin K inhibitors, osteoprotegerin, anti-RANKL antibodies and the like, examples of the bone metabolism-improving agents include, for example, fluoride, strontium ranelate, ipriflavone and the like, examples of the sexual hormone preparations include, for example, estriol, estradiol, conjugated estrogen, progesterone, medroxyprogesterone, testosterone, metyltestosterone, mestanolone, stanozolol, metenolone, nandrolone, selective estrogen receptor modulators (SERM: raloxifen, lasofoxifene, bazedoxifene, ospemifene, arzoxifene, CHF4227, PSK-3471 and the like), selective androgen receptor modulators (SARM) and the like, and examples of the calcium preparations include, for example, calcium carbonate, calcium lactate, calcium gluconate, calcium acetate, calcium chloride, calcium citrate, calcium hydrogenphosphate, calcium L-aspartate and the like. It can also be used together with various kinds of drugs for bone diseases to be created in the future. These combined drugs are not limited so long as the combinations are clinically meaningful.

The compounds of the present invention according to a certain embodiment include compounds showing superior safety (concerning various toxicities and safety pharmacology), pharmacokinetic performance and the like, and usefulness thereof as an active ingredient of a medicament can be confirmed by, for example, the methods shown below.

Examples of tests concerning safety include, for example, those listed below. However, they are not limited to these examples. Examples include cytotoxic tests (tests using HL60 cells, hepatocytes and the like), genotoxicity tests (Ames test, mouse lymphoma TK test, chromosomal aberration test, micronucleus test and the like), skin sensitization tests (Buehler method, GPMT method, APT method, LLNA test and the like), skin photosensitization tests (adjuvant and strip method and the like), eye irritation tests (single instillation, short-term continuation instillation, repetitive instillation and the like), safety pharmacology tests for the cardiovascular system (telemetry method, APD method, hERG inhibition assay and the like), safety pharmacology tests for the central nervous system (FOB method, modified version of Irwin method and the like), safety pharmacology tests for the respiratory system (measurement method utilizing a respiratory function measuring apparatus, measurement method utilizing a blood gas analyzer and the like), general toxicity tests, reproductive and developmental toxicity tests and the like.

Examples of tests concerning pharmacokinetic performance include, for example, those listed below. However, they are not limited to these examples. Examples include cytochrome P450 enzyme inhibition or induction tests, cell permeability tests (tests using CaCO-2 cells, MDCK cells and the like), drug transporter ATPase assay, oral absorption tests, blood concentration transition measurement tests, metabolism tests (stability test, metabolite molecular species test, reactivity test and the like), solubility tests (solubility test based on turbidity method and the like) and the like.

Usefulness of the compounds of the present invention according to a certain embodiment as an active ingredient of a medicament can be confirmed by performing, for example, a cytotoxic test. Examples of the cytotoxic test include methods utilizing various cultured cells, for example, HL-60 cells, which are human preleukemia cells, primary isolated cultured cells of hepatocytes, a neutrophil fraction prepared from human peripheral blood and the like. Although the test can be carried out by the method described below, the method is not limited only to the following description. Cells are prepared as a suspension of $10^5$ to $10^7$ cells/ml, and the suspension is added to microtubes or microplate in a volume of 0.01 to 1 mL. To the suspension, a solution dissolving a compound is added in a volume of 1/100 to 1 fold volume of the cell suspension, and the cells were cultured in a cell culture medium having a final concentration of the compound of 0.001 to 1,000 µM for 30 minutes to several days at 37° C. under 5% $CO_2$. After terminating the culture, survival rate of the cells is evaluated by using the MTT method, WST-1 method (Ishiyama, M., et al., In Vitro Toxicology, 8, p. 187, 1995) or the like. By measuring cytotoxicity of a compound to cells, usefulness of the compound as an active ingredient of a medicament can be confirmed.

Usefulness of the compounds of the present invention according to a certain embodiment as an active ingredient of a medicament can be confirmed by performing, for example, a genotoxicity test. Examples of the genotoxicity test include, the Ames test, mouse lymphoma TK test, chromosomal aberration test, micronucleus test and the like. The Ames test is a method of determining reverse mutation by culturing *Salmonella* or *Escherichia* bacteria of designated species on a culture dish or the like added with a compound (refer to IYAKUSHIN (Notification by the chief of Evaluation and Licensing Division, Pharmaceutical and Medical Safety Bureau, Ministry of Health, Labor and Welfare, Japan), No. 1604, 1999, "Guideline for Genotoxicity Test", II-1. Genotoxicity Test and the like). The mouse lymphoma TK test is a genetic mutation ability detection test targeting the thymidine kinase gene of the mouse lymphoma L5178Y cell (refer to IYAKUSHIN No. 1604, 1999, "Guideline for Genotoxicity Test", 11-3. Mouse Lymphoma TK Test; Clive, D. et al., Mutat. Res., 31, pp. 17-29, 1975; Cole, J., et al., Mutat. Res., 111, pp. 371-386, 1983 and the like). The chromosomal aberration test is a method for determining activity of causing chromosomal aberration by culturing mammalian cultured cells in the presence of a compound, then after fixation of the cells, staining and observing chromosomes of the cells (refer to IYAKUSHIN No. 1604, 1999, "Guideline for Genotoxicity Test", 11-2. Chromosomal Aberration Test Utilizing Mammalian Cultured Cells and the like). The micronucleus test is a method of evaluating micronucleus-forming ability caused by chromosomal aberration, and a method of using a rodent (in vivo test) (IYAKUSHIN No. 1604, 1999, "Guideline for Genotoxicity Test", 11-4. Micronucleus Test Using Rodent; Hayashi M. et al., Mutat. Res., 312, pp. 293-304, 1994; Hayashi, M. et al., Environ. Mol. Mutagen., 35, pp. 234-252, 2000), a method of using cultured cells (in vitro test) (Fenech M., et al., Mutat. Res., 147, pp. 29-36, 1985; Miller, B., et al., Mutat. Res., 392, pp. 45-59, 1997) and the like are available. By elucidating genotoxicity of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a skin sensitization test. Skin sensitization tests include, as the skin sensitization tests using guinea pig, the Buehler method (Buehler, E. V., Arch. Dermatol., 91, pp. 171-177, 1965), GPMT method (maximization method, Magnusson B., et al., J. Invest. Dermatol., 52, pp. 268-276, 1969), APT method (adjuvant and patching method (Sato, Y. et al., Contact Dermatitis, 7, pp. 225-237, 1981)) and the like. Further, as the skin sensitization test using mouse, the LLNA (local lymph node assay) method (OECD Guideline for the testing of chemicals 429, Skin sensitization 2002; Takeyoshi, M. et al., Toxicol. Lett., 119 (3), pp. 203-8, 2001; Takeyoshi, M. et al., J. Appl. Toxicol., 25 (2), pp. 129-34, 2005) and the like are available By elucidating skin sensitization property of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a skin photosensitization test. Examples of the skin photosensitization test include a skin photosensitization test using guinea pig (refer to "Drug Nonclinical Test Guideline Commentary 2002", Yakuji Nippo, published on 2002, 1-9: Skin Photosensitization Test and the like) and the like, and examples of the method include the adjuvant and strip method (Ichikawa, H. et al., J. Invest. Dermatol., 76, pp. 498-501, 1981), Harber method (Harber, L. C., Arch. Dermatol., 96, pp. 646-653, 1967), Horio method (Horio, T., J. Invest. Dermatol., 67, pp. 591-593, 1976), Jordan method (Jordan, W. P., Contact Dermatitis, 8, pp. 109-116, 1982), Kochever method (Kochever, I. E. et al., J. Invest. Dermatol., 73, pp. 144-146, 1979), Maurer method (Maurer, T. et al., Br. J. Dermatol., 63, pp. 593-605, 1980), Morikawa method (Morikawa, F. et al., "Sunlight and Man", Tokyo Univ. Press, Tokyo, pp. 529-557, 1974), Vinson method (Vinson, L. J., J. Soc. Cosm. Chem., 17, pp. 123-130, 1966) and the like. By elucidating skin photosensitization property of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, an eye irritation test. Examples of the eye irritation test include the single instillation test method using rabbit eyes, monkey eyes and the like (instillation of one time), short term continuous instillation test method (instillation of multiple times in a short period of time with equal intervals), repetitive instillation test method (repetitive intermittent instillation over several days to several 10 days) and the like, and a method of evaluating eye irritation symptoms during a certain period of time after instillation according to the improved Draize scores (Fukui, N. et al., Gendai no Rinsho, 4 (7), pp. 277-289, 1970) and the like are available By elucidating eye irritation of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a safety pharmacology test for the cardiovascular system. Examples of the safety pharmacology test for the cardiovascular system include the telemetry method (method for measuring influence of administration of a compound under no anesthetization on electrocardiogram, heart rate, blood pressure, blood stream and the like (Electrocardiogram, Echocardiography, Blood Pressure and Pathological Tests of Animals for Fundamental and Clinical Medicine, edited by Sugano S., Tsubone H., Nakada Y, published on 2003, Maruzen), APD method (method for measuring cardiac muscle cell action potential retention time (Muraki, K. et al., AM. J. Physiol., 269, H524-532, 1995; Ducic, I. et al., J. Cardiovasc. Pharmacol., 30 (1), pp. 42-54, 1997)), hERG inhibition evaluation method (patch clamping method (Chachin, M. et al., Nippon Yakurigaku Zasshi, 119, pp. 345-351, 2002), binding assay method (Gilbert, J. D. et al., J. Pharm. Tox. Methods, 50, pp. 187-199, 2004), $Rb^+$ efflux assay method (Cheng, C. S. et al., Drug Develop. Indust. Pharm., 28, pp. 177-191, 2002), Membrane potential assay method (Dorn, A. et al., J. Biomol. Screen., 10, pp. 339-347, 2005) and the like. By elucidating influence on the cardiovascular system of a compound using on one or more of these methods, usefulness of the compound as an active ingredient of a medicament can be confirmed.

Usefulness of the compounds of the present invention according to a certain embodiment as an active ingredient of a medicament can be confirmed by performing, for example, a safety pharmacology test for the central nervous system. Examples of the safety pharmacology test for the central nervous system include the FOB method (Functional Observational Battery, Mattson, J. L. et al., J. American College of Technology, 15 (3), pp. 239-254, 1996)), modified version of Irwin method (method for evaluating observation of general symptoms and behavior (Irwin, S., Comprehensive Observational Assessment (Berl.) 13, pp. 222-257, 1968)) and the like. By elucidating action on the central nervous system of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a safety pharmacology test for the respiratory system. Examples of the safety pharmacology test for the respiratory system include the measurement method using a respiratory function measuring apparatus (method of measuring respiration rate, single ventilation volume, minute ventilation and the like, Drorbaugh, J. E. et al., Pediatrics, 16, pp. 81-87, 1955; Epstein, M. A. et al., Respir. Physiol., 32, pp. 105-120, 1978), measurement method of using a blood gas analyzer (method of measuring blood gas, hemoglobin oxygen saturation and the like, Matsuo, S., Medicina, 40, pp. 188-, 2003) and the like. By elucidating action on the respiratory system of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a general toxicity test. The general toxicity test is a method of orally or intravenously administering a compound dissolved or suspended in an appropriate solvent once or repetitively (over several days) to a rodent such as rat and mouse or non-rodent such as monkey and dog, and evaluating observation of general conditions, clinicochemical changes, pathohistological changes and the like of the administered animal. By elucidating general toxicity of a compound using these methods, usefulness of the compound as an active ingredient of a medicament can be confirmed.

Usefulness of the compounds of the present invention according to a certain embodiment as an active ingredient of a medicament can be confirmed by performing, for example, a reproductive and developmental toxicity test. The reproductive and developmental toxicity test is a test for examining induction of harmful effect caused by a compound on the reproductive and developmental processes by using a rodent such as rat and mouse, or non-rodent such as monkey and dog (refer to "Drug Nonclinical Test Guideline Commentary 2002", Yakuji Nippo, published on 2002, 1-6: Reproductive and Developmental Toxicity Test and the like). Examples of the reproductive and developmental toxicity test include tests concerning fertility and early embryogenesis up to nidation, tests concerning development and maternal functions before and after birth, tests concerning embryogenesis and fetal development (refer to IYAKUSHIN No. 1834, 2000, Appendix, "Guideline for Drug Toxicity Test", [3] Reproductive and Developmental Toxicity Test and the like) and the like. By elucidating reproductive and developmental toxicity of a compound using these methods, usefulness of the compound as an active ingredient of medicament can be confirmed.

Usefulness of the compounds of the present invention according to a certain embodiment as an active ingredient of a medicament can be confirmed by performing, for example, a cytochrome P450 enzyme inhibition or induction test (Gomez-Lechon, M. J. et al., Curr. Drug Metab., 5 (5), pp. 443-462, 2004). Examples of the cytochrome P450 enzyme inhibition or induction test include, for example, the method of determining in vitro whether a compound inhibits activity of a cytochrome P450 enzyme by using a cytochrome P450 enzyme of each molecular species purified from cells or prepared by using a genetic recombinant, or a human P450 expression system microsome (Miller, V. P. et al., Ann. N.Y. Acad. Sci., 919, pp. 26-32, 2000), method of measuring changes of expression of cytochrome P450 enzyme of each molecular species or enzyme activity by using human liver microsomes or disrupted cell suspension (Hengstler, J. G. et al., Drug Metab. Rev., 32, pp. 81-118, 2000), method of extracting RNA from human hepatocytes exposed to a compound, and comparing mRNA expression amount with that of a control to investigate enzyme induction ability of the compound (Kato, M. et al., Drug Metab. Pharmacokinet., 20 (4), pp. 236-243, 2005) and the like. By elucidating action of a compound on inhibition or induction of cytochrome P450 enzyme using one or more of these methods, usefulness of the compound as an active ingredient of a medicament can be confirmed.

Usefulness of the compounds of the present invention according to a certain embodiment as an active ingredient of a medicament can be confirmed by performing, for example, a cell permeability test. Examples of the cell permeability test include, for example, the method of measuring cell membrane permeability of a compound in an in vitro cell culture system using CaCO-2 cells (Delie, F. et al., Crit. Rev. Ther. Drug Carrier Syst., 14, pp. 221-286, 1997; Yamashita, S. et al., Eur. J. Pham. Sci., 10, pp. 195-204, 2000; Ingels, F. M. et al., J. Pham. Sci., 92, pp. 1545-1558, 2003), method of measuring cell membrane permeability of a compound in an in vitro cell culture system using MDCK cells (Irvine, J. D. et al., J. Pham. Sci., 88, pp. 28-33, 1999) and the like. By elucidating cell permeability of a compound using one or more of these methods, usefulness of the compound as an active ingredient of a medicament can be confirmed.

Usefulness of the compounds of the present invention according to a certain embodiment as an active ingredient of a medicament can be confirmed by performing, for example, a drug transporter ATPase assay for ATP-binding cassette (ABC) transporter. Examples of the drug transporter ATPase assay include the method of examining whether a compound is a substrate of P-glycoprotein (P-gp) by using a P-gp baculovirus expression system (Germann, U. A., Methods Enzymol., 292, pp. 427-41, 1998) and the like Furthermore, the usefulness can also be verified by performing, for example, a transport test using oocytes collected from African clawed frog (Xenopus laevis) as a solute carrier (SLC) transporter. Transport tests include a method of examining whether a test compound is a substrate of OATP2 using OATP2-expressing oocytes (Tamai I. et al., Pharm. Res., 2001 September; 18 (9), 1262-1269) and the like. By elucidating action of a compound on the ABC transporter or SLC transporter using these methods, usefulness of the compound as an active ingredient of a medicament can be confirmed.

Usefulness of the compounds of the present invention according to a certain embodiment as an active ingredient of a medicament can be confirmed by performing, for example, an oral absorption test. Examples of the oral absorption test include a method of orally administering a compound of a certain amount dissolved or suspended in an appropriate solvent to a rodent, monkey, dog or the like, and measuring blood level of the compound after the oral administration over time to evaluate blood transition of the compound by oral administration using the LC-MS/MS method ("Newest Mass Spectrometry for Life Science", Kodansha Scientific, 2002, edited by Harada K. et al and the like) and the like. By elucidating oral absorption of a compound using these methods, usefulness of the compound as an active ingredient of a medicament can be confirmed.

Usefulness of the compounds of the present invention according to a certain embodiment as an active ingredient of a medicament can be confirmed by performing, for example, a blood concentration transition measurement test. Examples of the blood concentration transition measurement test include a method of orally or parenterally (e.g., intravenously, intramuscularly, intraperitoneally, subcutaneously, transdermally, by instillation, transnasally and the like) administering a compound to a rodent, monkey, dog or the like, and measuring change of the blood level of the compound over time after the administration using the LC-MS/MS method ("Newest Mass Spectrometry for Life Science", Kodansha Scientific, 2002, edited by Harada K. et al and the like) and the like. By elucidating blood concentration transition of a compound using these methods, usefulness of the compound as an active ingredient of a medicament can be confirmed. In the case of, in particular, local administration among the parenteral administrations, in order to avoid side reactions, the compounds of the present invention according to a certain embodiment showing low blood concentration after administration thereof may be preferred.

Usefulness of the compounds of the present invention according to a certain embodiment as an active ingredient of a medicament can be confirmed by performing, for example, a metabolic test. Examples of the metabolic test include the blood stability test method (method of predicting metabolic clearance in vivo on the basis of metabolic rate of a compound in hepatic microsomes of human or other animal species (refer to Shou, W. Z. et al., J. Mass Spectrom., 40 (10) pp. 1347-1356, 2005; Li, C. et al., Drug Metab. Dispos., 34 (6), 901-905, 2006 and the like), metabolite molecular species test method, reactive metabolite test method and the like. By elucidating metabolic profile of a compound by using one or more of these methods, usefulness of the compound as an active ingredient of a medicament can be confirmed.

Usefulness of the compounds of the present invention according to a certain embodiment as an active ingredient of a medicament can be confirmed by performing, for example, a solubility test. As the method for evaluating solubility in water, the methods of confirming the solubility under acidic conditions, neutral conditions, or basic conditions are exemplified, and confirming change of solubility depending on the presence or absence of bile acid is also included. Examples of the solubility test include the solubility test based on the turbidity method (Lipinski, C. A. et al., Adv. Drug Deliv. Rev., 23, pp. 3-26, 1997; Bevan, C. D. et al., Anal. Chem., 72, pp. 1781-1787, 2000) and the like. By elucidating solubility of a compound using these methods, usefulness of the compound as an active ingredient of a medicament can be confirmed.

Usefulness of the compounds of the present invention according to a certain embodiment as an active ingredient of a medicament can be confirmed by examining, for example, upper gastrointestinal injury, renal dysfunction and the like. As a pharmacological test for the upper gastrointestinal tract, actions on gastric mucosa can be investigated by using a starved rat gastric mucosa injury model. Examples of pharmacological test for kidney functions include renal blood flow and glomerular filtration rate measuring method [Physiology, 18th edition, Bunkodo, 1986, Chapter 17] and the like. By elucidating actions of a compound on the upper gastrointestinal tract and renal functions using one or more of these methods, usefulness of the compound as an active ingredient of a medicament can be confirmed.

EXAMPLES

Hereafter, the present invention will be further specifically explained with reference to examples, reference examples, preparation examples, and test examples (these may be henceforth collectively referred to as "examples and the like"). However, the scope of the present invention is not limited to the following examples and the like In the examples and the like, for thin layer chromatography (TLC), Precoated Silica Gel 60 F254 (produced by Merck, product number 5715-1M)) was used. After development with chloroform:methanol (1:0 to 1:1), acetonitrile:acetic acid:water (200:1:1 to 100:4:4) or ethyl acetate:hexane (1:0 to 0:1), confirmation was performed by UV irradiation (254 nm or 365 nm), or coloration with iodine solution, aqueous potassium permanganate, phosphomolybdic acid (ethanol solution) or the like.

For drying organic solvent, anhydrous magnesium sulfate or anhydrous sodium sulfate was used.

For column chromatography, Multi Prep YFLC produced by Yamazen Corporation, or 2-ch parallel purification apparatus "Purif-α2(50F)" produced by MORITEX Corporation was used. In the case of Multi Prep YFLC, any of Ultra Pack Si-40A, 40B and 40D produced by Yamazen Corporation was used as the column, and in the case of Purif-α2(50F), PurifPack-Si series produced by MORITEX Corporation was used as the column.

For flash column chromatography, Silica gel 60N (spherical shape, neutral, 40 to 100 μm, produced by Kanto Chemicals) was used.

Preparative thin layer chromatography (henceforth also referred to as "PTLC") was performed by using one or several plates of PLC Plate Silica Gel 60 F254 (20×20 cm, layer thickness 2 mm, including concentration zone (4 cm), produced by Merck, product number 13793-1M) were used depending on the amount of sample.

For HPLC purification, a liquid chromatography preparation and purification apparatus produced by Waters Japan was used, Develosil C30-UG-5 (produced by Nomura Kagaku) or the like was used as the column, and water-acetonitrile solvent containing 0.1% acetic acid was used as the eluent.

When purification was performed by HPLC, the object compound was obtained by removing the solvent by lyophilization, unless particularly indicated. For the measurement of nuclear magnetic resonance (NMR) spectra, Gemini-300 (FT-NMR, Varian Co., Ltd.) or AL-300 (FT-NMR, produced by JEOL Co., Ltd.) was used. As the solvent, deuterated chloroform was used unless specifically indicated, chemical shifts were measured by using tetramethylsilane (TMS) as an internal standard, and indicated with δ (ppm), and the binding constant was indicated with J (Hz).

For LCMS, mass spectrum was measured by liquid chromatography-mass spectrometry (LC-MS). Unless especially indicated, a single quadrupole mass spectrometer, UPLC/SQD System (produced by Waters) was used as the mass spectrometer, and the measurement was performed by the electrospray ionization (ESI) method. As the liquid chromatography apparatus, Acquity Ultra Performance LC System produced by Waters was used. As the separation column, ACQUITY UPLC BEH C18 (1×50 mm, 1.7 μm, produced by Waters) was used.

However, for the LC conditions of FLC-1 mentioned below, a single quadrupole mass spectrometer, Platform-LC (produced by Waters) was used as the mass spectrometer, and the measurement was performed by the electrospray ionization (ESI) method. As the liquid chromatography apparatus, 306 PUMP System produced by GILSON was used. As the separation column, Develosil C30-UG-5 (50×4.6 mm, produced by Nomura Kagaku) was used.

When LC conditions are especially mentioned in the examples and reference examples, it means that the measurement was performed with the following solvent conditions. The symbol m/z means mass spectrum data ($MH^+$, $M^+NH_4^+$, or $MH^-$ is also indicated).

(LC-1) The measurement was performed under the conditions that the elution was performed at a flow rate of 0.6 ml/minute using a linear gradient of 5 to 90% (v/v) of Solution B [acetonitrile containing 0.1% (v/v) acetic acid] in Solution A [water containing 0.1% (v/v) acetic acid] from 0 minute to 2.0 minutes, and then a linear gradient of 90 to 98% of Solution B in Solution A from 2.0 to 2.5 minutes.

(LC-6) The measurement was performed under the conditions that the elution was performed at a flow rate of 0.6 ml/minute using a linear gradient of 70 to 90% (v/v) of Solution B [acetonitrile containing 0.1% (v/v) acetic acid] in Solution A [water containing 0.1% (v/v) acetic acid] from 0 to 2.0 minutes, and then a linear gradient of 90 to 98% of Solution B in Solution A from 2.0 to 2.5 minutes.

(NLC-1) The measurement was performed under the conditions that the elution was performed at a flow rate of 0.6 ml/minute using a linear gradient of 5 to 90% (v/v) of Solution B [acetonitrile] in Solution A [10 mM aqueous ammonium acetate] from 0 minute to 2.0 minutes, and then a linear gradient of 90 to 98% of Solution B in Solution A from 2.0 to 2.5 minutes.

(NLC-6) The measurement was performed under the conditions that the elution was performed at a flow rate of 0.6 ml/minute using a linear gradient of 70 to 90% (v/v) of Solution B [acetonitrile] in Solution A [10 mM aqueous ammonium acetate] from 0 minute to 2.0 minutes, and then a linear gradient of 90 to 98% of Solution B in Solution A from 2.0 to 2.5 minutes.

(FLC-1) The measurement was performed under the conditions that the elution was performed at a flow rate of 2 ml/minute using a linear gradient of 5 to 98% (v/v) of Solution B [acetonitrile containing 0.1% (v/v) acetic acid] in Solution A [water containing 0.1% (v/v) acetic acid] from 0 to 5 minutes, 98% (v/v) of Solution B in Solution A from 5 to 6 minutes, a linear gradient of 98 to 5% (v/v) Solution B in Solution A from 6 to 6.01 minutes, and 5% (v/v) of Solution B in Solution A from 6.01 to 7.5 minutes.

For chiral LC, retention time was measured by high performance liquid chromatography (HPLC). When chiral LC conditions are especially mentioned in the examples and reference examples, it means that the measurement was performed with the following measurement conditions.

(Chiral LC-1) The measurement was performed by using CHIRALCEL OD-H (4.6×250 mm, 5 μm, produced by Daicel Corporation) as the separation column under the conditions that the elution was performed at a flow rate of 0.6 ml/minute as isocratic elution using 5% (v/v) of Solution B (ethanol) in Solution A (n-hexane).

(Chiral LC-2) The measurement was performed by using CHIRALCEL OJ-H (4.6×250 mm, 5 μm, produced by Daicel Corporation) as the separation column under the conditions that the elution was performed at a flow rate of 1.0 ml/minute using ethanol containing 0.1% (v/v) of trifluoroacetic acid.

The manufacturers of the regents used may sometimes be indicated with the following abbreviations: Tokyo Chemical Industry Co., Ltd., TCI; Sigma-Aldrich Co. LLC., ALDRICH; Kanto Kagaku Co., Inc., KANTO; Wako Pure Chemical Industries Ltd., WAKO; Maybridge Co., Ltd., MAYBRIDGE; APOLLO Co., Ltd., APOLLO; Combi-Blocks Inc., COMBI-BLOCKS; Takasago International Corporation, TAKASAGO; Johnson Matthey Co., Ltd., JOHNSON; Nippon Chemical Industrial Co., Ltd., Nippon Chemical; and Japan EnviroChemicals, Limited, Japan EnviroChemicals.

The abbreviations or symbols used in the descriptions have the following meanings: n, normal; i, iso; s, secondary; t, tertiary; c, cyclo; Me, methyl; Et, ethyl; Pr, propyl; Bu, butyl; Pen, pentyl; Hex, hexyl; Hep, heptyl; Ph, phenyl; Bn, benzyl; Py, pyridyl; Ac, acetyl; CHO, formyl; COOH, carboxyl; $NO_2$, nitro; DMA, dimethylamino; $NH_2$, amino; $CF_3$, trifluoromethyl; F, fluoro; Cl, chloro; Br, bromo; OMe, methoxy; OH, hydroxy; TFA, trifluoroacetyl; SO$_2$, sulfonyl; CO, carbonyl; THF, tetrahydrofuran; DMF, N,N-dimethylformamide; DMSO, dimethyl sulfoxide; and DME, dimethoxyethane.

The numbers indicated before the substituents represent substitution positions. The numbers indicated before the abbreviations of aromatic rings with hyphens indicate the substitution positions on the aromatic rings. The symbol (S) mentioned in the compound names and structural formulas means that the corresponding asymmetric carbon is in the S-configuration, and (R) means that the corresponding asymmetric carbon is in the R-configuration. Further, when (R) or (S) is not indicated for a compound having an asymmetric carbon, it means that the compound consisted of a mixture of (R)-isomer and (S)-isomer at an arbitrary ratio. Such a compound may be a racemic mixture of (R)-isomer and (S)-isomer.

When deprotection is required in the synthesis process of the example compounds, it was performed according to known methods such as the methods described in Protective Groups in Organic Synthesis, published by John Wiley and Sons (2007).

Reference Example A-2: tert-Butyldimethyl(2-(thiophen-2-yl)ethoxy)silane (Intermediate A-2)

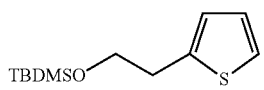

[Formula 76]

To a solution of 2-(thiophen-2-yl)ethanol (4 g, TCI) in N,N-dimethylformamide (312 mL), imidazole (4.3 g), tert-butyldimethylchlorosilane (7.05 g), and N,N-dimethyl-4-aminopyridine (763 mg) were successively added under ice cooling, and the mixture was stirred at room temperature for 2.75 hours. To the reaction mixture, ethyl acetate was added, and the organic layer was successively washed with 1 mol/L hydrochloric acid, saturated brine, saturated aqueous sodium hydrogencarbonate, and saturated brine, and then dried. The solvent was evaporated under reduced pressure to obtain the title compound (7.32 g).

(Intermediate A-2: Rf (TLC)=0.70 (hexane:ethyl acetate=4:1))

Reference Example A-3: 5-(2-((tert-Butyldimethylsilyl)oxy)ethyl)thiophene-2-carboxylic Acid (Intermediate A-3)

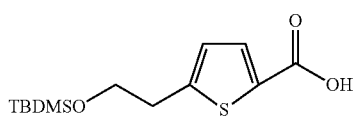

[Formula 77]

A solution of the intermediate A-2 (7.15 g) in tetrahydrofuran (111 mL) was cooled to -78° C. under a nitrogen atmosphere. To the reaction mixture, n-butyllithium (2.6 mol/L solution in hexane, 14.3 mL, KANTO) was added dropwise, and the mixture was stirred for 0.75 hour as it was. The reaction mixture was warmed to -5° C., then dry ice (125 g) was added portionwise, and after completion of the addition, the reaction mixture was further stirred for 0.75 hour. To the reaction mixture, saturated aqueous ammonium chloride was added, and the mixture was stirred at room temperature. Ethyl acetate was added to the reaction mixture for extraction, and the organic layer was washed successively with saturated aqueous ammonium chloride, and saturated brine, and then dried. The solvent was evaporated under reduced pressure to obtain the title compound (9.03 g).

(Intermediate A-3: LCMS m/z 287.0 (MH$^+$), retention time 1.35 minutes, LC conditions NLC-1)

Reference Example A-4: Methyl 5-(2-hydroxyethyl)thiophene-2-carboxylate (Intermediate A-4)

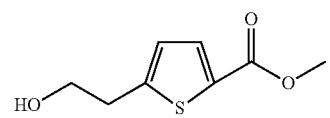

[Formula 78]

A solution of the intermediate A-3 (9.03 g) in methanol (64 mL) was cooled to 0° C., concentrated sulfuric acid (3.2 mL) was added portionwise to the solution, and the mixture was stirred as it was for 5 minutes. The reaction mixture was heated to 70° C., stirred for 24 hours, and then cooled to 0° C., and saturated aqueous sodium hydrogencarbonate was added portionwise until the reaction mixture became neutral. Ethyl acetate was added to the reaction mixture for extraction, and the organic layer was washed successively with saturated aqueous sodium hydrogencarbonate, and saturated brine, and then dried. The solvent was evaporated under reduced pressure, and the residue was purified by column chromatography (hexane/ethyl acetate) to obtain the title compound (4.61 g).

(Intermediate A-4: Rf (TLC)=0.33 (hexane:ethyl acetate=1:1))

Reference Example A-5: Methyl 5-(2-bromoethyl)thiophene-2-carboxylate (Intermediate A-5)

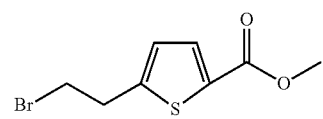

[Formula 79]

To a solution of the intermediate A-4 (4.61 g) in dichloromethane (200 mL), triphenylphosphine (9.8 g) was added, and then the mixture was cooled to 0° C. To the reaction mixture, carbon tetrabromide (12.3 g) was added portionwise, and the mixture was warmed to room temperature, and then stirred for 13.5 hours. The reaction mixture was decompressed to evaporate the solvent, and then the residue was purified by column chromatography (hexane/ethyl acetate) to obtain the title compound (5.4 g).

(Intermediate A-5: Rf (TLC)=0.70 (hexane:ethyl acetate=1:1))

Reference Example A-6: tert-Butyl 2-(2-(5-(methoxycarbonyl)thiophen-2-yl)ethyl)hydrazinecarboxylate (Intermediate A-6)

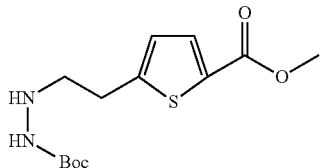

[Formula 80]

To a solution of the intermediate A-5 (6.2 g) in acetonitrile (125 mL), tert-butyl carbazate (16.5 g, TCI), sodium hydrogencarbonate (10.5 g), and sodium iodide (700 mg) were successively added, and the mixture was stirred at 90° C. for 13 hours. The reaction mixture was cooled to 0° C., ethyl acetate (155 mL) was added to the reaction mixture, and the organic layer was successively washed with 1 mol/L hydrochloric acid, saturated aqueous sodium hydrogencarbonate, and saturated brine, and then dried. The solvent was evaporated under reduced pressure, and the residue was purified by column chromatography (hexane/ethyl acetate) to obtain the title compound (5.1 g).

(Intermediate A-6: LCMS m/z 301.1 (MH$^+$), retention time 1.42 minutes, LC conditions NLC-1)

$^1$H-NMR (CDCl$_3$): δ (ppm) 7.64 (1H, d, J=4.0 Hz), 6.87 (1H, d, J=4.0 Hz), 3.86 (3H, s), 3.18 (2H, t, J=7.2 Hz), 3.02 (2H, t, J=7.2 Hz), 2.60-1.90 (2H, br), 1.64 (9H, s)

Reference Example B-3: S-(2-chloroethyl)carbochloride Thioate (Intermediate B-3)

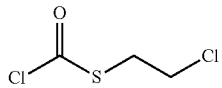

[Formula 81]

A mixed solution of ethylene sulfide (320 g, TCI), and pyridine (4.3 mL) was cooled on an ice bath under an argon atmosphere, triphosgene (474 g, TCI) was added portionwise to the reaction mixture, and the mixture was stirred as it was for 4 hours. The reaction mixture was distilled under reduced pressure (0.7 to 0.8 kPa, 50 to 52° C.) for purification to obtain the title compound (281 g).

$^1$H-NMR (CDCl$_3$): δ (ppm) 3.72 (2H, t, J=7.0 Hz), 3.30 (2H, t, J=7.0 Hz)

Reference Example Z-1: tert-Butyl 2-(((2-chloroethyl)thio)carbonyl)-2-(2-(5-(methoxycarbonyl)thiophen-2-yl)ethyl)hydrazinecarboxylate (Intermediate Z-1)

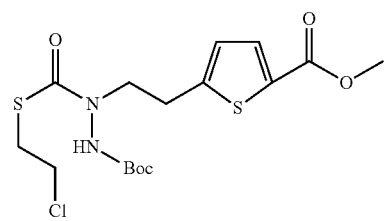

[Formula 82]

To a solution of the intermediate A-6 (140.3 g) in dichloromethane (660 mL), water (330 mL), and sodium hydrogencarbonate (78.09 g) were added, the mixture was stirred for 10 minutes, and then the intermediate B-3 (81.71 g) was added portionwise to the reaction mixture, while the internal temperature of the reaction mixture was maintained to be at 20 to 25° C. The mixture was stirred as it was for 1 hour, and then the organic layer was washed with saturated brine, and dried. The solvent was evaporated under reduced pressure to obtain the title compound (199.5 g).

(Intermediate Z-1: Rf (TLC)=0.43 (hexane:ethyl acetate=2:1))

Reference Example Z-2: Methyl 5-(2-(1-(((2-chloroethyl)thio)carbonyl)hydrazinyl)ethyl)thiophene-2-carboxylate (Intermediate Z-2)

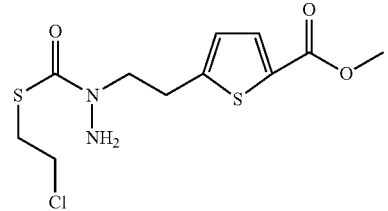

[Formula 83]

To the intermediate Z-1 (199 g), a 4 mol/L solution of hydrogen chloride in dioxane (800 mL) was added, and the mixture was stirred at room temperature for 18 hours. The solvent was evaporated under reduced pressure, and then dichloromethane (6 L), and saturated aqueous sodium hydrogencarbonate (2 L) were added to the residue for extraction. The organic layer was washed with saturated brine (2 L), and dried, and then the solvent was evaporated under reduced pressure to obtain the title compound (172 g).

(Intermediate A-4: Rf (TLC)=0.49 (heptane:ethyl acetate=1:1))

Reference Example Z-3: Methyl 5-(2-(2-oxo-1,3,4-thiadiazinan-3-yl)ethyl)thiophene-2-carboxylate (Intermediate Z-3)

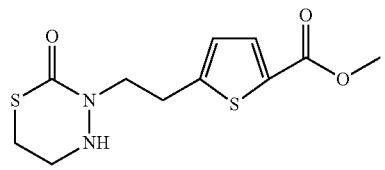

[Formula 84]

To a solution of the intermediate Z-2 (172 g) in acetonitrile (3.4 L), sodium hydrogencarbonate (223 g), and sodium iodide (397 g) were successively added, and the mixture was stirred at 75° C. for 15 hours. The mixture was further stirred at 83° C. for 15 hours, and then cooled to room temperature. The reaction mixture was filtered by using filter paper, and the residue remained on the filter paper was washed with acetonitrile (1 L), combined with the filtrate, and concentrated under reduced pressure. To the residue obtained after the concentration, dichloromethane (3 L) was added, and then the mixture was filtered by using filter paper, the residue remained on the filter paper was washed with dichloromethane (1 L), combined with the filtrate, and concentrated under reduced pressure. The resulting residue was purified by column chromatography (hexane/ethyl acetate), and then concentrated under reduced pressure. The residue was dissolved in ethyl acetate (1 L) by warming, then heptane was added to the solution, and the mixture was cooled on ice. The deposited solid was collected by filtration to obtain the title compound (97 g).

$^1$H-NMR (CDCl$_3$): δ (ppm) 7.64 (1H, d, J=3.8 Hz), 6.88 (1H, d, J=3.8 Hz), 3.86 (3H, s), 3.85 (2H, t, 7.0 Hz), 3.30 (2H, t, J=7.0 Hz), 3.25-3.17 (4H, m), 3.16 (2H, t, J=7.0 Hz)

Reference Example C-2: 2-(3-Bromophenyl)-N-methoxy-N-methylacetamide (Intermediate C-2)

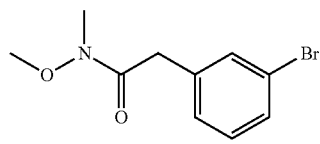

[Formula 85]

A solution of diisopropylethylamine (800 mL) in dichloromethane (1.8 L) was cooled on ice, 3-bromophenylacetic acid (313 g, TCI), N,O-dimethylhydroxylamine hydrochloride (284 g), 1-ethyl-3-(3-dimethylaminopropyl)carbodiimide hydrochloride (334 g), and N,N-dimethyl-4-aminopyridine (18 g) were successively added, and the mixture was stirred at room temperature for 12.5 hours. To the reaction mixture, water (630 mL) and dichloromethane (630 mL) were added, and then the organic layer was successively washed twice with 2 mol/L hydrochloric acid (630 mL), and once each with saturated aqueous sodium hydrogencarbonate (630 mL), and saturated brine (630 mL). The organic layer was dried, and then the solvent was evaporated under reduced pressure to obtain the title compound (372 g).

(Intermediate C-2: LCMS m/z 257.9 (MH$^+$), retention time 1.37 minutes, LC conditions NLC-1)

$^1$H-NMR (CDCl$_3$): δ (ppm) 7.46-7.44 (1H, m), 7.39-7.36 (1H, m), 7.25-7.15 (2H, m), 3.74 (2H, s), 3.64 (3H, s), 3.20 (3H, s)

Reference Example C-3: 1-(3-Bromophenyl)but-3-en-2-one (Intermediate C-3)

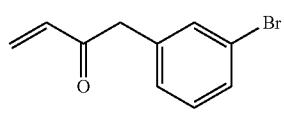

[Formula 86]

A solution of the intermediate C-2 (104.2 g) in tetrahydrofuran (2.1 L) was cooled to −45° C. under a nitrogen atmosphere. To the reaction mixture, vinylmagnesium bromide (1 mol/L solution in tetrahydrofuran, 605 mL, Aldrich) was added over 30 minutes, and the mixture was warmed to 0° C., and then stirred for 1.5 hours. The reaction mixture was added to a mixture of ice water (1 L), and 2 mol/L hydrochloric acid (1 L), and the mixture was stirred for 1 minute. Isopropyl ether (2 L) was added for extraction, and the organic layer was successively washed with 1 mol/L hydrochloric acid (1 L), water (1 L), and saturated brine (1 L), and dried. The solvent was evaporated under reduced pressure to obtain the title compound (92.1 g).

(Intermediate C-3: Rf (TLC)=0.74 (heptane:ethyl acetate=2:1))

Reference Example C-2-2: 2-(3-Iodophenyl)-N-methoxy-N-methylacetamide (Intermediate C-2-2)

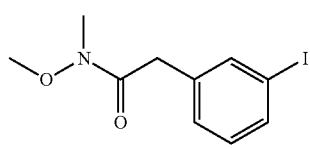

[Formula 87]

The intermediate C-2-2 was synthesized according to the method described in Reference Example C-2 by using 3-iodophenylacetic acid (2.85 g) instead of 3-bromophenylacetic acid, and thus the title compound (3.07 g) was obtained.

(Intermediate C-2-2: Rf (TLC)=0.42 (hexane:ethyl acetate=1:2))

When the compound is synthesized according to the method described above, amount of the reagents, amount of the solvent, reaction time and the like can be appropriately changed according to the equivalent amount of the starting material to be used in light of common knowledge of those skilled in the art. The same shall apply to the following examples.

Reference Example C-3-2: 1-(3-Iodophenyl)but-3-en-2-one (Intermediate C-3-2)

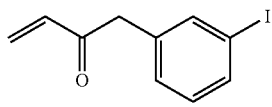

[Formula 88]

The intermediate C-3-2 was synthesized according to the method described in Reference Example C-3 by using the intermediate C-2-2 (100 mg) instead of the intermediate C-2, and thus the title compound (58.7 mg) was obtained.

(Intermediate C-3-2: Rf (TLC)=0.60 (hexane:ethyl acetate=1:2))

Reference Example Z-4: Methyl 5-(2-(4-(4-(3-bromophenyl)-3-oxobutyl)-2-oxo-1,3,4-thiadiazinan-3-yl)ethyl)thiophene-2-carboxylate (Intermediate Z-4)

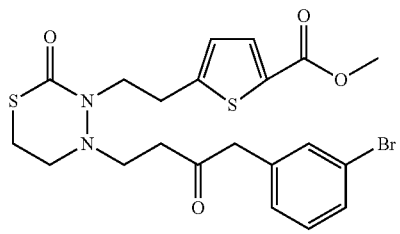

[Formula 89]

To a solution of the intermediate Z-3 (44.4 g) in ethanol (444 mL), the intermediate C-3 (92.1 g) was added, and the mixture was stirred at 110° C. for 40 hours. The reaction mixture was decompressed to evaporate the solvent. The resulting residue was purified by column chromatography (toluene/ethyl acetate) to obtain the title compound (75.9 g).

(Intermediate Z-4: LCMS m/z 511.2 (MH$^+$), retention time 1.75 minutes, LC conditions NLC-1)

Reference Example Z-4-2: Methyl 5-(2-(4-(4-(3-iodophenyl)-3-oxobutyl)-2-oxo-1,3,4-thiadiazinan-3-yl)ethyl)thiophene-2-carboxylate (Intermediate Z-4-2)

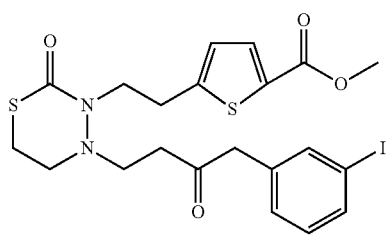

[Formula 90]

The intermediate Z-4-2 was synthesized according to the method described in Reference Example Z-4 by using the intermediate C-3-2 (680.2 mg) instead of the intermediate C-3, and thus the title compound (120.1 mg) was obtained.

(Intermediate Z-4-2: Rf (TLC)=0.50 (hexane:ethyl acetate=1:2), LCMS m/z 559.0 (MH$^+$), retention time 1.84 minutes, LC conditions LC-1)

Reference Example Z-5: Methyl 5-(2-(4-(4-(3-bromophenyl)-3-hydroxybutyl)-2-oxo-1,3,4-thiadiazinan-3-yl)ethyl)thiophene-2-carboxylate (Intermediate Z-5)

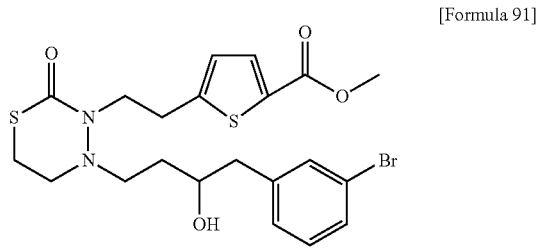

[Formula 91]

A solution of the intermediate Z-4 (75.7 g) in methanol (1.14 L) was cooled to 0° C., and sodium borohydride (7.47 g) was added portionwise to the solution. The mixture was stirred at 0° C. for 1 hour, and then diluted hydrochloric acid was added portionwise to the reaction mixture until the reaction mixture became neutral. The organic solvent was evaporated under reduced pressure, then ethyl acetate (2 L) was added to the residue, the mixture was cooled to 0° C., saturated aqueous sodium hydrogencarbonate (1 L) was added to the mixture portionwise, and the resulting mixture was stirred for 5 minutes. The organic layer was extracted, and dried, and then the solvent was evaporated under reduced pressure to obtain the title compound (71.0 g).

(Intermediate Z-5: LCMS m/z 513.15 (MH$^+$), retention time 1.70 minutes, LC conditions LC-1)

Reference Example Z-14: Methyl 5-(2-(2-oxo-4-(3-oxo-4-(3-(thiophen-3-ylethynyl)phenyl)butyl)-1,3,4-thiadiazinan-3-yl)ethyl)thiophene-2-carboxylate (Intermediate Z-14)

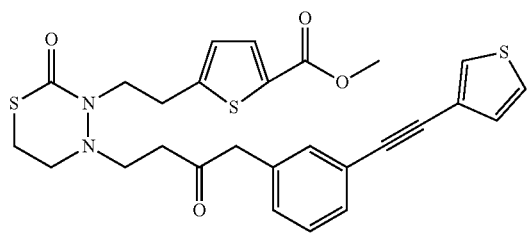

[Formula 92]

To the intermediate Z-4-2 (86.6 mg), diethylamine (78 μL), 3-ethynylthiophene (21 μL), copper(I) iodide (0.8 mg), and tetrakis(triphenylphosphine)palladium (1.1 mg) were successively added, and the mixture was stirred at room temperature for 2 hours. Further, diethylamine (600 μL), copper(I) iodide (1.5 mg), and tetrakis(triphenyl-phosphine)palladium (2.0 mg) were successively added, and the mixture was stirred at room temperature for 12 hours. To the reaction mixture, diethyl ether, and 1 mol/L hydrochloric acid (0.5 mL) were added, and the organic layer was successively washed 5 times with 1 mol/L hydrochloric acid (1 mL), and once with saturated aqueous sodium hydrogencarbonate (0.5 mL), and dried. The solvent was evaporated under reduced pressure, and the resulting residue was purified by column chromatography (hexane/ethyl acetate) to obtain the title compound (31.7 mg).

(Intermediate Z-14: Rf (TLC)=0.12 (hexane:ethyl acetate=1:2), LCMS m/z 539.1 (MH$^+$), retention time 1.95 minutes, LC conditions LC-1)

Reference Example Z-17: Methyl 5-(2-(4-(3-hydroxy-4-(3-(thiophen-3-ylethynyl)phenyl)butyl)-2-oxo-1,3,4-thiadiazinan-3-yl)ethyl)thiophene-2-carboxylate (Intermediate Z-17)

[Formula 93]

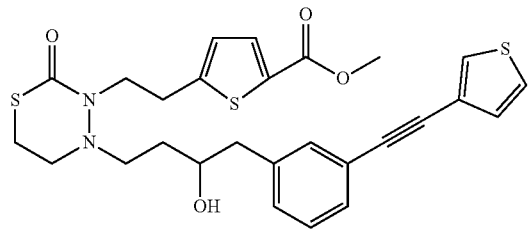

The intermediate Z-17 was synthesized according to the method described in Reference Example Z-5 by using the intermediate Z-14 (31.7 mg) instead of the intermediate Z-4, and thus the title compound (31.8 mg) was obtained.

(Intermediate Z-17: LCMS m/z 541.1 (MH$^+$), retention time 1.90 minutes, LC conditions LC-1)

Example 1: 5-(2-(4-(3-Hydroxy-4-(3-(thiophen-3-ylethynyl)phenyl)butyl)-2-oxo-1,3,4-thiadiazinan-3-yl)ethyl)thiophene-2-carboxylic Acid

[Formula 94]

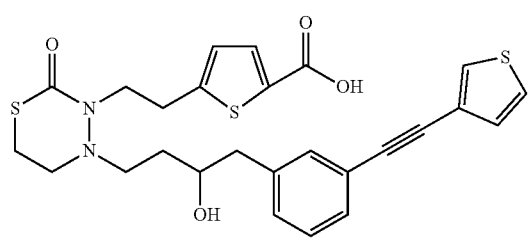

To a solution of the intermediate Z-17 (31.8 mg) in tetrahydrofuran (884 μL), water (221 μL), and 2 mol/L aqueous lithium hydroxide (442 μL) were added, and the mixture was stirred at 50° C. for 17.5 hours. The reaction mixture was cooled to 0° C., 2 mol/L hydrochloric acid (660 μL) was added to the mixture, and then the resulting mixture was extracted with ethyl acetate. The solvent was evaporated under reduced pressure, and the resulting residue was purified by thin layer chromatography (hexane/ethyl acetate) to obtain the title compound (22.7 mg).

(LCMS m/z 527.2 (MH$^+$), retention time 1.68 minutes, LC conditions LC-1)

Reference Example A-10: (3-Bromothiophen-2-yl)methanol (Intermediate A-10)

[Formula 95]

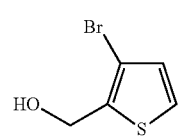

A solution of 3-bromothiophene-2-carboxylic acid (3.0 g, Aldrich) in tetrahydrofuran (46 mL) was cooled to 0° C. under a nitrogen gas atmosphere, a 1 mol/L solution of borane-tetrahydrofuran complex in tetrahydrofuran (26.1 mL) was added dropwise to the solution over 15 minutes, and then the mixture was stirred at room temperature for 21.5 hours. The reaction mixture was cooled to 0° C., ice water, 1 mol/L hydrochloric acid, and ethyl acetate were added to the mixture, and the resulting mixture was stirred. The organic solvent was evaporated under reduced pressure, then ethyl acetate was added to the residue, and the organic layer was successively washed with 1 mol/L hydrochloric acid, saturated aqueous sodium hydrogencarbonate, and saturated brine, and dried. The solvent was evaporated under reduced pressure to obtain the title compound (2.87 g).

(Intermediate A-10: Rf (TLC)=0.42 (hexane:ethyl acetate=2:1))

Reference Example A-11: 3-Bromo-2-(bromomethyl)thiophene (Intermediate A-11)

[Formula 96]

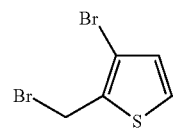

A solution of the intermediate A-10 (7.14 g) in dichloromethane (169 mL) was cooled to 0° C., triphenylphosphine (13.3 g), and carbon tetrabromide (13.45 g) were added to the solution, and the mixture was stirred at room temperature for 2.75 hours. To the reaction mixture, saturated aqueous sodium hydrogencarbonate was added, and then the organic solvent was evaporated under reduced pressure. Ethyl acetate was added the residue, and then the organic layer was successively washed with saturated aqueous sodium hydrogencarbonate, and saturated brine, and dried. The organic solvent was evaporated under reduced pressure, then a mixed solvent of hexane and ethyl acetate (8:1) was added to the resulting residue to prepare a suspension, and the suspension was filtered with filter paper covered with silica gel. The solvent of the filtrate was

Reference Example A-12: 2-(3-Bromothiophen-2-yl)acetonitrile (Intermediate A-12)

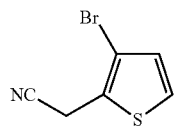
[Formula 97]

To the intermediate A-11 (9.70 g), dimethyl sulfoxide (28 mL), and acetonitrile (140 mL) were added, the mixture was cooled to 0° C., then sodium cyanide (2.15 g) was added to the mixture, and the resulting mixture was stirred at room temperature for 16 hours. To the reaction mixture, saturated aqueous sodium hydrogencarbonate was added, and the mixture was stirred, and then concentrated under reduced pressure. The reaction mixture was filtered through filter paper covered with Celite, and the residue remained on Celite was washed with ethyl acetate. The filtrate and the wash liquid were mixed, and the organic layer was successively washed with saturated aqueous sodium hydrogencarbonate, and saturated brine, and dried. The organic solvent was evaporated under reduced pressure, and then the resulting residue was purified by column chromatography (hexane/ethyl acetate) to obtain the title compound (3.89 g).

(Intermediate A-12: Rf (TLC)=0.18 (hexane:ethyl acetate=8:1))

Reference Example A-13: Ethyl 2-(3-bromothiophen-2-yl)acetate (Intermediate A-13)

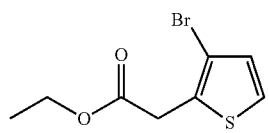
[Formula 98]

To a solution of the intermediate A-12 (3.89 g) in ethanol (32.3 mL), water (0.4 mL) was added, the mixture was cooled to 0° C., and then concentrated sulfuric acid (5.63 mL) was added to the mixture portionwise. The reaction mixture was stirred at 85° C. for 115 hours, and then cooled to 0° C., and saturated aqueous sodium hydrogencarbonate was added until the reaction mixture became neutral. Ethyl acetate was added to the reaction mixture, and the resulting mixture was stirred, and then concentrated under reduced pressure. Ethyl acetate was added to the reaction mixture, and the organic layer was successively washed with saturated aqueous sodium hydrogencarbonate, and saturated brine, and dried. The solvent was evaporated under reduced pressure to obtain the title compound (4.40 g).

(Intermediate A-13: Rf (TLC)=0.33 (hexane:ethyl acetate=8:1))

Reference Example A-14: 2-(3-Bromothiophen-2-yl)ethanol (Intermediate A-14)

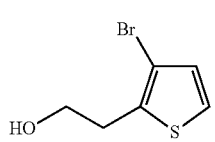
[Formula 99]

A solution of the intermediate A-13 (4.40 g) in tetrahydrofuran (88.5 mL) was cooled to 0° C. under a nitrogen gas atmosphere, lithium aluminum hydride (672 mg) was added to the solution, and the mixture was stirred for 0.6 hour. To the reaction mixture, ice water, 1 mol/L hydrochloric acid, and ethyl acetate were added, and the resulting mixture was stirred, and then the organic layer was successively washed with 1 mol/L hydrochloric acid, saturated aqueous sodium hydrogencarbonate, and saturated brine, and dried. The solvent was evaporated under reduced pressure, and the resulting residue was purified by column chromatography (hexane/ethyl acetate) to obtain the title compound (2.69 g).

(Intermediate A-14: Rf (TLC)=0.23 (hexane:ethyl acetate=4:1))

Reference Example A-2-2: (2-(3-Bromothiophen-2-yl)ethoxy)(tert-butyl)dimethylsilane (Intermediate A-2-2)

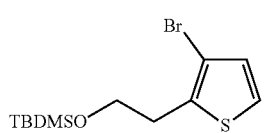
[Formula 100]

The intermediate A-2-2 was synthesized according to the method described in Reference Example A-2 by using the intermediate A-14 (2.69 g) instead of 2-(thiophen-2-yl)ethanol, and thus the title compound (3.93 g) was obtained.

(Intermediate A-2-2: Rf (TLC)=0.76 (hexane:ethyl acetate=4:1))

Reference Example A-3-2: 4-Bromo-5-(2-((tert-butyldimethylsilyl)oxy)ethyl)thiophene-2-carboxylic Acid (Intermediate A-3-2)

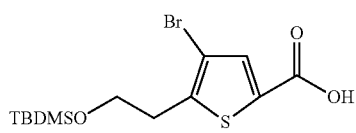
[Formula 101]

The intermediate A-3-2 was synthesized according to the method described in Reference Example A-3 by using the intermediate A-2-2 (293 mg) instead of the intermediate A-2, and lithium diisopropylamide (1.09 mol/L solution in hexane/tetrahydrofuran, 928 µL, KANTO) instead of n-butyllithium (2.6 mol/L solution in hexane, KANTO), and thus the title compound (339 mg) was obtained.

(Intermediate A-3-2: Rf (TLC)=0.12 (hexane:ethyl acetate=1:1))

Reference Example A-4-2: Methyl 4-bromo-5-(2-hydroxyethyl)thiophene-2-carboxylate (Intermediate A-4-2)

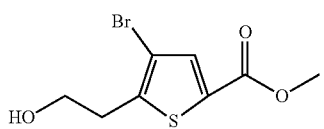

[Formula 102]

The intermediate A-4-2 was synthesized according to the method described in Reference Example A-4 by using the intermediate A-3-2 (377 mg) instead of the intermediate A-3, and thus the title compound (217 mg) was obtained.

(Intermediate A-4-2: Rf (TLC)=0.53 (hexane:ethyl acetate=1:1))

Reference Example A-5-2: Methyl 4-bromo-5-(2-bromoethyl)thiophene-2-carboxylate (Intermediate A-5-2)

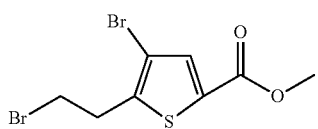

[Formula 103]

The intermediate A-5-2 was synthesized according to the method described in Reference Example A-5 by using the intermediate A-4-2 (217 mg) instead of the intermediate A-4, and thus the title compound (315 mg) was obtained.

(Intermediate A-5-2: Rf (TLC)=0.44 (hexane:ethyl acetate=8:1))

Reference Example A-6-2: tert-Butyl 2-(2-(3-bromo-5-(methoxycarbonyl)thiophen-2-yl)ethyl) hydrazinecarboxylate (Intermediate A-6-2)

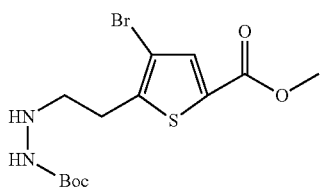

[Formula 104]

The intermediate A-6-2 was synthesized according to the method described in Reference Example A-6 by using the intermediate A-5-2 (315 mg) instead of the intermediate A-5, and thus the title compound (168 mg) was obtained.

(Intermediate A-5-2: Rf (TLC)=0.48 (hexane:ethyl acetate=1:1))

Reference Example Z-1-2: tert-Butyl 2-(2-(3-bromo-5-(methoxycarbonyl)thiophen-2-yl)ethyl)-2-(((2-chloroethyl)thio)carbonyl)hydrazinecarboxylate (Intermediate Z-1-2)

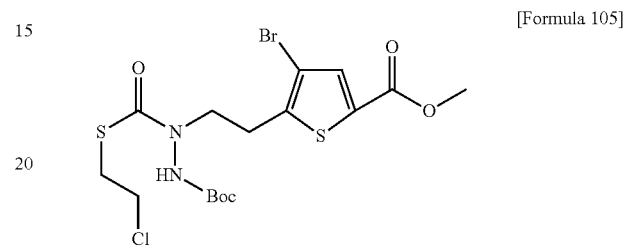

[Formula 105]

To a solution of the intermediate A-6-2 (1.98 g) in dichloromethane (13.1 mL), sodium hydrogencarbonate (880 mg) was added, the mixture was cooled to 0° C., and then the intermediate B-3 (993 mg) was added portionwise to the mixture. The resulting mixture was stirred at room temperature for 0.5 hour, then water and ethyl acetate were added to the reaction mixture, and the organic layer was successively washed with saturated aqueous sodium hydrogencarbonate, and saturated brine, and dried. The solvent was evaporated under reduced pressure to obtain the title compound (796 mg).

(Intermediate Z-1-2: Rf (TLC)=0.53 (toluene:ethyl acetate=8:1))

Reference Example Z-2-2: Methyl 4-bromo-5-(2-(1-(((2-chloroethyl)thio)carbonyl)hydrazinyl)ethyl) thiophene-2-carboxylate (Intermediate Z-2-2)

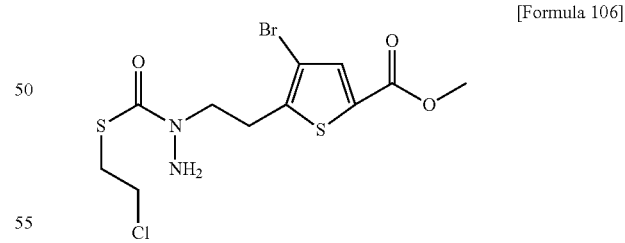

[Formula 106]

To the intermediate Z-1-2 (796 mg), a 4 mol/L solution of hydrogen chloride in dioxane (7.5 mL) was added, and the mixture was stirred at room temperature for 17.6 hours. To the reaction mixture, ethyl acetate, and 5 mol/1 aqueous sodium hydroxide were added, and then saturated aqueous sodium hydrogencarbonate was added to the mixture until the mixture became basic. The organic layer was successively washed with saturated aqueous sodium hydrogencarbonate, and saturated brine, and dried, and then the solvent was evaporated under reduced pressure to obtain the title compound (594 mg).

(Intermediate Z-2-2: Rf (TLC)=0.42 (toluene:ethyl acetate=8:1))

Reference Example Z-3-2: Methyl 4-bromo-5-(2-(2-oxo-1,3,4-thiadiazinan-3-yl)ethyl)thiophene-2-carboxylate (Intermediate Z-3-2)

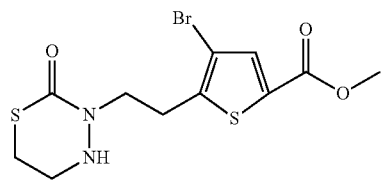

[Formula 107]

To a solution of the intermediate Z-2-2 (594 mg) in acetonitrile (14.9 mL), sodium hydrogencarbonate (626 mg), and sodium iodide (1.12 g) were successively added, and the mixture was stirred at 85° C. for 120 hours. The reaction mixture was cooled to room temperature, and then ethyl acetate, and water were added to the mixture for extraction. The organic layer was successively washed with saturated aqueous sodium hydrogencarbonate, and saturated brine, and dried, then the solvent was evaporated under reduced pressure, and the resulting residue was purified by column chromatography (hexane/ethyl acetate) to obtain the title compound (374 mg).

(Intermediate Z-3-2: Rf (TLC)=0.13 (hexane:ethyl acetate=2:1))

Reference Example C-4: N-Methoxy-N-methyl-2-(3-(thiophen-3-ylethynyl)-phenyl)acetamide (Intermediate C-4)

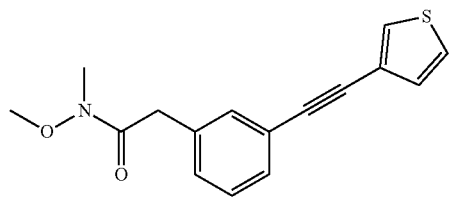

[Formula 108]

To a solution of the intermediate C-2-2 (1.0 g) in acetonitrile (26 mL), bis(acetonitrile)palladium chloride (43 mg), 2-dicyclohexylphosphino-2',4',6'-triisopropylbiphenyl (243 mg), cesium carbonate (2.1 g), and 3-ethynylthiophene (650 μL) were successively added, and the mixture was stirred at 60° C. for 14 hours under a nitrogen gas atmosphere. The reaction mixture was filtered through filter paper covered with Celite, and the residue remained on Celite was washed with ethyl acetate. The filtrate and the wash liquid were mixed, the organic solvent was evaporated under reduced pressure, and then the resulting residue was purified by column chromatography (hexane/ethyl acetate) to obtain the title compound (850 mg).

(Intermediate C-4: Rf (TLC)=0.40 (hexane:ethyl acetate=1:1), LCMS m/z 286.13 (MH$^+$), retention time 1.70 minutes, LC conditions LC-1)

Reference Example Z-14-2: Methyl 4-bromo-5-(2-(2-oxo-4-(3-oxo-4-(3-(thiophen-3-ylethynyl)phenyl)butyl)-1,3,4-thiadiazinan-3-yl)ethyl)thiophene-2-carboxylate (Intermediate Z-14-2)

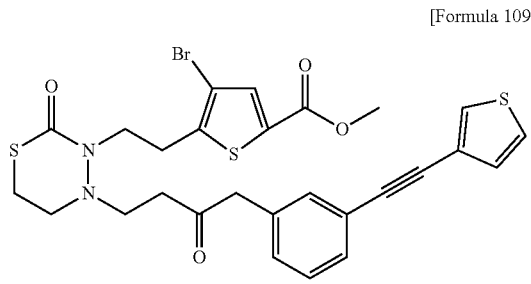

[Formula 109]

A solution of the intermediate C-4 (117 mg) in 1,2-dimethoxyethane (2.3 mL) was cooled to 0° C. under a nitrogen atmosphere. To the reaction mixture, vinylmagnesium bromide (1 mol/L solution in tetrahydrofuran, 620 μL, Aldrich) was added, and the resulting mixture was stirred for 3 hours. To the reaction mixture, 2 mol/L hydrochloric acid was added, and the resulting mixture was stirred for 1 minute. Ethyl acetate was added to the reaction mixture for extraction, the organic layer was dried, and then the solvent was evaporated under reduced pressure. To the resulting residue, ethanol (3 mL), water (3 mL), and the intermediate Z-3-2 (100 mg) were added, and the mixture was stirred at 110° C. for 18 hours. To the reaction mixture, saturated brine, and chloroform were added for extraction, the organic layer was dried, and then the solvent was evaporated under reduced pressure. The resulting residue was purified by column chromatography (hexane/ethyl acetate) to obtain the title compound (156.1 mg).

(Intermediate Z-14-2: LCMS m/z 617.2 (MH$^+$), retention time 2.08 minutes, LC conditions LC-1)

Example 2: 4-Bromo-5-(2-(4-(3-hydroxy-4-(3-(thiophen-3-ylethynyl)phenyl)butyl)-2-oxo-1,3,4-thiadiazinan-3-yl)ethyl)thiophene-2-carboxylic Acid

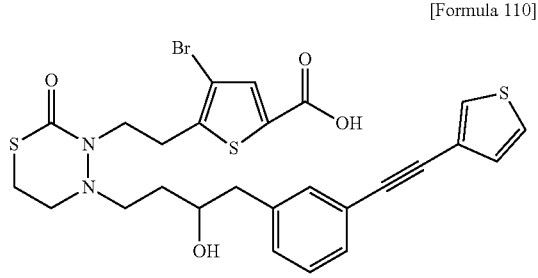 [SMILES: O=C(O)c1cc(Br)c(CCN2C(=O)SCCN2CCC(O)Cc2cccc(C#Cc3ccsc3)c2)s1]

[Formula 110]

A solution of the intermediate Z-14-2 (156.1 mg) in methanol (3 mL) was cooled to 0° C., and sodium borohydride (17.3 mg) was added portionwise to the solution. The resulting mixture was stirred at 0° C. for 1 hour, and then diluted hydrochloric acid was added portionwise to the mixture until the reaction mixture became neutral. The organic solvent was evaporated under reduced pressure, then ethyl acetate (2 L) was added to the residue, the mixture was cooled to 0° C., saturated aqueous sodium hydrogencarbonate (1 L) was added portionwise to the mixture, and the resulting mixture was stirred for 5 minutes. The organic layer was extracted, and dried, and then the solvent was evaporated under reduced pressure. To the resulting residue, tetrahydrofuran (4.6 mL), methanol (4.6 mL), and 1 mol/L aqueous sodium hydroxide (4.6 mL) were added, and the mixture was stirred at room temperature for 3 hours. The reaction mixture was cooled to 0° C., 2 mol/L hydrochloric acid was added to the reaction mixture, then the resulting mixture was extracted with ethyl acetate, and the organic layer was dried. The solvent was evaporated under reduced pressure, and the resulting residue was purified by column chromatography (chloroform/methanol) to obtain the title compound (140 mg).

(LCMS m/z 605.1 (MH$^+$), retention time 1.78 minutes, LC conditions LC-1)

Reference Example Z-14-3: Methyl 5-(2-(2-oxo-4-(3-oxo-4-(3-(thiophen-2-ylethynyl)phenyl)butyl)-1,3,4-thiadiazinan-3-yl)ethyl)thiophene-2-carboxylate (Intermediate Z-14-3)

[Formula 111]

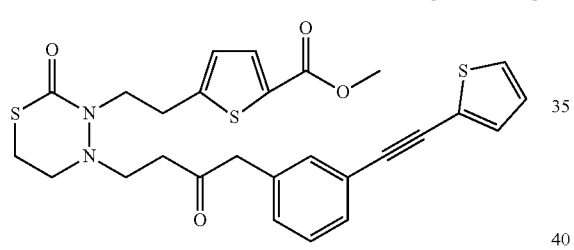

The intermediate Z-14-3 was synthesized according to the method described in Reference Example Z-14 by using 2-ethynylthiophene (33.6 mg, MAYBRIDGE) instead of 3-ethynylthiophene, and thus the title compound (32.9 mg) was obtained.

(Intermediate Z-14-3: LCMS m/z 539.0 (MH$^+$), retention time 2.00 minutes, LC conditions LC-1)

Example 3: 5-(2-(4-(3-Hydroxy-4-(3-(thiophen-2-ylethynyl)phenyl)butyl)-2-oxo-1,3,4-thiadiazinan-3-yl)ethyl)thiophene-2-carboxylic Acid

[Formula 112]

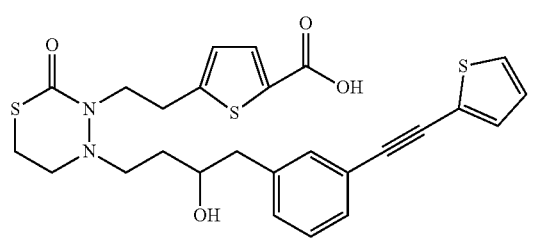

A solution of the intermediate Z-14-3 (32.9 mg) in methanol (0.6 mL) was cooled to 0° C., and sodium borohydride (3.6 mg) was added portionwise to the solution. The mixture was stirred at 0° C. for 1.5 hours, and then diluted with ethyl acetate, and diluted hydrochloric acid (1.5 mL) was added to the mixture. Saturated aqueous sodium hydrogencarbonate was added to the mixture until the mixture became neutral. The resulting mixture was extracted with ethyl acetate, the organic layer was dried, and then the solvent was evaporated under reduced pressure. To the resulting residue, tetrahydrofuran (920 µL), water (230 µL), and 2 mol/L aqueous sodium hydroxide (460 µL) were added, and the resulting mixture was stirred at 50° C. for 14 hours. The reaction mixture was cooled to 0° C., and left standing for 5.5 hours, then 2 mol/L hydrochloric acid was added to the mixture, the mixture was extracted with ethyl acetate, and the organic layer was dried. The solvent was evaporated under reduced pressure, and the resulting residue was purified by liquid chromatography (acetonitrile/water) to obtain the title compound (3.6 mg).

(LCMS m/z 527.0 (MH$^+$), retention time 1.79 minutes, LC conditions LC-1)

Reference Example Z-6: Methyl 5-(2-(4-(4-(3-bromophenyl)-3-((tert-butyldimethylsilyl)oxy)butyl)-2-oxo-1,3,4-thiadiazinan-3-yl)ethyl)thiophene-2-carboxylate (Intermediate Z-6)

[Formula 113]

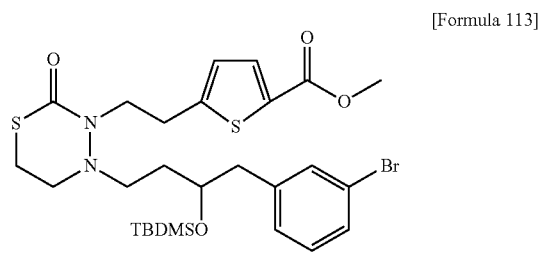 [SMILES: COC(=O)c1ccc(CCN2C(=O)SCCN2CCC(Cc2cccc(Br)c2)O[Si](C)(C)C(C)(C)C)s1]

To a solution of the intermediate Z-5 (1.0 g) in N,N-dimethylformamide (19.5 mL), imidazole (265 mg), and tert-butyldimethylchlorosilane (596 mg) were added, and the resulting mixture was stirred at 30° C. for 15 hours. To the reaction mixture, saturated aqueous sodium hydrogencarbonate was added, and the resulting mixture was extracted with ethyl acetate. The organic layer was washed with saturated brine, and then dried, the solvent was evaporated under reduced pressure, and the resulting residue was purified by column chromatography (hexane/ethyl acetate) to obtain the title compound (1.16 g).

(Intermediate Z-6: LCMS m/z 627.0 (MH+), retention time 2.53 minutes, LC conditions LC-1)

Reference Example Z-21: Methyl 5-(2-(4-(3-((tert-butyldimethylsilyl)oxy)-4-(3-((trimethylsilyl)ethynyl)phenyl)butyl)-2-oxo-1,3,4-thiadiazinan-3-yl)ethyl)thiophene-2-carboxylate (Intermediate Z-21)

[Formula 114]

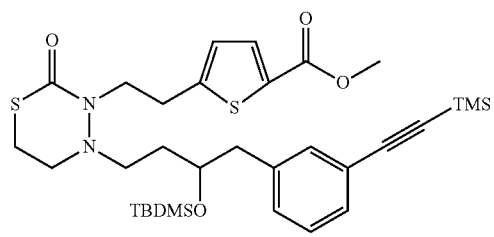

To a solution of the intermediate Z-6 (300 mg) in acetonitrile (15.3 mL), bis(acetonitrile)palladium chloride (12.4 mg), 2-dicyclohexylphosphino-2',4',6'-triisopropylbiphenyl (68.3 mg), cesium carbonate (311 mg), and ethynyltrimethylsilane (331 μL) were successively added, and the resulting mixture was stirred at 60° C. for 19 hours under a nitrogen gas atmosphere. To the reaction mixture, ethynyltrimethylsilane (199 μL), bis(acetonitrile)palladium chloride (6.2 mg), 2-dicyclohexylphosphino-2',4',6'-triisopropylbiphenyl (34.1 mg), and cesium carbonate (187 mg) were added, and the resulting mixture was stirred at 60° C. for 3.75 hours. The solvent of the reaction mixture was evaporated under reduced pressure, and then the resulting residue was purified by column chromatography (hexane/ethyl acetate) to obtain the title compound (245 mg).

(Intermediate Z-21: LCMS m/z 645.4 (MH+), retention time 2.35 minutes, LC conditions LC-6)

Reference Example Z-22: Methyl 5-(2-(4-(3-((tert-butyldimethylsilyl)oxy)-4-(3-ethynylphenyl)butyl)-2-oxo-1,3,4-thiadiazinan-3-yl)ethyl)thiophene-2-carboxylate (Intermediate Z-22)

[Formula 115]

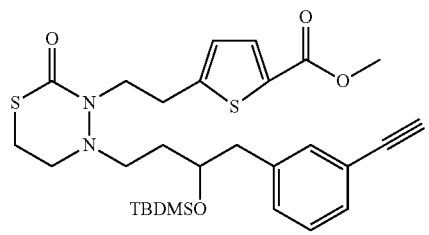

To a solution of the intermediate Z-21 (225 mg) in methanol (3.6 mL), potassium carbonate (50 mg) was added, and the mixture was stirred at room temperature for 1 hour. The reaction mixture was filtered, and the filtrate was combined with the methanol wash liquid used for washing the residue remained on the filter paper, and concentrated. The resulting residue was purified by column chromatography (hexane/ethyl acetate) to obtain the title compound (198 mg).

(Intermediate Z-22: LCMS m/z 573.3 (MH+), retention time 1.37 minutes, LC conditions LC-6)

Example 4: 5-(2-(4-(3-Hydroxy-4-(3-((4-methylthiophen-3-yl)ethynyl)phenyl)butyl)-2-oxo-1,3,4-thiadiazinan-3-yl)ethyl)thiophene-2-carboxylic Acid

[Formula 116]

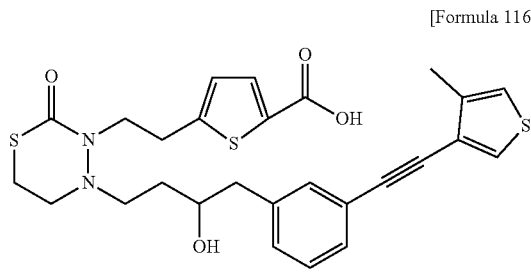

[Step a]

Methyl 5-(2-(4-(3-((tert-butyldimethylsilyl)oxy)-4-(3-((4-methylthiophen-3-yl)ethynyl)phenyl)butyl)-2-oxo-1,3,4-thiadiazinan-3-yl)ethyl)thiophene-2-carboxylate (Intermediate Z-7-4)

[Formula 117]

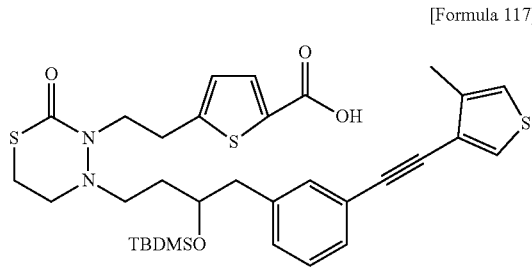

To a solution of the intermediate Z-22 (10 mg) in acetonitrile (280 μV, bis(acetonitrile)palladium chloride (0.5 mg), 2-dicyclohexylphosphino-2',4',6'-triisopropylbiphenyl (2.5 mg), cesium carbonate (6.8 mg), and 3-bromo-4-methylthiophene (9.3 mg, TCI) were successively added, and the resulting mixture was stirred at 60° C. for 4 hours under a nitrogen gas atmosphere. The reaction mixture was filtered through filter paper covered with Celite, and the residue remained on Celite was washed with ethyl acetate. The filtrate and the wash liquid were mixed, and the organic layer was successively washed with water, and saturated brine, and then dried. The solvent was evaporated under reduced pressure, and then the resulting residue was purified by column chromatography (hexane/ethyl acetate) to obtain the title compound (7.4 mg).

(Intermediate Z-7-4: LCMS m/z 699.4 (MH+), retention time 2.18 minutes, LC conditions LC-6)

[Step b]

5-(2-(4-(3-Hydroxy-4-(3-((4-methylthiophen-3-yl) ethynyl)phenyl)butyl)-2-oxo-1,3,4-thiadiazinan-3-yl) ethyl)thiophene-2-carboxylic Acid A solution of the intermediate Z-7-4 (7.4 mg) in tetrahydrofuran (390 μL) was cooled to 0° C., tetrabutylammonium fluoride (1 mol/L solution in tetrahydrofuran, 33 μL) was added to the solution, and the resulting mixture was stirred at room temperature for 2.5 hours. To the reaction mixture, methanol (390 μl), and 1 mol/L aqueous sodium hydroxide (390 μL) were added, and the resulting mixture was stirred at room temperature for 2 hours. To the reaction mixture, 2 mol/L hydrochloric acid (100 μL), and water (400 μL) were added, the mixture was extracted 5 times with ethyl acetate (1 mL), and then the organic layer was dried. The solvent was evaporated under reduced pressure, and the resulting residue was purified by column chromatography (chloroform/methanol) to obtain the title compound (4.9 mg).

(LCMS m/z 541.2 (MH+), retention time 1.74 minutes, LC conditions LC-1)

Example 5: 5-(2-(4-(4-(3-((2-Chlorothiophen-3-yl) ethynyl)phenyl)-3-hydroxybutyl)-2-oxo-1,3,4-thiadiazinan-3-yl)ethyl)thiophene-2-carboxylic Acid

[Formula 118]

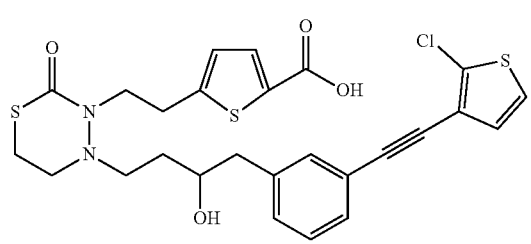

According to the method described in Example 4, synthesis was performed by using 3-bromo-2-chlorothiophene (20.7 mg, TCI) instead of 3-bromo-4-methylthiophene to obtain the title compound (12.9 mg).

(LCMS m/z 561.1 (MH+), retention time 1.77 minutes, LC conditions LC-1)

Example 6: 5-(2-(4-(3-Hydroxy-4-(3-((5-methylthiophen-3-yl)ethynyl)phenyl)butyl)-2-oxo-1,3,4-thiadiazinan-3-yl)ethyl)thiophene-2-carboxylic Acid

[Formula 119]

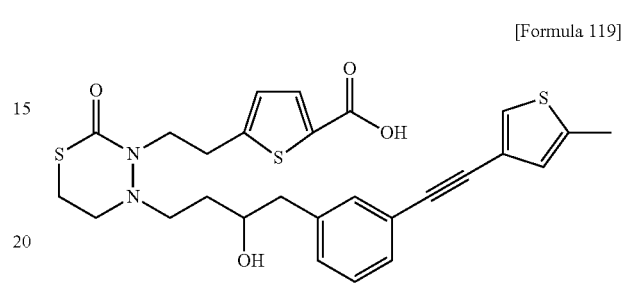

[Step a]

Methyl 5-(2-(4-(3-((tert-butyldimethylsilyl)oxy)-4-(3-((5-methylthiophen-3-yl)ethynyl)phenyl)butyl)-2-oxo-1,3,4-thiadiazinan-3-yl)ethyl)thiophene-2-carboxylate (Intermediate Z-7-6)

[Formula 120]

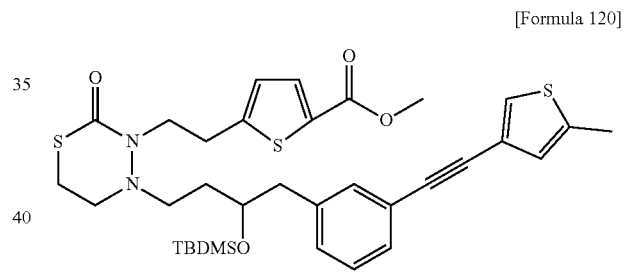

To a solution of the intermediate Z-22 (20 mg) in acetonitrile (1120 μL), bis(acetonitrile)palladium chloride (0.9 mg), 2-dicyclohexylphosphino-2',4',6'-triisopropylbiphenyl (5.0 mg), cesium carbonate (13.7 mg), and 3-bromo-5-methylthiophene (18.5 mg, TCI) were successively added, and the resulting mixture was stirred at 60° C. for 4 hours under a nitrogen gas atmosphere. The reaction mixture was filtered through filter paper covered with Celite, and the residue remained on Celite was washed with a mixed solvent of chloroform and methanol (9:1). The filtrate and the wash liquid were mixed, the solvent was evaporated under reduced pressure, and then the resulting residue was purified by column chromatography (hexane/ethyl acetate) to obtain the title compound (16.2 mg).

(Intermediate Z-7-6: LCMS m/z 699.4 (MH+), retention time 2.20 minutes, LC conditions LC-6)

[Step b]

5-(2-(4-(3-Hydroxy-4-(3-((5-methylthiophen-3-yl) ethynyl)phenyl)butyl)-2-oxo-1,3,4-thiadiazinan-3-yl) ethyl)thiophene-2-carboxylic Acid A solution of the intermediate Z-7-6 (16.2 mg) in tetrahydrofuran (850 μL) was cooled to 0° C., tetrabutylammonium fluoride (1 mol/L solution in tetrahydrofuran, 73 μL) was added, and the mixture was stirred at room temperature for 2.5 hours. To the reaction mixture, 1 mol/L aqueous sodium hydroxide (66 μL) was added, and the resulting mixture was stirred at room temperature for 5 hours. To the reaction mixture, 1 mol/L hydrochloric acid (500 μL) was added, the resulting mixture was extracted 5 times with ethyl acetate (1 mL), and then the organic layer was washed with saturated brine (500 μl), and dried. The solvent was evaporated under reduced pressure to obtain the title compound (22.1 mg).

(LCMS m/z 541.2 (MH$^+$), retention time 1.76 minutes, LC conditions LC-1)

Example 7: 5-(2-(4-(4-(3-((4-Cyanothiophen-3-yl)ethynyl)phenyl)-3-hydroxybutyl)-2-oxo-1,3,4-thiadiazinan-3-yl)ethyl)thiophene-2-carboxylic Acid

[Formula 121]

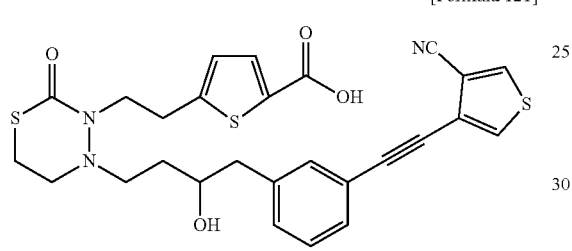

Synthesis was performed according to the method described in Example 6 by using 4-bromothiophene-3-carbonitrile (18.9 mg, COMBI-BLOCKS) instead of 3-bromo-5-methylthiophene to obtain the title compound (3.8 mg).

(LCMS m/z 552.1 (MH$^+$), retention time 1.52 minutes, LC conditions LC-1)

Example 8: 5-(2-(4-(4-(3-((2-Cyanothiophen-3-yl)ethynyl)phenyl)-3-hydroxybutyl)-2-oxo-1,3,4-thiadiazinan-3-yl)ethyl)thiophene-2-carboxylic Acid

[Formula 122]

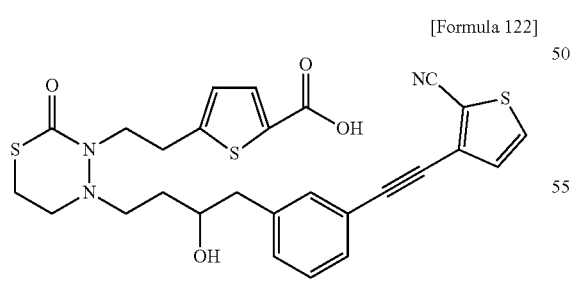

Synthesis was performed according to the method described in Example 6 by using 3-bromothiophene-2-carbonitrile (18.9 mg, APOLLO) instead of 3-bromo-5-methylthiophene to obtain the title compound (5.5 mg).

(LCMS m/z 552.2 (MH$^+$), retention time 1.56 minutes, LC conditions LC-1)

Example 9: 5-(2-(4-(3-Hydroxy-4-(3-(thiazol-4-ylethynyl)phenyl)butyl)-2-oxo-1,3,4-thiadiazinan-3-yl)ethyl)thiophene-2-carboxylic Acid

[Formula 123]

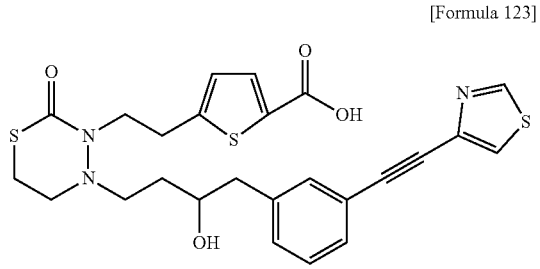 [SMILES: O=C(O)c1ccc(CCN2C(=O)SCCN2CCC(O)Cc2cccc(C#Cc3cscn3)c2)s1]

Synthesis was performed according to the method described in Example 6 by using 4-bromothiazole (17.2 mg, ALDRICH) instead of 3-bromo-5-methylthiophene to obtain the title compound (14.3 mg).

(LCMS m/z 528.2 (MH$^+$), retention time 1.38 minutes, LC conditions LC-1)

Example 10: 5-(2-(4-(4-(3-(Furan-3-ylethynyl)phenyl)-3-hydroxybutyl)-2-oxo-1,3,4-thiadiazinan-3-yl)ethyl)thiophene-2-carboxylic Acid

[Formula 124]

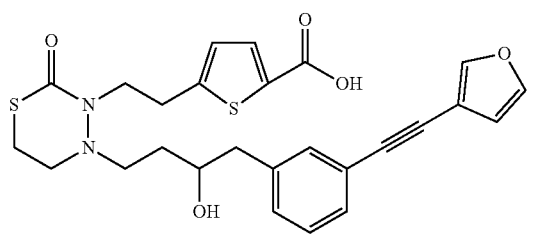

Synthesis was performed according to the method described in Example 6 by using 3-bromofuran (15.4 mg, TCI) instead of 3-bromo-5-methylthiophene to obtain the title compound (13.2 mg).

(LCMS m/z 511.2 (MH$^+$), retention time 1.57 minutes, LC conditions LC-1)

Example 11: 5-(2-(4-(4-(3-(Furan-2-ylethynyl)phenyl)-3-hydroxybutyl)-2-oxo-1,3,4-thiadiazinan-3-yl)ethyl)thiophene-2-carboxylic Acid

[Formula 125]

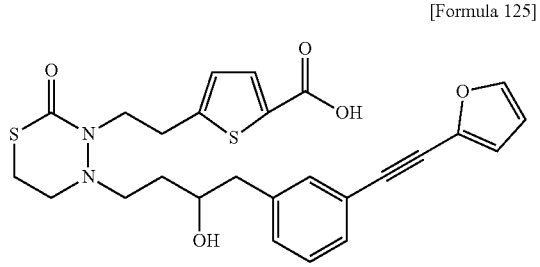

Synthesis was performed according to the method described in Example 6 by using 2-bromofuran (14.8 mg, ALDRICH) instead of 3-bromo-5-methylthiophene to obtain title compound (4.5 mg).

(LCMS m/z 511.2 (MH+), retention time 1.58 minutes, LC conditions LC-1)

Example 12: 5-(2-(4-(4-(3-((5-Cyanothiophen-3-yl)ethynyl)phenyl)-3-hydroxybutyl)-2-oxo-1,3,4-thiadiazinan-3-yl)ethyl)thiophene-2-carboxylic Acid

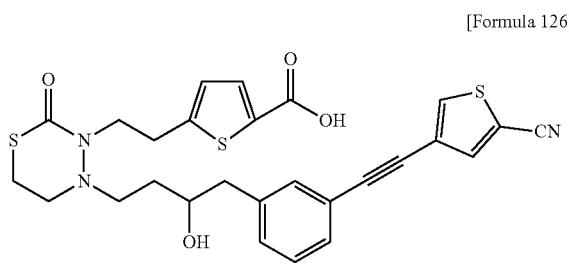 [SMILES: N#Cc1cc(C#Cc2cccc(CC(O)CCN3CCSC(=O)N3CCc3ccc(C(=O)O)s3)c2)cs1]

[Formula 126]

[Step a]

Methyl 5-(2-(4-(3-((tert-Butyldimethylsilyl)oxy)-4-(3-((5-cyanothiophen-3-yl)ethynyl)phenyl)butyl)-2-oxo-1,3,4-thiadiazinan-3-yl)ethyl)thiophene-2-carboxylate (Intermediate Z-7-12)

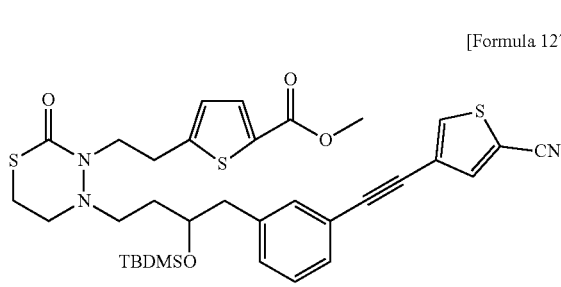

[Formula 127]

To a solution of the intermediate Z-22 (14 mg) in acetonitrile (400 μL), bis(acetonitrile)palladium chloride (0.7 mg), 2-dicyclohexylphosphino-2',4',6'-triisopropylbiphenyl (3.6 mg), cesium carbonate (12.3 mg), and 4-bromothiophene-2-carbonitrile (18.9 mg, COMBI-BLOCKS) were successively added, and the resulting mixture was stirred at 60° C. for 6 hours under a nitrogen gas atmosphere. The solvent was evaporated under reduced pressure, and then the resulting residue was purified by column chromatography (hexane/ethyl acetate) to obtain the title compound (6.4 mg).

(Intermediate Z-7-12: LCMS m/z 680.4 (MH+), retention time 1.71 minutes, LC conditions LC-6)

[Step b]

5-(2-(4-(4-(3-((5-Cyanothiophen-3-yl)ethynyl)phenyl)-3-hydroxybutyl)-2-oxo-1,3,4-thiadiazinan-3-yl)ethyl)thiophene-2-carboxylic Acid A solution of the intermediate Z-7-12 (6.4 mg) in tetrahydrofuran (330 μL) was cooled to 0° C., tetrabutylammonium fluoride (1 mol/L solution in tetrahydrofuran, 28 μL) was added to the solution, and the resulting mixture was stirred at room temperature for 4 hours. To the reaction mixture, 1 mol/L aqueous sodium hydroxide (30 μL) was added, and the mixture was stirred at room temperature for 2 hours. To the reaction mixture, 1 mol/L hydrochloric acid was added, the mixture was extracted with ethyl acetate, and then the organic layer was dried. The solvent was evaporated under reduced pressure, and the resulting residue was purified by column chromatography (chloroform/methanol) to obtain the title compound (0.7 mg).

(LCMS m/z 552.2 (MH+), retention time 1.60 minutes, LC conditions LC-1)

Example 13: 5-(2-(4-(3-Hydroxy-4-(3-(thiazol-2-ylethynyl)phenyl)butyl)-2-oxo-1,3,4-thiadiazinan-3-yl)ethyl)thiophene-2-carboxylic Acid

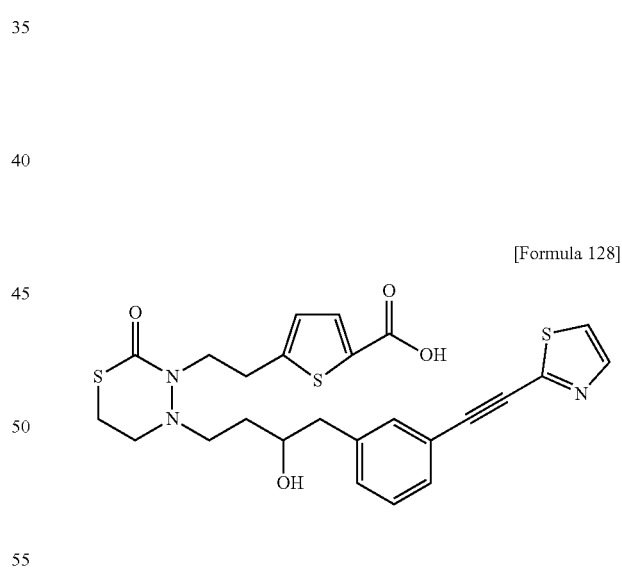

[Formula 128]

Synthesis was performed according to the method described in Example 6 by using 2-bromothiazole (16.5 mg, TCI) instead of 4-bromothiophene-2-carbonitrile to obtain the title compound (0.4 mg).

(LCMS m/z 528.2 (MH+), retention time L43 minutes, LC conditions LC-1)

Example 14: 5-(2-(4-(4-(3-((3-Cyanothiophen-2-yl)ethynyl)phenyl)-3-hydroxybutyl)-2-oxo-1,3,4-thiadiazinan-3-yl)ethyl)thiophene-2-carboxylic Acid

[Formula 129]

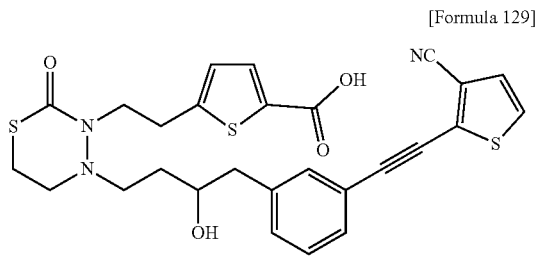 [SMILES: N#Cc1ccsc1C#Cc1cccc(CC(O)CCN2CCSC(=O)N2CCc2ccc(C(=O)O)s2)c1]

[Step a]

Methyl 5-(2-(4-(3-((tert-Butyldimethylsilyl)oxy)-4-(3-((3-cyanothiophen-2-yl)ethynyl)phenyl)butyl)-2-oxo-1,3,4-thiadiazinan-3-yl)ethyl)thiophene-2-carboxylate (Intermediate Z-7-14)

[Formula 130]

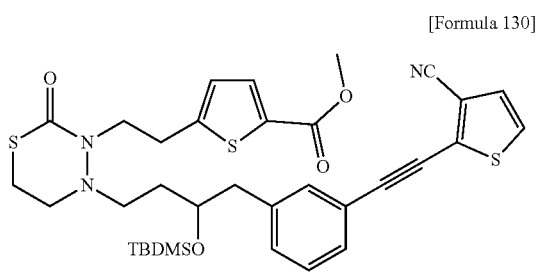 [SMILES: COC(=O)c1ccc(CCN2C(=O)SCCN2CCC(Cc2cccc(C#Cc3sccc3C#N)c2)O[Si](C)(C)C(C)(C)C)s1]

To a solution of the intermediate Z-22 (16 mg) in acetonitrile (1 mL), bis(acetonitrile)palladium chloride (0.7 mg), 2-dicyclohexylphosphino-2',4',6'-triisopropylbiphenyl (4.0 mg), cesium carbonate (10.9 mg), and 2-bromothiophene-3-carbonitrile (15.7 mg, MAYBRIDGE) were successively added, and the resulting mixture was stirred at 60° C. for 18 hours under a nitrogen gas atmosphere. The reaction mixture was filtered through filter paper covered with Celite, the residue remained on Celite was washed with a mixed solvent of chloroform and methanol (9:1). The filtrate and the wash liquid were mixed, the solvent was evaporated under reduced pressure, and then the resulting residue was purified by column chromatography (hexane/ethyl acetate) to obtain the title compound (7.9 mg).

(Intermediate Z-7-14: LCMS m/z 680.5 (MH$^+$), retention time 2.52 minutes, LC conditions LC-1)

[Step b]

5-(2-(4-(4-(3-((3-Cyanothiophen-2-yl)ethynyl)phenyl)-3-hydroxybutyl)-2-oxo-1,3,4-thiadiazinan-3-yl)ethyl)thiophene-2-carboxylic Acid A solution of the intermediate Z-7-14 (7.9 mg) in tetrahydrofuran (1 mL) was cooled to 0° C., tetrabutylammonium fluoride (1 mol/L solution in tetrahydrofuran, 0.5 mL) was added to the solution, and the resulting mixture was stirred at room temperature for 18 hours. To the reaction mixture, methanol (0.5 mL), and 1 mol/L aqueous sodium hydroxide (0.5 mL) were added, and the resulting mixture was stirred at room temperature for 2.5 hours. To the reaction mixture, 1 mol/L hydrochloric acid was added, the mixture was extracted with ethyl acetate, and the organic layer was dried. The solvent was evaporated under reduced pressure, and the resulting residue was purified by column chromatography (chloroform/methanol) to obtain the title compound (3.0 mg).

(LCMS m/z 552.0 (MH$^+$), retention time 1.57 minutes, LC conditions LC-1)

Example 15: 5-(2-(4-(3-Hydroxy-4-(3-(phenylethynyl)phenyl)butyl)-2-oxo-1,3,4-thiadiazinan-3-yl)ethyl)thiophene-2-carboxylic Acid

[Formula 131]

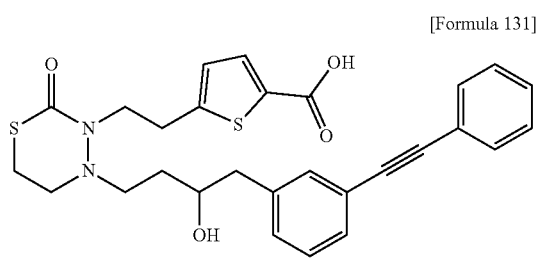 [SMILES: O=C(O)c1ccc(CCN2C(=O)SCCN2CCC(O)Cc2cccc(C#Cc3ccccc3)c2)s1]

Synthesis was performed according to the method described in Example 14 by using bromobenzene (12.3 mg, TCI) instead of 2-bromothiophene-2-carbonitrile to obtain the title compound (2.4 mg).

(LCMS m/z 521.0 (MH$^+$), retention time 1.71 minutes, LC conditions LC-1)

Example 16: 5-(2-(4-(3-Hydroxy-4-(3-((2-methoxyphenyl)ethynyl)phenyl)butyl)-2-oxo-1,3,4-thiadiazinan-3-yl)ethyl)thiophene-2-carboxylic Acid

[Formula 132]

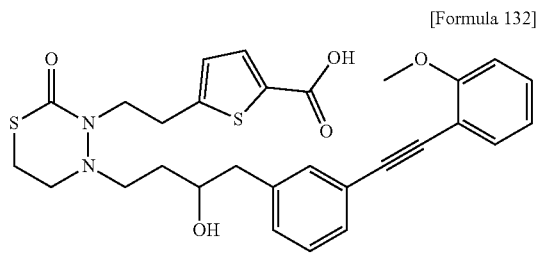 [SMILES: COc1ccccc1C#Cc1cccc(CC(O)CCN2CCSC(=O)N2CCc2ccc(C(=O)O)s2)c1]

Synthesis was performed according to the method described in Example 14 by using 1-bromo-2-methoxybenzene (14.7 mg, WAKO) instead of 2-bromothiophene-2-carbonitrile to obtain the title compound (1.6 mg).

(LCMS m/z 551.3 (MH$^+$), retention time 1.64 minutes, LC conditions LC-1)

Reference Example A-10-2: (3-Chlorothiophen-2-yl)methanol (Intermediate A-10-2)

[Formula 133]

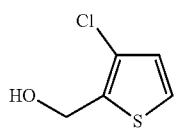

A solution of 3-chlorothiophene-2-carboxylic acid (4.47 g, ALDRICH) in tetrahydrofuran (88.1 mL) was cooled to 0° C. under a nitrogen gas atmosphere, a 1 mol/L solution of borane-tetrahydrofuran complex in tetrahydrofuran (49.7 mL) was added dropwise to the solution, and the resulting mixture was stirred at room temperature for 22 hours. The reaction mixture was cooled to 0° C., methanol, water, and ethyl acetate were added to the mixture, and the resulting mixture was stirred. The organic solvent was evaporated under reduced pressure, then ethyl acetate was added to the residue, and the organic layer was successively washed with saturated aqueous sodium hydrogencarbonate, and saturated brine, and dried. The solvent was evaporated under reduced pressure to obtain the title compound (4.62 g).

(Intermediate A-10-2: Rf (TLC)=0.40 (hexane ethyl acetate=2:1))

Reference Example A-11-2: 3-Chloro-2-(bromomethyl)thiophene (Intermediate A-11-2)

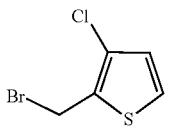

[Formula 134]

A solution of the intermediate A-10-2 (4.62 g) in dichloromethane (110 mL) was cooled to 0° C., triphenylphosphine (10.8 g), and carbon tetrabromide (10.9 g) were added to the solution, and the resulting mixture was stirred at room temperature for 1 hour. To the reaction mixture, water, saturated brine, and ethyl acetate were added, the mixture was stirred, and then the organic solvent was evaporated under reduced pressure. Ethyl acetate was added to the residue, and the organic layer was successively washed with saturated brine, and dried. The organic solvent was evaporated under reduced pressure, and then a mixed solvent of hexane and ethyl acetate (9:1) was added to the resulting residue to prepare a suspension, and the suspension was filtered through filter paper covered with silica gel. The solvent of the filtrate was evaporated under reduced pressure to obtain the title compound (9.09 g).

(Intermediate A-11-2: Rf (TLC)=0.56 (hexane:ethyl acetate=8:1))

Reference Example A-12-2: 2-(3-Chlorothiophen-2-yl)acetonitrile (Intermediate A-12-2)

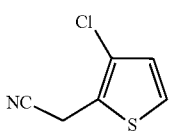

[Formula 135]

To the intermediate A-11-2 (9.09 g), dimethyl sulfoxide (42 mL), and acetonitrile (126 mL) were added, the mixture was cooled to 0° C., then sodium cyanide (2.46 g) was added to the mixture, and the resulting mixture was stirred at room temperature for 2 hours. To the reaction mixture, water, saturated brine, and ethyl acetate were added, the resulting mixture was stirred, and then the organic layer was washed with saturated brine, and dried. The solvent was evaporated under reduced pressure, and then the resulting residue was purified by column chromatography (hexane/ethyl acetate) to obtain the title compound (3.41 g).

(Intermediate A-12-2: Rf (TLC)=0.20 (hexane:ethyl acetate=8:1))

Reference Example A-13-2: Ethyl 2-(3-chlorothiophen-2-yl)acetate (Intermediate A-13-2)

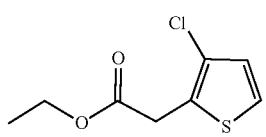

[Formula 136]

To a solution of the intermediate A-12-2 (3.41 g) in ethanol (36 mL), water (0.46 mL) was added, the mixture was cooled to 0° C., and then concentrated sulfuric acid (6.3 mL) was added portionwise to the mixture. The reaction mixture was stirred at 85° C. for 88 hours, and then cooled to 0° C., and saturated aqueous sodium hydrogencarbonate was added to the mixture until the mixture became neutral. Ethyl acetate was added to the mixture, and the resulting mixture was stirred, and then concentrated under reduced pressure. Ethyl acetate was added to the mixture, and the organic layer was successively washed with saturated aqueous sodium hydrogencarbonate, and saturated brine, and dried. The solvent was evaporated under reduced pressure to obtain the title compound (4.56 g).

(Intermediate A-13-2: Rf (TLC)=0.31 (hexane:ethyl acetate=8:1))

Reference Example A-14-2: 2-(3-Chlorothiophen-2-yl)ethanol (Intermediate A-14-2)

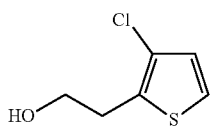

[Formula 137]

A solution of the intermediate A-13-2 (4.56 g) in tetrahydrofuran (108 mL) was cooled to 0° C. under a nitrogen gas atmosphere, lithium aluminum hydride (1.48 g) was added to the solution, and the mixture was stirred for 0.7 hour. To the reaction mixture, water, diethyl ether, and 1 mol/L hydrochloric acid were added, the resulting mixture was stirred, and then the organic layer was successively washed with 1 mol/L hydrochloric acid, saturated aqueous sodium hydrogencarbonate, and saturated brine, and dried. The solvent was evaporated under reduced pressure to obtain the title compound (3.67 g).

(Intermediate A-14-2: Rf (TLC)=0.13 (hexane:ethyl acetate=4:1))

Reference Example A-2-3: (2-(3-Chlorothiophen-2-yl)ethoxy)(tert-butyl)dimethylsilane (Intermediate A-2-3)

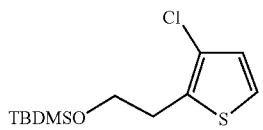

[Formula 138]

The intermediate A-2-3 was synthesized according to the method described in Reference Example A-2 by using the intermediate A-14-2 (3.67 g) instead of 2-(thiophen-2-yl)ethanol, and thus the title compound (4.29 g) was obtained.

(Intermediate A-2-3: Rf (TLC)=0.61 (hexane:ethyl acetate=4:1))

Reference Example A-3-3: 4-Chloro-5-(2-((tert-butyldimethylsilyl)oxy)ethyl)thiophene-2-carboxylic Acid (Intermediate A-3-3)

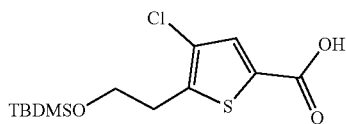

[Formula 139]

The intermediate A-3-3 was synthesized according to the method described in Reference Example A-3 by using the intermediate A-2-3 (3.03 g) instead of the intermediate A-2, and thus the title compound (3.41 g) was obtained.

(Intermediate A-3-3: Rf (TLC)=0.11 (hexane:ethyl acetate=4:1))

Reference Example A-4-3: Methyl 4-chloro-5-(2-hydroxyethyl)thiophene-2-carboxylate (Intermediate A-4-3)

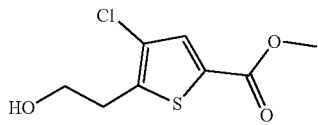

[Formula 140]

The intermediate A-4-3 was synthesized according to the method described in Reference Example A-4 by using the intermediate A-3-3 (4.35 g) instead of the intermediate A-3, and thus the title compound (2.23 g) was obtained.

(Intermediate A-4-3: Rf (TLC)=0.38 (hexane:ethyl acetate=1:1))

Reference Example A-5-3: Methyl 4-chloro-5-(2-bromoethyl)thiophene-2-carboxylate (Intermediate A-5-3)

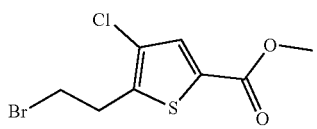

[Formula 141]

The intermediate A-5-3 was synthesized according to the method described in Reference Example A-5 by using the intermediate A-4-3 (2.23 g) instead of the intermediate A-4, and thus the title compound (3.18 g) was obtained.

(Intermediate A-5-3: Rf (TLC)=0.52 (hexane:ethyl acetate=2:1))

Reference Example A-6-3: tert-Butyl 2-(2-(3-chloro-5-(methoxycarbonyl)thiophen-2-yl)ethyl)hydrazinecarboxylate (Intermediate A-6-3)

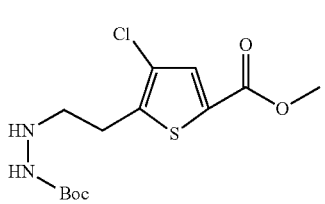

[Formula 142]

The intermediate A-6-3 was synthesized according to the method described in Reference Example A-6 by using the intermediate A-5-3 (3.18 g) instead of the intermediate A-5, and thus the title compound (3.29 g) was obtained.

(Intermediate A-5-3: Rf (TLC)=0.24 (hexane:ethyl acetate=2:1))

Reference Example Z-1-3: tert-Butyl 2 (2-(3-chloro-5-(methoxycarbonyl)thiophen-2-yl)ethyl)-2-(((2-chloroethyl)thio)carbonyl)hydrazinecarboxylate (Intermediate Z-1-3)

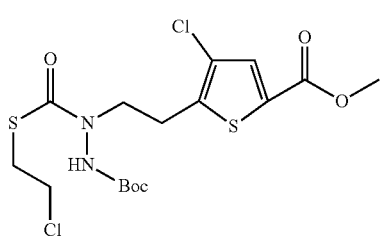

[Formula 143]

The intermediate Z-1-3 was synthesized according to the method described in Reference Example Z-1-2 by using the intermediate A-6-3 (1.79 g) instead of the intermediate A-6-2, and thus the title compound (2.36 g) was obtained.

(Intermediate Z-1-3: Rf (TLC)=0.24 (hexane:ethyl acetate=4:1))

Reference Example Z-2-3: Methyl 4-chloro-5-(2-(1-(((2-chloroethyl)thio)carbonyl)hydrazinyl)ethyl)thiophene-2-carboxylate (Intermediate Z-2-3)

[Formula 144]

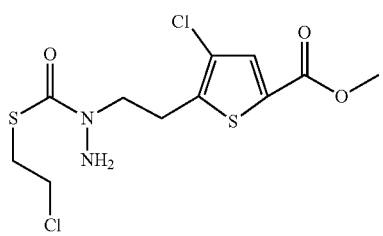

The intermediate Z-2-3 was synthesized according to the method described in Reference Example Z-2-2 by using the intermediate Z-1-3 (2.36 g) instead of the intermediate Z-1-2, and thus the title compound (1.73 g) was obtained.
(Intermediate Z-2-3: Rf (TLC)=0.69 (hexane:ethyl acetate=1:1))

Reference Example Z-3-3: Methyl 4-chloro-5-(2-(2-oxo-1,3,4-thiadiazinan-3-yl)ethyl)thiophene-2-carboxylate (Intermediate Z-3-3)

[Formula 145]

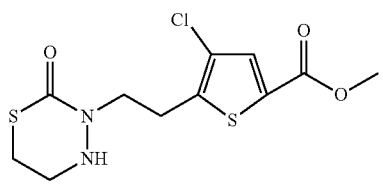

The intermediate Z-3-3 was synthesized according to the method described in Reference Example Z-3-2 by using of the intermediate Z-2-3 (1.73 g) instead of the intermediate Z-2-2, and thus the title compound (1.04 g).
(Intermediate Z-3-3: Rf (TLC)=0.23 (hexane:ethyl acetate=1:1))

Reference Example Z-4-3: Methyl 4-chloro-5-(2-(4-(4-(3-iodophenyl)-3-oxobutyl)-2-oxo-1,3,4-thiadiazinan-3-yl)ethyl)thiophene-2-carboxylate (Intermediate Z-4-3)

[Formula 146]

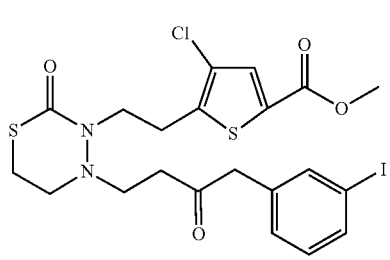

The intermediate Z-4-3 was synthesized according to the method described in Reference Example Z-4 by using the intermediate Z-3-3 (0.30 g) instead of the intermediate Z-3, and the intermediate C-3-2 (the whole amount of the intermediate C-3-2 produced and obtained according to the method described in Reference Example C-3-2 using 2.56 g of the starting material, intermediate C-2-2) instead of the intermediate C-3, and thus the title compound (0.64 g) was obtained.
(Intermediate Z-4-3: Rf (TLC)=0.31 (hexane:ethyl acetate=1:1))

Reference Example Z-14-4: Methyl 4-chloro-5-(2-(2-oxo-4-(3-oxo-4-(3-(thiophen-3-ylethynyl)phenyl)butyl)-1,3,4-thiadiazinan-3-yl)ethyl)thiophene-2-carboxylate (Intermediate Z-14-4)

[Formula 147]

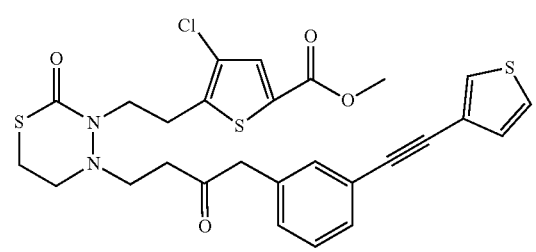

To the intermediate Z-4-3 (429 mg), diethylamine (3.62 mL), 3-ethynylthiophene (93 μL), copper(I) iodide (13.8 mg), and tetrakis(triphenyl-phosphine)palladium (41.8 mg) were successively added, and the mixture was stirred at room temperature for 3.5 hours under a nitrogen gas atmosphere. To the reaction mixture, 1 mol/L hydrochloric acid was added, and the mixture was extracted twice with ethyl acetate. The organic layer was successively washed with saturated brine, saturated aqueous sodium hydrogencarbonate, and saturated brine, and dried. The solvent was evaporated under reduced pressure, and the resulting residue was purified by column chromatography (chloroform/methanol) to obtain the title compound (290.4 mg).
(Intermediate Z-14-4: LCMS m/z 573.2 (MH$^+$), retention time 2.03 minutes, LC conditions LC-1)

Reference Example Z-17-17: Methyl 4-chloro-5-(2-(4-(3-hydroxy-4-(3-(thiophen-3-ylethynyl)phenyl)butyl)-2-oxo-1,3,4-thiadiazinan-3-yl)ethyl)thiophene-2-carboxylate (Intermediate Z-17-17)

[Formula 148]

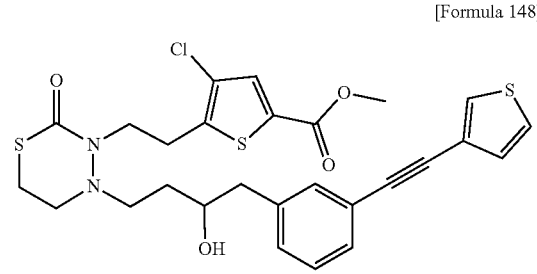

To a solution of the intermediate Z-14-4 (290 mg) in methanol (5 mL), tetrahydrofuran (1 mL) was added, the mixture was cooled to 0° C., and sodium borohydride (28.8 mg) was added portionwise to the mixture. The mixture was stirred at room temperature for 1.6 hours, then water was added to the mixture, and 1 N hydrochloric acid was further added portionwise to the reaction mixture until the mixture became weakly acidic. The mixture was extracted twice with ethyl acetate, and then the organic layer was successively washed with saturated aqueous sodium hydrogencarbonate, and saturated brine, and dried. The solvent was evaporated under reduced pressure, and the resulting residue was purified by column chromatography (chloroform/methanol) to obtain the title compound (183 mg).

(Intermediate Z-17-17: LCMS m/z 575.2 (MH$^+$), retention time 1.98 minutes, LC conditions LC-1)

Example 17: 4-Chloro-5-(2-(4-(3-hydroxy-4-(3-(thiophen-3-ylethynyl)phenyl)butyl)-2-oxo-1,3,4-thiadiazinan-3-yl)ethyl)thiophene-2-carboxylic Acid

[Formula 149]

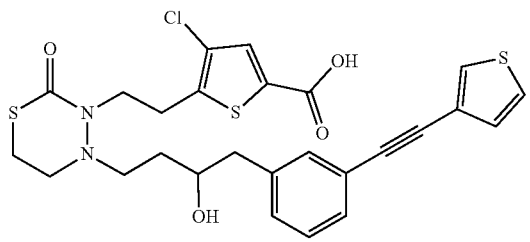

To a solution of the intermediate Z-17-17 (183 mg) in tetrahydrofuran (2 mL), methanol (2 mL) was added to the solution, the mixture was cooled to 0° C., and water (2.38 mL), and 4 mol/L aqueous lithium hydroxide (2.38 mL) were added to the mixture. The resulting mixture was stirred at room temperature for 1 hour, then water was added to the reaction mixture, and further 2 N hydrochloric acid was added portionwise to the reaction mixture until the mixture became weakly acidic. The reaction mixture was extracted twice with ethyl acetate, and then the organic layer was successively washed with saturated aqueous sodium hydrogencarbonate, and saturated brine, and dried. The solvent was evaporated under reduced pressure, and the resulting residue was purified by column chromatography (chloroform/methanol) to obtain the title compound (129 mg).

(LCMS m/z 561.25 (MH$^+$), retention time 1.72 minutes, LC conditions LC-1)

Reference Example C-1: 2-(3-Bromo-4-methylphenyl)acetonitrile (Intermediate C-1)

[Formula 150]

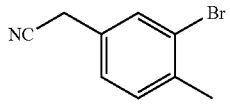

To a solution of 2-bromo-1,4-dimethylbenzene (2 g, TCI) in carbon tetrachloride (21.6 mL), N-bromosuccinimide (1.06 g), and benzoyl peroxide (56.7 mg) were added, and the mixture was stirred at 85° C. for 1.5 hours. To the reaction mixture, N-bromosuccinimide (1.06 g), and benzoyl peroxide (56.7 mg) were added, and the resulting mixture was further stirred at 85° C. for 4.5 hours. The reaction mixture was cooled to room temperature, and then filtered through filter paper, and the residue remained on the filter paper was washed with dichloromethane. The filtrate and the wash liquid were mixed, and the solvent was evaporated under reduced pressure. To the resulting residue, ethanol (10.8 mL), water (5.4 mL), and potassium cyanide (2.1 g) were added, and the mixture was stirred at 100° C. for 5 hours. The reaction mixture was cooled to room temperature, and extracted with ethyl acetate, and then the organic layer was dried. The solvent was evaporated under reduced pressure, and the resulting residue was purified by column chromatography (hexane/ethyl acetate) to obtain the title compound (576 mg).

(Intermediate C-1: Rf (TLC)=0.58 (hexane:ethyl acetate=2:1))

$^1$H-NMR (CDCl$_3$): δ (ppm) 7.51 (1H, s), 7.24 (1H, d, J=7.5 Hz), 7.18 (1H, d, J=7.5 Hz), 3.70 (2H, s), 2.40 (3H, s)

Reference Example C-2-4: 2-(3-Bromo-4-methylphenyl)-N-methoxy-N-methylacetamide (Intermediate C-2-4)

[Formula 151]

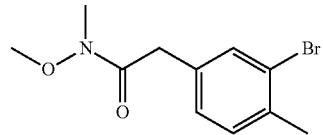

To the intermediate C-1 (300 mg), water (7.1 mL) was added, the mixture was cooled to 0° C., concentrated sulfuric acid (5.7 mL) was added portionwise to the mixture, and then the resulting mixture was stirred at 105° C. for 15 hours. The reaction mixture was cooled to room temperature, and then ethyl acetate was added for extraction. Hexane was added to the aqueous layer for extraction, and then the aqueous layer was further extracted with diethyl ether. The resulting organic layers were mixed, and washed with saturated aqueous sodium hydrogencarbonate, and dried. The solvent was evaporated under reduced pressure, and to the resulting residue. N,N-dimethylformamide (14.3 mL), N,O-dimethylhydroxylamine hydrochloride (557 mg), 1-ethyl-3-(3-dimethylaminopropyl)carbodiimide hydrochloride (821 mg), N,N-dimethyl-4-aminopyridine (17 mg), and diisopropylethylamine (L2 mL) were successively added, and the resulting mixture was stirred at room temperature for 17 hours. To the reaction mixture, diethyl ether was added, and then the organic layer was washed 3 times with 1 mol/L hydrochloric acid, and once with saturated brine, and dried. The solvent was evaporated under reduced pressure, and the resulting residue was purified by column chromatography (hexane/ethyl acetate) to obtain the title compound (221 mg).

(Intermediate C-2-4: LCMS m/z 272.3 (MH$^+$), retention time 1.57 minutes, LC conditions LC-1)

Reference Example Z-4-4: Methyl 5-(2-(4-(4-(3-bromo-4-methylphenyl)-3-oxobutyl)-2-oxo-1,3,4-thiadiazinan-3-yl)ethyl)thiophene-2-carboxylate (Intermediate Z-4-4)

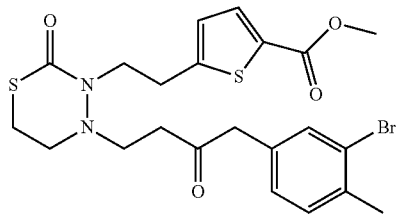

[Formula 152]

A solution of the intermediate C-2-4 (142.6 mg) in dimethoxyethane (2.85 mL) was cooled to 0° C. under a nitrogen atmosphere. To the reaction mixture, vinylmagnesium bromide (1 mol/L solution in tetrahydrofuran, 790 μL, ALDRICH) was added, and the mixture was stirred for 4 hours. To the reaction mixture, 2 mol/L hydrochloric acid was added, and the mixture was stirred for 1 minute. Ethyl acetate was added to the mixture for extraction, and the organic layer was dried. The solvent was evaporated under reduced pressure, ethanol (3 mL), water (3 mL), and the intermediate Z-3 (100 mg) were added to the resulting residue, and the mixture was stirred overnight at 110° C. To the reaction mixture, saturated brine was added, and the mixture was extracted with chloroform. The organic layer was dried, and the solvent was evaporated under reduced pressure. The resulting residue was purified by column chromatography (hexane/ethyl acetate) to obtain the title compound (151.9 mg).

(Intermediate Z-4-4: LCMS m/z 525.1 (MH$^+$), retention time 1.87 minutes, LC conditions LC-1)

Reference Example Z-6-4: Methyl 5-(2-(4-(4-(3-bromo-4-methylphenyl)-3-((tert-butyldimethylsilyl)oxy)butyl)-2-oxo-1,3,4-thiadiazinan-3-yl)ethyl)thiophene-2-carboxylate (Intermediate Z-6-4)

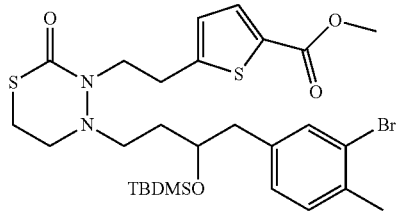

[Formula 153]

To a solution of the intermediate Z-4-4 (152 mg) in methanol (2.9 mL), tetrahydrofuran (5 mL) was added, the mixture was cooled to 0° C., and sodium borohydride (16.4 mg) was added to the mixture. The mixture was stirred at 0° C. for 1 hour, and then diluted hydrochloric acid was added portionwise to the reaction mixture until the mixture became weakly acidic. The organic solvent was evaporated under reduced pressure, then ethyl acetate was added to the residue for extraction, the organic layer was dried, and then the solvent was evaporated under reduced pressure. To the resulting residue, N,N-dimethylformamide (1.4 mL), imidazole (98 mg), and tert-butyldimethylchlorosilane (131 mg) were successively added, and the resulting mixture was stirred overnight at room temperature. To the reaction mixture, 2 mol/L hydrochloric acid was added, and the mixture was extracted with ethyl acetate. The organic layer was successively washed with water, and saturated brine, and then dried. The solvent was evaporated under reduced pressure, and the resulting residue was purified by column chromatography (hexane/ethyl acetate) to obtain the title compound (165.7 mg).

(Intermediate Z-6-4: LCMS m/z 641.2 (MH$^+$), retention time 2.02 minutes, LC conditions LC-6)

Reference Example Z-7-18: Methyl 5-(2-(4-(3-((tert-butyldimethylsilyl)oxy)-4-(4-methyl-3-(thiophen-3-ylethynyl)phenyl)butyl)-2-oxo-1,3,4-thiadiazinan-3-yl)ethyl)thiophene-2-carboxylate (Intermediate Z-7-18)

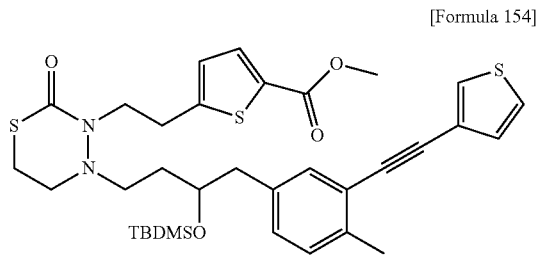 [SMILES: COC(=O)c1ccc(CCN2C(=O)SCCN2CCC(Cc2ccc(C)c(C#Cc3ccsc3)c2)O[Si](C)(C)C(C)(C)C)s1]

[Formula 154]

The intermediate Z-7-18 was synthesized according to the method described in Reference Example C-4 by using the intermediate Z-6-4 (20.0 mg) instead of the intermediate C-2-2, and thus the title compound (23.4 mg) was obtained.

(Intermediate Z-7-18: LCMS m/z 669.3 (MH$^+$), retention time 2.25 minutes, LC conditions LC-6)

Example 18: 5-(2-(4-(3-Hydroxy-4-(4-methyl-3-(thiophen-3-ylethynyl)phenyl)butyl)-2-oxo-1,3,4-thiadiazinan-3-yl)ethyl)thiophene-2-carboxylic Acid

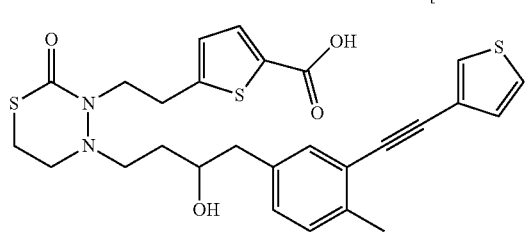

[Formula 155]

A solution of the intermediate Z-7-18 (23.4 mg) in tetrahydrofuran (0.93 mL) was cooled to 0° C., tetrabutylammonium fluoride (1 mol/L solution in tetrahydrofuran, 93 μL) was added to the solution, and the mixture was stirred at room temperature for 1.5 hours. To the reaction mixture, tetrabutylammonium fluoride (1 mol/L solution in tetrahydrofuran, 93 μL) was added, and the mixture was stirred at room temperature for further 1.5 hours. To the reaction mixture, methanol (0.93 mL), and 1 mol/L aqueous sodium hydroxide (0.93 mL) were added, and the mixture was stirred overnight at room temperature. To the reaction mixture, 1 mol/L hydrochloric acid was added, the mixture was extracted with ethyl acetate, and the organic layer was dried. The solvent was evaporated under reduced pressure, and the resulting residue was purified by column chromatography (chloroform/methanol) to obtain the title compound (17.3 mg).

(LCMS m/z 541.2 (MH+), retention time 1.74 minutes, LC conditions LC-1)

Reference Example C-1-2: 2-(3-Bromo-5-methylphenyl)acetonitrile (Intermediate C-1-2)

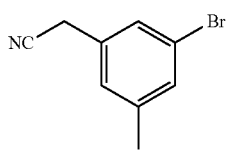

[Formula 156]

The intermediate C-1-2 was synthesized according to the method described in Reference Example C-1 by using 1-bromo-3,5-dimethylbenzene (4.00 g, TCI) instead of 2-bromo-1,4-dimethylbenzene, and thus the title compound (2.34 g) was obtained.

(Intermediate C-1-2: Rf (TLC)=0.64 (hexane:ethyl acetate=2:1))

$^1$H-NMR (CDCl$_3$): δ (ppm) 7.31 (1H, m), 7.28 (1H, m), 7.09 (1H, m), 3.69 (2H, s), 2.35 (3H, s)

Reference Example C-2-5: 2-(3-Bromo-5-methylphenyl)-N-methoxy-N-methylacetamide (Intermediate C-2-5)

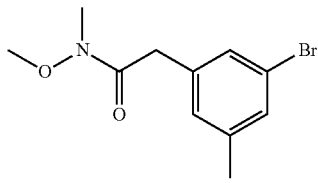

[Formula 157]

The intermediate C-2-5 was synthesized according to the method described in Reference Example C-2-4 by using the intermediate C-1-2 (500 mg) instead of the intermediate C-1, and thus the title compound (553 mg) was obtained.

(Intermediate C-2-5: LCMS m/z 272.3 (MH+), retention time 1.57 minutes, LC conditions LC-1)

Reference Example Z-4-5: Methyl 5-(2-(4-(4-(3-bromo-5-methylphenyl)-3-oxobutyl)-2-oxo-1,3,4-thiadiazinan-3-yl)ethyl)thiophene-2-carboxylate (Intermediate Z-4-5)

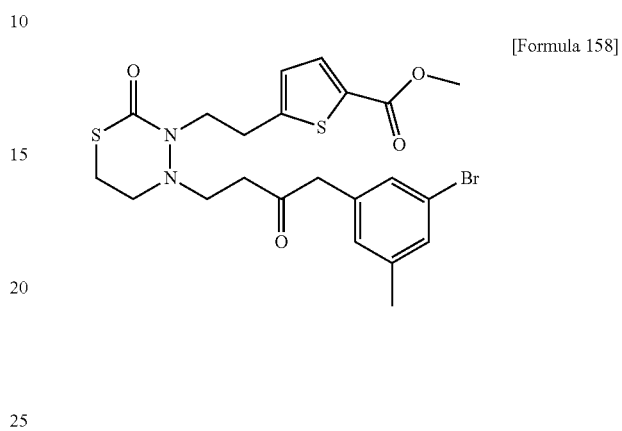

[Formula 158]

The intermediate Z-4-5 was synthesized according to the method described in Reference Example Z-4-4 by using the intermediate C-2-5 (142.6 mg) instead of the intermediate C-2-4, and thus the title compound (149.9 mg) was obtained.

(Intermediate Z-4-5: LCMS m/z 525.1 (MH+), retention time 1.88 minutes, LC conditions LC-1)

Reference Example Z-6-5: Methyl 5-(2-(4-(4-(3-bromo-5-methylphenyl)-3-((tert-butyldimethylsilyl)oxy)butyl)-2-oxo-1,3,4-thiadiazinan-3-yl)ethyl)thiophene-2-carboxylate (Intermediate Z-6-5)

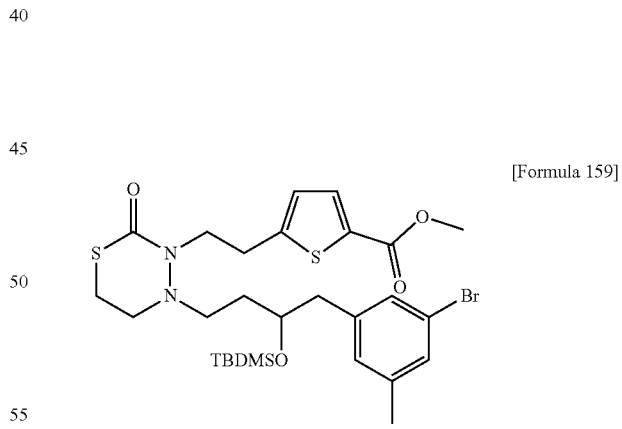

[Formula 159]

The intermediate Z-6-5 was synthesized according to the method described in Reference Example Z-6-4 by using the intermediate Z-4-5 (149.9 mg) instead of the intermediate Z-4-4, and thus the title compound (163.0 mg) was obtained.

(Intermediate Z-6-5: LCMS m/z 641.3 (MH+), retention time 2.00 minutes, LC conditions LC-6)

Reference Example Z-7-19: Methyl 5-(2-(4-(3-((tert-butyldimethylsilyl)oxy)-4-(3-methyl-5-(thiophen-3-ylethynyl)phenyl)butyl)-2-oxo-1,3,4-thiadiazinan-3-yl)ethyl)thiophene-2-carboxylate (Intermediate Z-7-19)

[Formula 160]

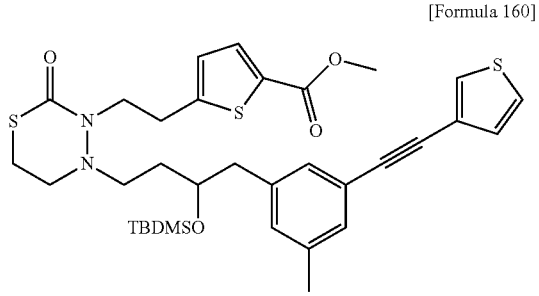 [SMILES: COC(=O)c1ccc(CCN2C(=O)SCCN2CCC(Cc2cc(C)cc(C#Cc3ccsc3)c2)O[Si](C)(C)C(C)(C)C)s1]

The intermediate Z-7-19 was synthesized according to the method described in Reference Example C-4 by using the intermediate Z-6-5 (20 mg) instead of the intermediate C-2-2, and thus the title compound (19.2 mg) was obtained.
(Intermediate Z-7-19: LCMS m/z 669.3 (MH$^+$), retention time 2.25 minutes, LC conditions LC-6)

Example 19: 5-(2-(4-(3-Hydroxy-4-(3-methyl-5-(thiophen-3-ylethynyl)phenyl)butyl)-2-oxo-1,3,4-thiadiazinan-3-yl)ethyl)thiophene-2-carboxylic Acid

[Formula 161]

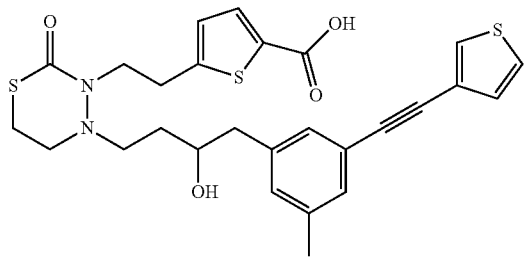

Synthesis was performed according to the method described in Example 18 by using the intermediate Z-7-19 (19.2 mg) instead of the intermediate Z-7-18 to obtain the title compound (13.5 mg).
(LCMS m/z 541.2 (MH$^+$), retention time 1.74 minutes, LC conditions LC-1)

Reference Example C-2-6: 2-(3-Bromo-4-fluorophenyl)-N-methoxy-N-methylacetamide (Intermediate C-2-6)

[Formula 162]

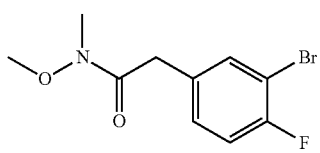

To a solution of 2-(3-bromo-4-fluorophenyl)acetic acid (500 mg) in dichloromethane (43 mL), N,O-dimethylhydroxylamine hydrochloride (419 mg), 1-ethyl-3-(3-dimethylaminopropyl)carbodiimide hydrochloride (494 mg), N,N-dimethyl-4-aminopyridine (26 mg), and diisopropylethylamine (1.2 mL) were successively added, and the resulting mixture was stirred overnight at room temperature. The solvent of the reaction mixture was evaporated under reduced pressure, ethyl acetate was added to the residue, and then the organic layer was successively washed with 1 mol/L hydrochloric acid, and saturated brine, and dried. The solvent was evaporated under reduced pressure, and the resulting residue was purified by column chromatography (hexane/ethyl acetate) to obtain the title compound (449 mg).
(Intermediate C-2-6: LCMS m/z 276.2 (MH$^+$), retention time 1.37 minutes, LC conditions LC-1)

Reference Example Z-4-6: Methyl 5-(2-(4-(4-(3-bromo-4-fluorophenyl)-3-oxobutyl)-2-oxo-1,3,4-thiadiazinan-3-yl)ethyl)thiophene-2-carboxylate (Intermediate Z-4-6)

[Formula 163]

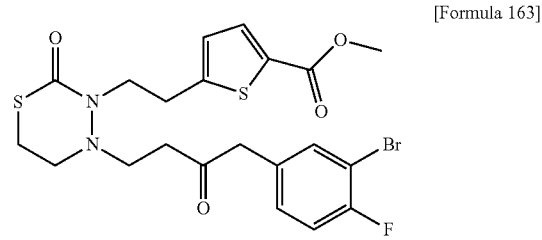 [SMILES: COC(=O)c1ccc(CCN2C(=O)SCCN2CCC(=O)Cc2ccc(F)c(Br)c2)s1]

The intermediate Z-4-6 was synthesized according to the method described in Reference Example Z-4-4 by using the intermediate C-2-6 (450.5 mg) instead of the intermediate C-2-4, and thus the title compound (562.8 mg) was obtained.
(Intermediate Z-4-6: LCMS m/z 529.1 (MH$^+$), retention time 1.78 minutes, LC conditions LC-1)

Reference Example Z-6-6: Methyl 5-(2-(4-(4-(3-bromo-4-fluorophenyl)-3-((tert-butyldimethylsilyl)oxy)butyl)-2-oxo-1,3,4-thiadiazinan-3-yl)ethyl)thiophene-2-carboxylate (Intermediate Z-6-6)

[Formula 164]

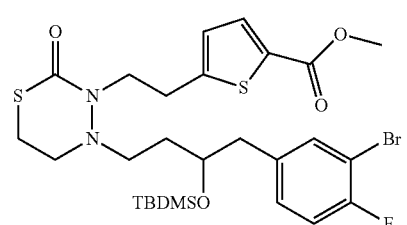

The intermediate Z-6-6 was synthesized according to the method described in Reference Example Z-6-4 by using the intermediate Z-4-6 (562.8 mg) instead of the intermediate Z-4-4, and thus the title compound (719.7 mg) was obtained.
(Intermediate Z-6-6: LCMS m/z 645.3 (MH$^+$), retention time 1.64 minutes, LC conditions LC-6)

Reference Example Z-7-20: Methyl 5-(2-(4-(3-((tert-butyldimethylsilyl)oxy)-4-(4-fluoro-3-(thiophen-3-ylethynyl)phenyl)butyl)-2-oxo-1,3,4-thiadiazinan-3-yl)ethyl)thiophene-2-carboxylate (Intermediate Z-7-20)

[Formula 165]

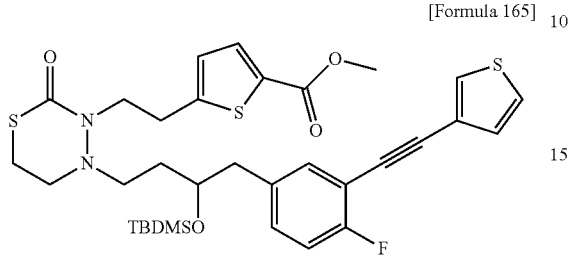

The intermediate Z-7-20 was synthesized according to the method described in Reference Example C-4 by using the intermediate Z-6-6 (15.0 mg) instead of the intermediate C-2-2, and thus the title compound (15.3 mg) was obtained.

(Intermediate Z-7-20: LCMS m/z 673.4 (MH$^+$), retention time 1.87 minutes, LC conditions LC-6)

Example 20: 5-(2-(4-(4-(4-Fluoro-3-(thiophen-3-ylethynyl)phenyl)-3-hydroxybutyl)-2-oxo-1,3,4-thiadiazinan-3-yl)ethyl)thiophene-2-carboxylic Acid

[Formula 166]

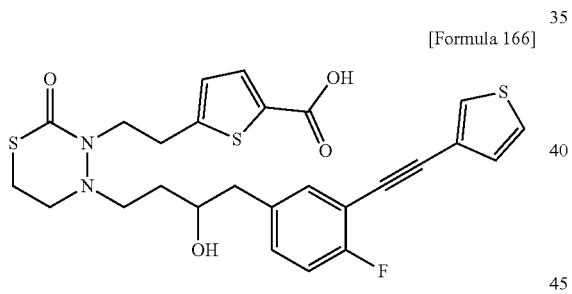

A solution of the intermediate Z-7-20 (15.3 mg) in tetrahydrofuran (345 μL) was cooled to 0° C., tetrabutylammonium fluoride (1 mol/L solution in tetrahydrofuran, 69 μL) was added to the solution, and the mixture was stirred at room temperature for 4 hours. To the reaction mixture, tetrabutylammonium fluoride (1 mol/L solution in tetrahydrofuran, 70 and tetrahydrofuran (350 μL) were added, and the mixture was stirred at room temperature for further 2.5 hours. To the reaction mixture, methanol (345 μL), and 1 mol/L aqueous sodium hydroxide (345 μL) were added, and the mixture was stirred overnight at room temperature. To the reaction mixture, 1 mol/L hydrochloric acid, and ethyl acetate were added for extraction, and then the organic layer was washed with 1 mol/L hydrochloric acid, and dried. The solvent was evaporated under reduced pressure, and the resulting residue was purified with an anion exchange resin to obtain the title compound (15.3 mg).

(LCMS m/z 545.2 (MH$^+$), retention time 1.67 minutes, LC conditions LC-1)

Reference Example X-1: 4-Phenylthiophene-3-carboaldehyde (Intermediate X-1)

[Formula 167]

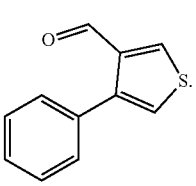

To a solution of (4-formylthiophen-3-yl)boronic acid (0.5 g, COMBI-BLOCKS) in n-butanol (32 mL), bromothiophene (1.0 mL, TCI), water (6.4 mL), palladium acetate (36 mg), 2-dicyclohexylphosphino-2',6'-dimethoxybiphenyl (132 mg), and potassium phosphate (1.36 g) were successively added, and the resulting mixture was stirred overnight at 95° C. under a nitrogen gas atmosphere. To the reaction mixture, diethyl ether was added, and then the organic layer was washed with water, and dried. The solvent was evaporated under reduced pressure, and the resulting residue was purified by column chromatography (hexane/ethyl acetate) to obtain the title compound (445 mg) was obtained.

(Intermediate X-1: LCMS m/z 189.0 (MH$^+$), retention time 1.54 minutes, LC conditions LC-1)

Reference Example X-2: 3-Ethynyl-4-phenylthiophene (Intermediate X-2)

[Formula 168]

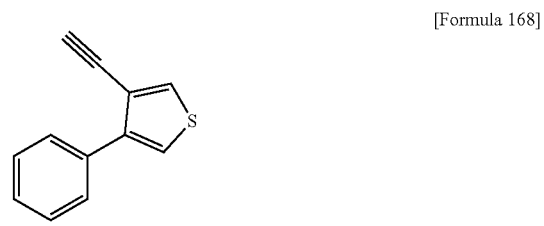

To a solution of dimethyl (1-diazo-2-oxopropyl)phosphonate (727 mg, TCI) in methanol (14.9 mL), the intermediate X-1 (445 mg) was added, and the mixture was cooled to 0° C. To the reaction mixture, potassium carbonate (686 mg) was added portionwise, and the mixture was stirred overnight at room temperature. To the reaction mixture, saturated aqueous ammonium chloride was added, and the mixture was extracted with diethyl ether. The organic layer was dried, then the solvent was evaporated under reduced pressure, and the resulting residue was purified by column chromatography (hexane/ethyl acetate) to obtain the title compound (384 mg).

(Intermediate X-2: LCMS m/z 185.1 (MH$^+$), retention time 1.81 minutes, LC conditions LC-1)

Reference Example Z-7-21: Methyl 5-(2-(4-(3-((tert-butyldimethylsilyl)oxy)-4-(3-((4-phenylthiophen-3-yl)ethynyl)phenyl)butyl)-2-oxo-1,3,4-thiadiazinan-3-yl)ethyl)thiophene-2-carboxylate (Intermediate Z-7-21)

[Formula 169]

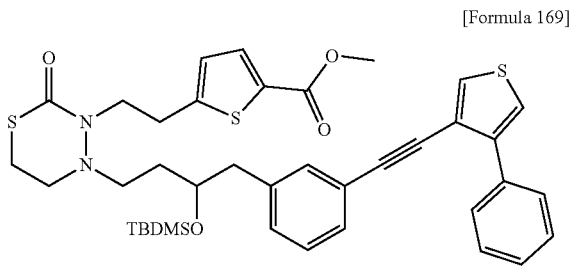 [SMILES: COC(=O)c1ccc(CCN2C(=O)SCCN2CCC(Cc2cccc(C#Cc3cscc3-c3ccccc3)c2)O[Si](C)(C)C(C)(C)C)s1]

The intermediate Z-7-21 was synthesized according to the method described in Reference Example C-4 by using the intermediate Z-6 (15.0 mg) instead of the intermediate C-2-2, and the intermediate X-2 (9.4 mg) instead of 3-ethynylthiophene, and thus the title compound (15.2 mg) was obtained.

(Intermediate Z-7-21: LCMS m/z 731.21 (MH$^+$), retention time 2.41 minutes, LC conditions LC-6)

Example 21: 5-(2-(4-(3-Hydroxy-4-(3-((4-phenylthiophen-3-yl)ethynyl)phenyl)butyl)-2-oxo-1,3,4-thiadiazinan-3-yl)ethyl)thiophene-2-carboxylic Acid

[Formula 170]

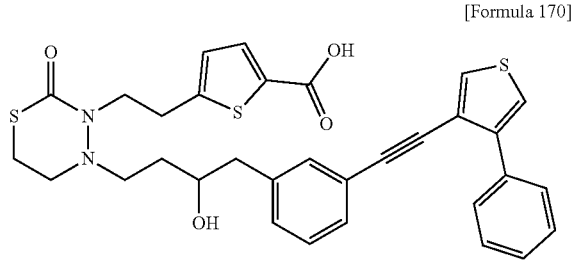 [SMILES: O=C(O)c1ccc(CCN2C(=O)SCCN2CCC(O)Cc2cccc(C#Cc3cscc3-c3ccccc3)c2)s1]

Synthesis was performed according to the method described in Example 18 by using the intermediate Z-7-21 (15.2 mg) instead of the intermediate Z-7-18 to obtain the title compound (5.7 mg).

(LCMS m/z 603.0 (MH$^+$), retention time 1.87 minutes, LC conditions LC-1)

Reference Example T-2: 2-(4-Bromothiophen-2-yl)-N-methoxy-N-methylacetamide (Intermediate T-2)

[Formula 171]

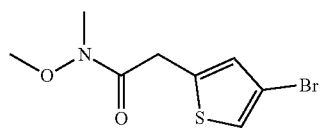

A solution of 2-(4-bromothiophen-2-yl)acetic acid (1.0 g) in dichloromethane (9 mL) was cooled to 0° C., N,O-dimethylhydroxylamine hydrochloride (882 mg), 1-ethyl-3-(3-dimethylaminopropyl)carbodiimide hydrochloride (1.04 g), N,N-dimethyl-4-aminopyridine (55 mg), and diisopropylethylamine (3.38 mL) were added to the solution, then diisopropylethylamine (0.35 mL) was further added, and the mixture was stirred at room temperature for 41 hours. The reaction mixture was concentrated, and then ethyl acetate and water were added, 1 mol/L hydrochloric acid was added for partitioning, and extraction was further performed twice with ethyl acetate. The organic layer was successively washed with 1 mol/L hydrochloric acid, water, saturated aqueous sodium hydrogencarbonate, water, and saturated brine, dried over magnesium sulfate, and concentrated under reduced pressure to obtain the title compound (891 mg).

(Intermediate T-2: LCMS m/z 264.2, 266 (MH$^+$), retention time 1.36 minutes, LC conditions LC-1)

Reference Example T-3: 1-(4-Bromothiophen-2-yl)-4-(methoxy(methyl)amino)butan-2-one (Intermediate T-3)

[Formula 172]

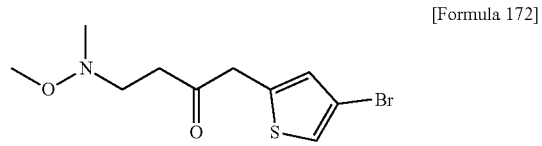

A solution of the intermediate T-2 (200 mg) in 1,2-dimethoxyethane (7 mL) was cooled to 0° C. under a nitrogen atmosphere. To the reaction mixture, vinylmagnesium bromide (1 mol/L solution in tetrahydrofuran, 1.1 mL, ALDRICH) was added, and the mixture was stirred at the same temperature for 2 hours and 50 minutes. To the reaction mixture, 1 mol/L hydrochloric acid was added to make the mixture acidic still at 0° C., and then the mixture was extracted 3 times with ethyl acetate. The organic layer was washed with water, and saturated brine, dried over magnesium sulfate, and then concentrated under reduced pressure to obtain the title compound (172.8 mg).

(Intermediate T-3: LCMS m/z 292.1, 294 (MH$^+$), retention time 1.55 minutes, LC conditions LC-1)

Reference Example T-4: Methyl 5-(2-(4-(4-(4-bromothiophen-2-yl)-3-oxobutyl)-2-oxo-1,3,4-thiadiazinan-3-yl)ethyl)thiophene-2-carboxylate (Intermediate T-4)

[Formula 173]

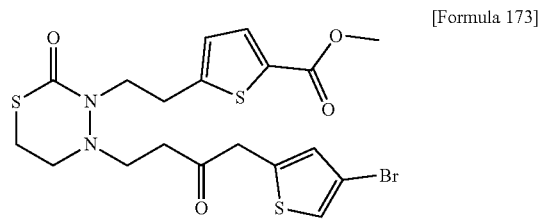 [SMILES: COC(=O)c1ccc(CCN2C(=O)SCCN2CCC(=O)Cc2cc(Br)cs2)s1]

The intermediate T-3 (172.8 mg), and the intermediate Z-3 (181 mg) were dissolved in ethanol (5 mL), water (5 mL) was added to the solution, and the mixture was stirred at 105° C. for 16.5 hours. The reaction mixture was poured into saturated brine diluted with water, and the mixture was extracted 3 times with chloroform. The organic layer was washed with saturated brine, and dried over magnesium sulfate, and then the solvent was evaporated under reduced pressure. The resulting residue was purified by column chromatography (n-hexane/ethyl acetate) to obtain the title compound (112.0 mg).

(Intermediate T-4: LCMS m/z 517.0, 519.1 (MH$^+$), retention time 1.76 minutes, LC conditions LC-1)

Reference Example T-5: Methyl 5-(2-(4-(4-(4-bromothiophen-2-yl)-3-hydroxybutyl)-2-oxo-1,3,4-thiadiazinan-3-yl)ethyl)thiophene-2-carboxylate (Intermediate T-5)

[Formula 174]

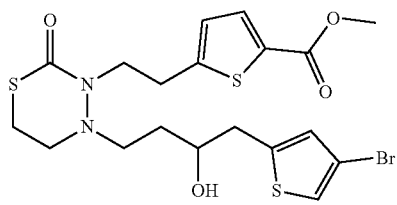

A solution of the intermediate T-4 (112 mg) in methanol (2 mL) was cooled to 0° C., sodium borohydride (12.3 mg) was added portionwise to the solution. The reaction mixture was stirred at room temperature for 3 hours, and then poured into water, and the mixture was extracted 3 times with ethyl acetate. The organic layer was washed with water, and then with saturated brine, and dried over magnesium sulfate, and then the solvent was evaporated under reduced pressure to obtain the title compound (99.6 mg).

(Intermediate T-5: LCMS m/z 519.08, 521.08 (MH$^+$), retention time 1.70 minutes, LC conditions LC-1)

Reference Example T-6: Methyl 5-(2-(4-(3-acetoxy-4-(4-bromothiophen-2-yl)butyl)-2-oxo-1,3,4-thiadiazinan-3-yl)ethyl)thiophene-2-carboxylate (Intermediate T-6)

[Formula 175]

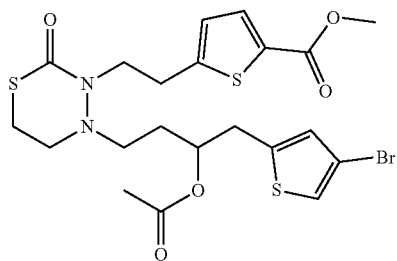

A solution of the intermediate T-5 (95.7 mg) in dichloromethane (1.8 mL) was cooled to 0° C., acetic anhydride (348 µL), and pyridine (741 µL) were added to the solution, the mixture was stirred at room temperature for 17 hours, then acetic anhydride (348 µL) was added to the mixture, and the resulting mixture was stirred at room temperature for further 4 hours. Water was added to the reaction mixture, and then the mixture was extracted 3 times with chloroform. The organic layer was washed with saturated aqueous sodium hydrogencarbonate, and then with saturated brine, and dried over magnesium sulfate, and then the solvent was evaporated under reduced pressure. The resulting residue was purified by column chromatography (n-hexane/ethyl acetate) to obtain the title compound.

(Intermediate T-6: LCMS m/z 561.1, 563.1 (MH$^+$), retention time 1.89 minutes, LC conditions LC-1)

Example 22: 5-(2-(4-(3-Hydroxy-4-(4-(thiophen-3-ylethynyl)thiophen-2-yl)butyl)-2-oxo-1,3,4-thiadiazinan-3-yl)ethyl)thiophene-2-carboxylic Acid

[Formula 176]

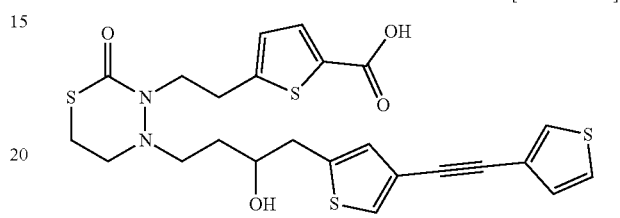

[Step a]

Methyl 5-(2-(4-(3-acetoxy-4-(4-(thiophen-3-ylethynyl)thiophen-2-yl)butyl)-2-oxo-1,3,4-thiadiazinan-3-yl)ethyl)thiophene-2-carboxylate (Intermediate T-7)

[Formula 177]

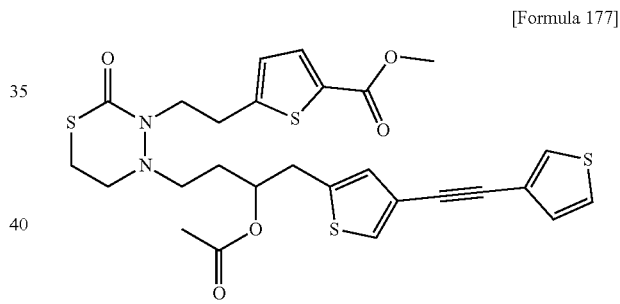

To a solution of the intermediate T-6 (17.5 mg) in acetonitrile (1 mL), bis(acetonitrile)palladium chloride (1.2 mg), 2-dicyclohexylphosphino-2',4',6'-triisopropylbiphenyl (6.7 mg), cesium carbonate (13.2 mg), and 3-ethynylthiophene (5.6 µL) were successively added, and the resulting mixture was stirred at 60° C. for 17 hours under an argon gas atmosphere. The reaction mixture was filtered through filter paper covered with Celite, and the residue remained on Celite was washed with ethyl acetate. The filtrate and the wash liquid were mixed, the solvent was evaporated under reduced pressure, and then the resulting residue was purified by column chromatography (n-hexane/ethyl acetate) to obtain a mixture (18.6 mg) of the intermediate T-6 and the title compound. To a solution of the resulting mixture in acetonitrile (2 mL), bis(acetonitrile)palladium chloride (1.2 mg), 2-dicyclohexyl-phosphino-2',4',6'-triisopropylbiphenyl (6.7 mg), cesium carbonate (13.2 mg), and 3-ethynylthiophene (6.14 µL) were successively added, and the resulting mixture was stirred at 60° C. for 19 hours under an argon gas atmosphere. The reaction mixture was filtered through filter paper covered with Celite, and the residue remained on Celite was washed with ethyl acetate. The filtrate and the wash liquid were mixed, the solvent was evaporated under reduced pressure, and then the resulting residue was purified by column chromatography (n-hexane/ethyl acetate) to obtain the title compound (14.2 mg).

(Intermediate T-7: LCMS m/z 589.1 (MH⁺), retention time 2.03 minutes, LC conditions LC-1)

[Step b]

5-(2-(4-(3-Hydroxy-4-(4-(thiophen-3-ylethynyl)thiophen-2-yl)butyl)-2-oxo-1,3,4-thiadiazinan-3-yl)ethyl)thiophene-2-carboxylic Acid To a solution of the intermediate T-7 (14.2 mg) in tetrahydrofuran (0.36 mL), 1 mol/L aqueous lithium hydroxide (0.36 mL) was added, and the mixture was stirred overnight at room temperature. The reaction mixture was cooled to 0° C., and 1 mol/L hydrochloric acid (0.36 mL) was added to the mixture. The mixture was diluted with water, and extracted 3 times with chloroform, then the organic layer was washed with saturated brine, and dried over magnesium sulfate, and the solvent was evaporated under reduced pressure. The resulting residue was purified by column chromatography (chloroform/methanol) to obtain the title compound (3.5 mg).

(LCMS m/z 533.0 (MH⁺), retention time 1.64 minutes, LC conditions LC-1)

Example 23: (S)-5-(2-(4-(3-Hydroxy-4-(3-(thiophen-3-ylethynyl)phenyl)butyl)-2-oxo-1,3,4-thiadiazinan-3-yl)ethyl)thiophene-2-carboxylic Acid

[Formula 178]

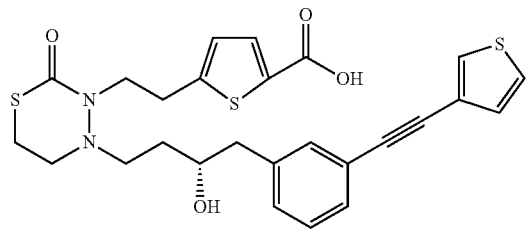

[Step a]

(S)-Methyl 5-(2-(4-(3-hydroxy-4-(3-(thiophen-3-ylethynyl)phenyl)butyl)-2-oxo-1,3,4-thiadiazinan-3-yl)ethyl)thiophene-2-carboxylate (Intermediate Z-17-S)

[Formula 179]

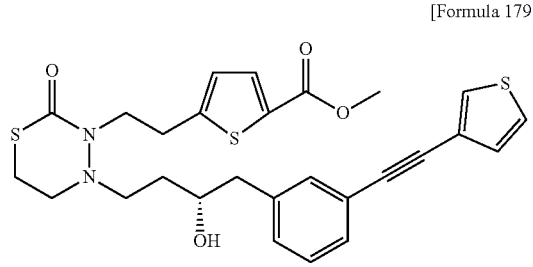

The intermediate Z-17 (592 mg) was subjected to separation by HPLC using a chiral column (HPLC apparatus was preparative purification apparatus produced by Japan Waters, chiral column CHIRALCEL AD-H (Daicel Corporation), eluent ethanol, flow rate 0.5 mL/minute, retention time 14.91 minutes) to obtain the title compound (194.2 mg).

[Step b]

(S)-5-(2-(4-(3-Hydroxy-4-(3-(thiophen-3-ylethynyl)phenyl)butyl)-2-oxo-1,3,4-thiadiazinan-3-yl)ethyl)thiophene-2-carboxylic Acid Synthesis was performed according to the method described in Example 1 by using the intermediate Z-17-S (41.4 mg) instead of the intermediate Z-17 to obtain the title compound (31.8 mg).

(LCMS m/z 527.2 (MH⁺), retention time 1.68 minutes, LC conditions LC-1)

Reference Example U: (S)-Methyl 5-(2-(4-(4-(3-bromophenyl)-3-hydroxybutyl)-2-oxo-1,3,4-thiadiazinan-3-yl)ethyl)thiophene-2-carboxylate (Intermediate U)

[Formula 180]

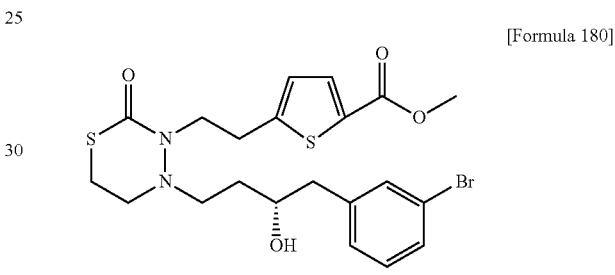

The intermediate Z-5 (1 g) was subjected to separation by HPLC using a chiral column (HPLC apparatus was preparative purification apparatus produced by Japan Waters, chiral column CHIRALCEL OJ-H (Daicel Corporation), eluent methanol, flow rate 0.5 mL/minute, retention time 20.72 minutes) to obtain the title compound (309 mg).

Reference Example V-1: (S)-Methyl 5-(2-(4-(4-(3-bromophenyl)-3-((tert-butyldimethylsilyl)oxy)butyl)-2-oxo-1,3,4-thiadiazinan-3-yl)ethyl)thiophene-2-carboxylate (Intermediate V-1)

[Formula 181]

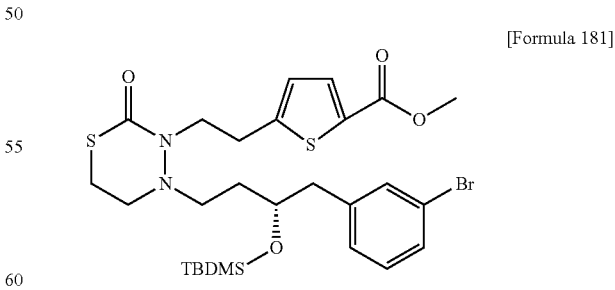

Synthesis was performed according to the method described in Reference Example Z-6 by using the intermediate U (299.3 mg) instead of the intermediate Z-5 to obtain the title compound (333.9 mg).

(Intermediate V-1: LCMS m/z 627.35, 629.35 (MH⁺), retention time L79 minutes, LC conditions NLC-1)

Reference Example V-2: (S)-Methyl 5-(2-(4-(3-((tert-butyldimethylsilyl)oxy)-4-(3-((trimethylsilyl)ethynyl)phenyl)butyl)-2-oxo-1,3,4-thiadiazinan-3-yl)ethyl)thiophene-2-carboxylate (Intermediate V-2)

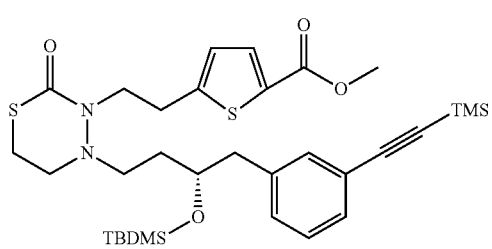

[Formula 182]

Synthesis was performed according to the method described in Reference Example Z-21 by using the intermediate V-1 (333.9 mg) instead of the intermediate Z-6 to obtain the title compound (91.3 mg).

(Intermediate V-2: LCMS m/z 645.49 (MH⁺), retention time 2.38 minutes, LC conditions NLC-6)

Reference Example V-3: (S)-Methyl 5-(2-(4-(3-((tert-butyldimethylsilyl)oxy)-4-(3-ethynylphenyl)butyl)-2-oxo-1,3,4-thiadiazinan-3-yl)ethyl)thiophene-2-carboxylate (Intermediate V-3)

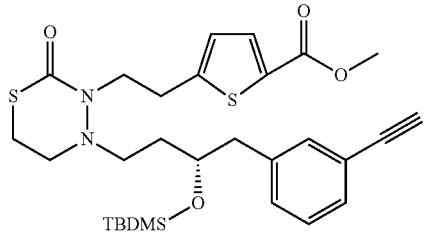

[Formula 183]

Synthesis was performed according to the method described in Reference Example Z-22 by using the intermediate V-2 (91.3 mg) instead of the intermediate Z-21 to obtain the title compound (91.6 mg).

(Intermediate V-3: LCMS m/z 573.45 (MH⁺), retention time 1.41 minutes, LC conditions NLC-6)

Example 24: (S)-5-(2-(4-(4-(3-((2-Cyanothiophen-3-yl)ethynyl)phenyl)-3-hydroxybutyl)-2-oxo-1,3,4-thiadiazinan-3-yl)ethyl)thiophene-2-carboxylic Acid

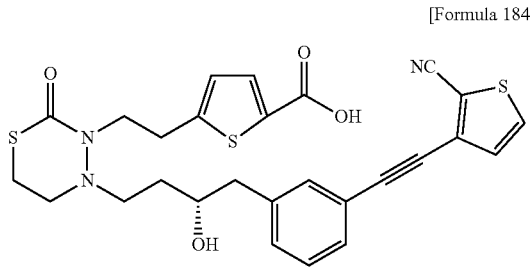

[Formula 184]

[Step a]

(S)-Methyl 5-(2-(4-(3-((tert-butyldimethylsilyl)oxy)-4-(3-((2-cyanothiophen-3-yl)ethynyl)phenyl)butyl)-2-oxo-1,3,4-thiadiazinan-3-yl)ethyl)thiophene-2-carboxylate (Intermediate Z-24-1)

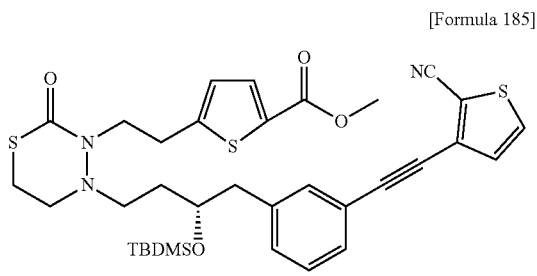 [SMILES: COC(=O)c1ccc(CCN2C(=O)SCCN2CC[C@H](Cc2cccc(C#Cc3ccsc3C#N)c2)O[Si](C)(C)C(C)(C)C)s1]

[Formula 185]

To a solution of the intermediate V-3 (50.6 mg) in acetonitrile (1 mL), bis(acetonitrile)palladium chloride (2.0 mg), 2-dicyclohexylphosphino-2',4',6'-triisopropylbiphenyl (11.2 mg), cesium carbonate (51.1 mg), and 3-bromothiophene-2-carbonitrile (73.8 mg) were successively added, and the resulting mixture was stirred at 60° C. for 0.75 hour under a nitrogen gas atmosphere. The reaction mixture was filtered through filter paper covered with Celite, and the residue remained on Celite was washed with a mixed solvent of chloroform and methanol (9:1). The filtrate and the wash liquid were mixed, the solvent was evaporated under reduced pressure, and then the resulting residue was purified by column chromatography (hexane/ethyl acetate) to obtain the title compound (10.1 mg).

(Intermediate Z-24-1: LCMS m/z 680.44 (MH+), retention time 1.73 minutes, LC conditions NLC-6)

[Step b]

(S)-Methyl 5-(2-(4-(4-(3-((2-cyanothiophen-3-yl)ethynyl)phenyl)-3-hydroxybutyl)-2-oxo-1,3,4-thiadiazinan-3-yl)ethyl)thiophene-2-carboxylate (Intermediate Z-24-2)

[Formula 186]

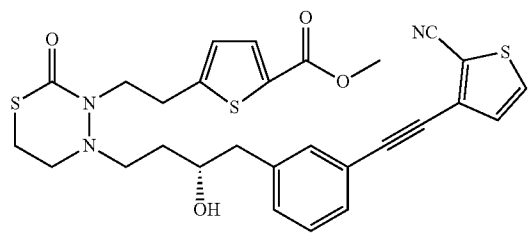

To a solution of the intermediate Z-24-1 (10.1 mg) in tetrahydrofuran (0.5 mL), tetrabutylammonium fluoride (1 mol/L solution in tetrahydrofuran, 44.6 μL) was added, and the mixture was stirred at room temperature for 1 hour. The reaction mixture was purified by column chromatography (hexane/ethyl acetate) to obtain the title compound (9.3 mg).

(Intermediate Z-24-2: LCMS m/z 566.35 (MH+), retention time 1.77 minutes, LC conditions NLC-6)

[Step c]

(S)-5-(2-(4-(4-(3-((2-Cyanothiophen-3-yl)ethynyl)phenyl)-3-hydroxybutyl)-2-oxo-1,3,4-thiadiazinan-3-yl)ethyl)thiophene-2-carboxylic Acid To a solution of the intermediate Z-24-2 (9.3 mg) in tetrahydrofuran (400 μL), 1 mol/L aqueous sodium hydroxide (197 μL) was added, and the mixture was stirred at room temperature for 60 hours. To the reaction mixture, 1 mol/L hydrochloric acid (400 μL) was added, the mixture was extracted 3 times with chloroform, and then the organic layer was washed with saturated brine, and dried. The solvent was evaporated under reduced pressure. The resulting residue was purified by column chromatography (methanol/chloroform) to obtain the title compound (7.5 mg).

(LCMS m/z 552.30.2 (MH+), retention time 1.23 minutes, LC conditions NLC-1)

Example 25: (S)-5-(2-(4-(3-Hydroxy-4-(3-(thiazol-4-ylethynyl)phenyl)butyl)-2-oxo-1,3,4-thiadiazinan-3-yl)ethyl)thiophene-2-carboxylic Acid

[Formula 187]

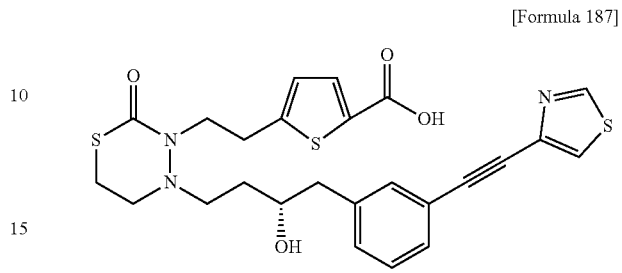

[Step a]

(S)-Methyl 5-(2-(4-(3-((tert-butyldimethylsilyl)oxy)-4-(3-(thiazol-4-ylethynyl)phenyl)butyl)-2-oxo-1,3,4-thiadiazinan-3-yl)ethyl)thiophene-2-carboxylate (Intermediate Z-25-1)

[Formula 188]

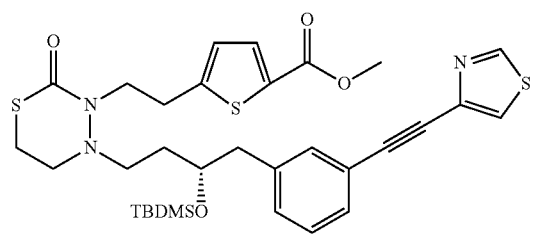

Synthesis was performed according to the method described in Example 24, Step a by using 4-bromothiazole (28.6 μL) instead of 3-bromothiophene-2-carbonitrile to obtain the title compound (21.0 mg).

(Intermediate Z-25-1: LCMS m/z 656.43 (MH+), retention time 1.37 minutes, LC conditions NLC-1)

[Step b]

(S)-5-(2-(4-(3-Hydroxy-4-(3-(thiazol-4-ylethynyl)phenyl)butyl)-2-oxo-1,3,4-thiadiazinan-3-yl)ethyl)thiophene-2-carboxylic Acid To a solution of the intermediate Z-25-1 (21.0 mg) in tetrahydrofuran (1 mL), tetrabutylammonium fluoride (1 mol/L solution in tetrahydrofuran, 92.6 μL) was added, and the mixture was stirred at room temperature for 3 hours. The reaction mixture was purified by column chromatography (hexane/ethyl acetate). To a solution of the resulting intermediate (12.2 mg) in tetrahydrofuran (540 μL), and methanol (270 μL), 1 mol/L aqueous sodium hydroxide (270 μL) was added, and the mixture was stirred at room temperature for 16 hours. To the reaction mixture, 1 mol/L hydrochloric acid was added, the mixture was extracted 5 times with ethyl acetate, and then the organic layer was washed with saturated brine, and dried. The solvent was evaporated under reduced pressure to obtain the title compound (12.5 mg).

(LCMS m/z 528.29 (MH+), retention time 1.08 minutes, LC conditions NLC-1)

Example 26: (S)-5-(2-(4-(4-(3-(Furan-3-ylethynyl)phenyl)-3-hydroxybutyl)-2-oxo-1,3,4-thiadiazinan-3-yl)ethyl)thiophene-2-carboxylic Acid

[Formula 189]

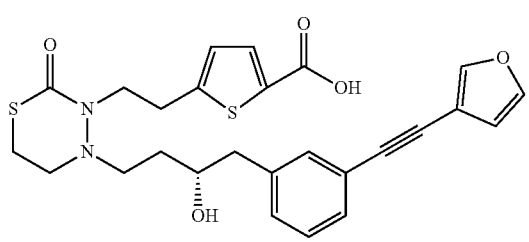

Synthesis was performed according to the method described in Example 25 by using 3-bromofuran (31.2 mg) instead of 4-bromothiazole, and then the resultant was purified by column chromatography (methanol/chloroform) to obtain the title compound (5.1 mg).

(LCMS m/z 511.35 (MH$^+$), retention time 1.23 minutes, LC conditions NLC-1)

Reference Example Z-27: (E)-Methyl 5-(2-(4-(3-((tert-butyldimethylsilyl)oxy)-4-(3-(2-(thiophen-3-yl)vinyl)phenyl)butyl)-2-oxo-1,3,4-thiadiazinan-3-yl)ethyl)thiophene-2-carboxylate (Intermediate Z-27)

[Formula 190]

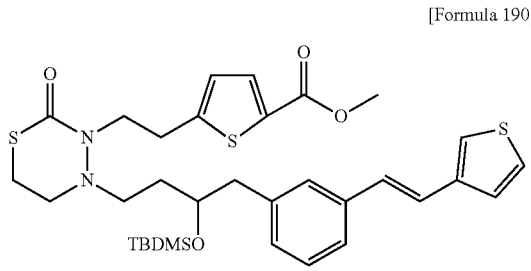 [SMILES: COC(=O)c1ccc(CCN2C(=O)SCCN2CCC(Cc2cccc(/C=C/c3ccsc3)c2)O[Si](C)(C)C(C)(C)C)s1]

To a solution of the intermediate Z-6 (50.0 mg) in 1,4-dioxane (637 μL), (E)-4,4,5,5-tetramethyl-2-(2-(thiophen-3-yl)vinyl)-1,3,2-dioxaborolane (22.6 mg, ALDRICH), bis(triphenylphosphine)palladium chloride (5.6 mg), sodium carbonate (21.1 mg), and water (199 μL) were successively added, and the resulting mixture was stirred at 85° C. for 11 hours under a nitrogen gas atmosphere. To the reaction mixture, water was added, and the mixture was extracted with ethyl acetate. The organic layer was dried, then the solvent was evaporated under reduced pressure, and the resulting residue was purified by column chromatography (hexane/ethyl acetate) to obtain the title compound (44.5 mg).

(Intermediate Z-27: LCMS m/z 657.3 (MH$^+$), retention time 1.93 minutes, LC conditions LC-6)

Example 27: (E)-5-(2-(4-(3-Hydroxy-4-(3-(2-(thiophen-3-yl)vinyl)phenyl)butyl)-2-oxo-1,3,4-thiadiazinan-3-yl)ethyl)thiophene-2-carboxylic Acid

[Formula 191]

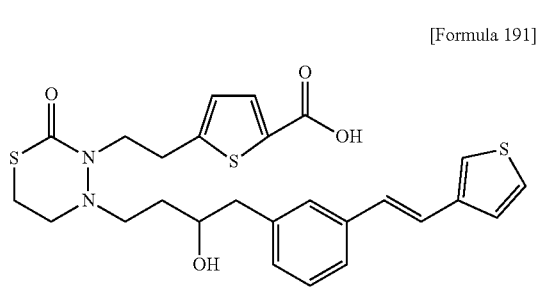 [SMILES: O=C(O)c1ccc(CCN2C(=O)SCCN2CCC(O)Cc2cccc(/C=C/c3ccsc3)c2)s1]

Synthesis was performed according to the method described in Example 18 by using the intermediate Z-27 (24.8 mg) instead of the intermediate Z-7-18 to obtain the title compound (17.8 mg).

(LCMS m/z 529.1 (MH$^+$), retention time 1.63 minutes, LC conditions LC-1)

Reference Example Z-14-5: Methyl 4-chloro-5-(2-(2-oxo-4-(3-oxo-4-(3-(pyridin-2-ylethynyl)phenyl)butyl)-1,3,4-thiadiazinan-3-yl)ethyl)thiophene-2-carboxylate (Intermediate Z-14-5)

[Formula 192]

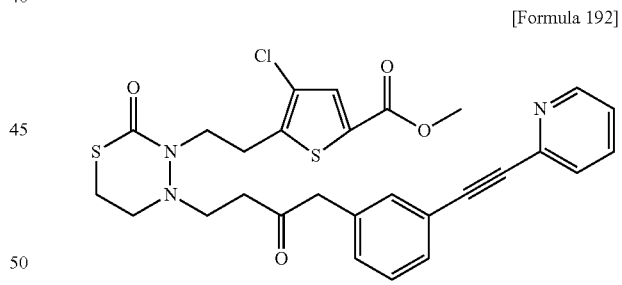

To the intermediate Z-4-3 (100 mg), diethylamine (850 μL), 2-ethynylpyridine (22.8 μL), copper(I) iodide (2.9 mg), and tetrakis(triphenylphosphine)palladium (3.9 mg) were successively added, and the mixture was stirred at room temperature for 15.5 hours under a nitrogen gas atmosphere. The reaction mixture was diluted with ethyl acetate, then the solvent was evaporated, and the resulting residue was purified by column chromatography (toluene/acetonitrile) to obtain the title compound (47.6 mg).

(Intermediate Z-14-5: LCMS m/z 570.425 (MH$^+$), retention time 4.86 minutes, LC conditions FLC-1))

Example 28: 4-Chloro-5-(2-(4-(3-hydroxy-4-(3-(pyridin-2-ylethynyl)phenyl)butyl)-2-oxo-1,3,4-thiadiazinan-3-yl)ethyl)thiophene-2-carboxylic Acid

[Formula 193]

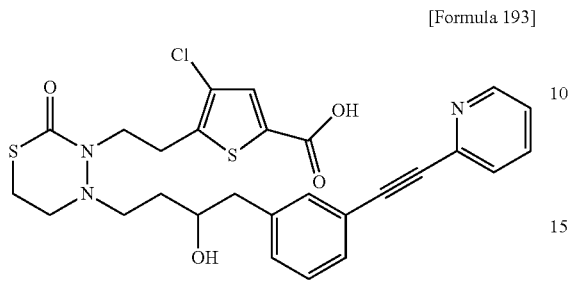

To a solution of the intermediate Z-14-5 (47.6 mg) in methanol (840 μL), sodium borohydride (4.8 mg) was added portionwise. The mixture was stirred at room temperature for 0.5 hour, and then water, and ethyl acetate were added to the mixture, and the organic layer was successively washed with saturated aqueous sodium hydrogencarbonate, and saturated brine, and dried. The solvent was evaporated under reduced pressure, and then tetrahydrofuran (640 μL), methanol (640 μL), and 2 mol/L aqueous sodium hydroxide (640 μL) were added to the residue. The reaction mixture was stirred at room temperature for 1.8 hours, and then cooled to 0° C., and 2 mol/L hydrochloric acid (640 μL) was added portionwise to the mixture. To the reaction mixture, ethyl acetate was added, and the organic layer was washed with saturated brine, and dried. The solvent was evaporated under reduced pressure, and the resulting residue was purified by thin layer chromatography (toluene/ethanol/acetic acid) to obtain the title compound (15.0 mg).

(LCMS m/z 556.023 (MH$^+$), retention time 4.49 minutes, LC conditions FLC-1)

Reference Example Z-29-1: 2-tert-Butyl 1-(2-chloroethyl) 1-(2-(5-(methoxycarbonyl)thiophen-2-yl)ethyl)hydrazine-1,2-dicarboxylate (Intermediate Z-29-1)

[Formula 194]

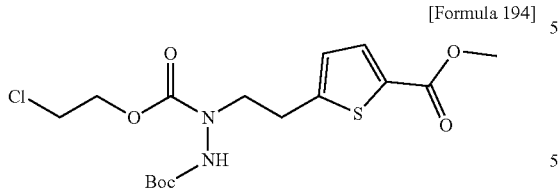

To a solution of the intermediate A-6 (5.0 g) in acetonitrile (165 mL), potassium carbonate (0.46 g) was added, and the mixture was cooled to 0° C. 2-Chloroethyl chloroformate (2.07 mL) was slowly added to the mixture, and the resulting mixture was stirred at the same temperature for 1 hour. To the reaction mixture, water was added, and the resulting mixture was warmed to room temperature, and extracted 3 times with ethyl acetate. The organic layer was washed with water, and then with saturated brine, and dried, and then the solvent was evaporated under reduced pressure to obtain the title compound (8.34 g).

(Intermediate Z-29-1: LCMS m/z 307.14, 309.11 (MH$^+$-Boc), retention time 1.64 minutes, LC conditions LC-1)

Reference Example Z-29-2: tert-Butyl 3-(2-(5-(methoxycarbonyl)thiophen-2-yl)ethyl)-2-oxo-1,3,4-oxadiazinane-4-carboxylate (Intermediate Z-29-2)

[Formula 195]

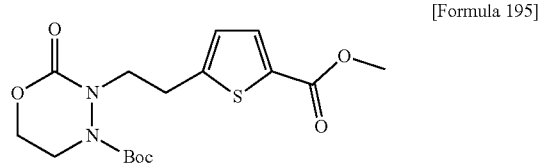 [SMILES: COC(=O)c1ccc(CCN2C(=O)OCCN2C(=O)OC(C)(C)C)s1]

A solution of the intermediate Z-29-1 (8.34 g) in DMF (140 mL) was cooled to 0° C., sodium hydride (55%, 0.87 g) was added portionwise over 30 minutes, and the mixture was stirred for 2 hours. The reaction mixture was returned to room temperature, and stirred for 1 hour, then sodium hydride (55%, 0.1 g) was added to the mixture again at 0° C., and the mixture was stirred at room temperature for 15 hours. The reaction mixture was cooled to 0° C., water was added, and the resulting mixture was extracted 4 times with ethyl acetate. The organic layer was washed twice with water, and once with saturated brine, and dried, and then the solvent was evaporated under reduced pressure. The resulting residue was purified by column chromatography (hexane/ethyl acetate) to obtain the title compound (1.75 g).

(Intermediate Z-29-2: LCMS m/z 371.3 (MH$^+$), retention time 1.51 minutes, LC conditions LC-1)

Reference Example Z-29-3: Methyl 5-(2-(2-oxo-1,3,4-oxadiazinan-3-yl)ethyl)thiophene-2-carboxylate (Intermediate Z-29-3)

[Formula 196]

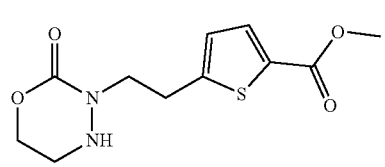

A solution of the intermediate Z-29-2 (1.75 g) in dichloromethane (25 mL) was cooled to 0° C., trifluoroacetic acid (12.5 mL) was added to the solution, and the mixture was stirred at room temperature for 1 hour. The reaction mixture was cooled to 0° C., neutralized with 5 M aqueous sodium hydroxide, and then extracted 3 times with chloroform. The organic layer was washed with water, and then dried, and the solvent was evaporated under reduced pressure. The residue was purified with a silica gel short column (chloroform, then ethyl acetate), and then the deposited solid was washed with diethyl ether to obtain the title compound (0.90 g).

(Intermediate Z-29-3: LCMS m/z 271.2 (MH$^+$), retention time 0.94 minutes, LC conditions LC-1)

Reference Example Z-29-4: Methyl 5-(2-(4-(4-(3-iodophenyl)-3-oxobutyl)-2-oxo-1,3,4-oxadiazinan-3-yl)ethyl)thiophene-2-carboxylate (Intermediate Z-29-4)

[Formula 197]

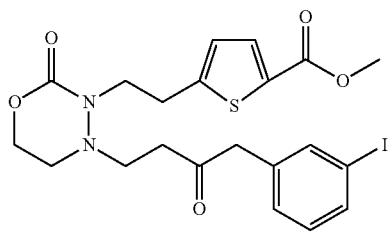

A solution of the intermediate C-2-2 (250 mg) in DME (5 mL) was cooled to 0° C. under a nitrogen flow, vinylmagnesium bromide (1 M solution, 1.2 mL) was added dropwise to the solution, and the mixture was stirred at the same temperature for 2 hours. The reaction mixture was made acidic by addition of 2 M hydrochloric acid, and then water was added to the mixture, and the resulting mixture was extracted 3 times with ethyl acetate. The organic layer was washed twice with water, and dried, and then the solvent was evaporated under reduced pressure.

To a flask containing the intermediate Z-29-3 (110.7 mg), and water (3.3 mL), a solution of the residue obtained above in ethanol (3.3 mL) was added, and the mixture was stirred at an external temperature of 110° C. for 15 hours. The reaction mixture was returned to room temperature, and then poured into water, and the resulting mixture was extracted 3 times with ethyl acetate. The organic layer was washed with saturated brine, and dried, and then the solvent was evaporated under reduced pressure. The resulting residue was purified by column chromatography (hexane/ethyl acetate) to obtain the title compound (126.2 mg).

(Intermediate Z-29-4: LCMS m/z 541.2 (MH$^+$), retention time L66 minutes, LC conditions LC-1)

Reference Example Z-29-5: Methyl 5-(2-(4-(3-hydroxy-4-(3-iodophenyl)butyl)-2-oxo-1,3,4-oxadiazinan-3-yl)ethyl)thiophene-2-carboxylate (Intermediate Z-29-5)

[Formula 198]

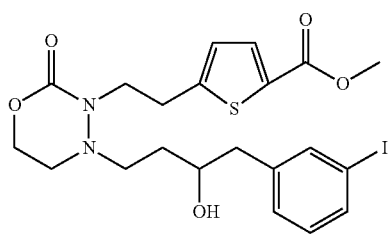

To a solution of the intermediate Z-29-4 (58.1 mg) in methanol (1 mL), sodium borohydride (6.1 mg) was added, and the mixture was stirred at room temperature for 1 hour. Water was added to the mixture, and the resulting mixture was extracted 3 times with ethyl acetate. The organic layer was washed with saturated brine, and dried, and then the solvent was evaporated under reduced pressure to obtain the title compound (61.4 mg).

(Intermediate Z-29-5: LCMS m/z 545.2 (MH$^+$), retention time 1.60 minutes, LC conditions LC-1)

Reference Example Z-29-6: Methyl 5-(2-(4-(3-acetoxy-4-(3-iodophenyl)butyl)-2-oxo-1,3,4-oxadiazinan-3-yl)ethyl)thiophene-2-carboxylate (Intermediate Z-29-6)

[Formula 199]

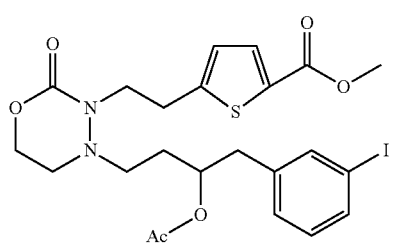

The intermediate Z-29-5 (61.4 mg) was dissolved in dichloromethane (2 mL), acetic anhydride (0.27 mL), and pyridine (0.23 mL) were added to the solution, and the mixture was stirred at room temperature 5.5 hours. To the reaction mixture, water was added, and the resulting mixture was extracted 3 times with chloroform. The organic layer was washed with water, and dried, and then the solvent was evaporated under reduced pressure. The residue was purified by short column chromatography to obtain the title compound (71.8 mg).

(Intermediate Z-29-6: LCMS m/z 587.26 (MH$^+$), retention time 1.82 minutes, LC conditions LC-1)

Reference Example Z-29-7: Methyl 5-(2-(4-(3-acetoxy-4-(3-(thiophen-3-ylethynyl)phenyl)butyl)-2-oxo-1,3,4-oxadiazinan-3-yl)ethyl)thiophene-2-carboxylate (Intermediate Z-29-7)

[Formula 200]

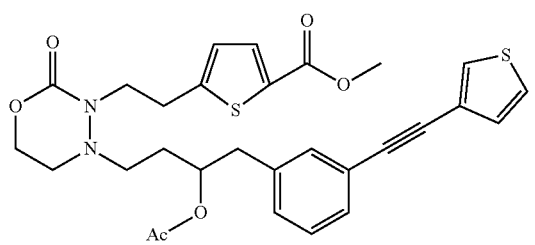

Synthesis was performed according to the method described in Reference Example Z-14 by using the intermediate Z-29-6 (71.8 mg) instead of the intermediate Z-4-2 to obtain the title compound (66.4 mg).

(Intermediate Z-29-7: LCMS m/z 567.36 (MH$^+$), retention time 1.94 minutes, LC conditions LC-1)

Example 29: 5-(2-(4-(3-Hydroxy-4-(3-(thiophen-3-ylethynyl)phenyl)butyl)-2-oxo-1,3,4-oxadiazinan-3-yl)ethyl)thiophene-2-carboxylic Acid

[Formula 201]

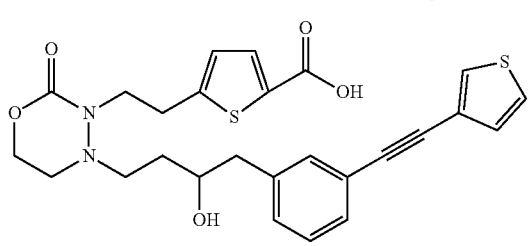

Synthesis was performed according to the method described in Example 22, Step b by using the intermediate Z-29-7 (66.4 mg) instead of the intermediate T-7 to obtain the title compound (45.6 mg).

(LCMS m/z 509.2 (MH$^+$), retention time 1.53 minutes, LC conditions LC-1)

Reference Example D-2: Methyl 4-(3-bromophenyl)-3-oxobutanoate (Intermediate D-2)

[Formula 202]

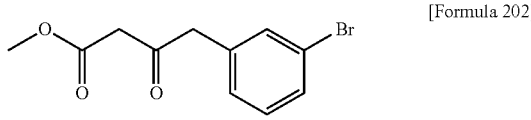

To a solution of monomethyl potassium malonate (0.885 kg), THF (4.077 kg), and magnesium chloride (0.47 kg) were added, and the mixture was stirred at 50° C. for 10 minutes. To this mixture, a reaction mixture obtained by adding a solution of carbonyldiimidazole (0.801 kg) in DMF (4.025 kg) to a solution of 3-bromophenylacetic acid (1.005 kg) in THF (2.023 kg), and stirring the mixture at room temperature for 1 hour was added. THF (0.508 kg) was further added to the reaction mixture, and the resulting mixture was stirred at 50° C. for 30 minutes. The reaction mixture was cooled to room temperature, ethyl acetate (8.071 kg) was added to the mixture, the organic layer was washed twice with 20% aqueous citric acid (6.032 kg), and then the solvent was evaporated under reduced pressure to obtain a concentrate (2.358 kg). To this concentrate, ethyl acetate (1.011 kg) was added to obtain a solution containing the intermediate D-2 (3.369 kg). The solution containing the intermediate D-2 was mixed with a solution obtained by a similar operation. To this mixture (6.770 kg), ethyl acetate (6.063 kg) was added, and 5% aqueous sodium hydrogencarbonate (10.055 kg), and sodium chloride (0.506 kg) were further added to wash the organic layer. 5% Aqueous sodium hydrogencarbonate (10.054 kg), and sodium chloride (0.503 kg) were added to further wash the organic layer. The organic layer was further washed with 20% aqueous sodium chloride (10.064 kg), ethyl acetate (1.01 kg) was added, and then the solvent was evaporated under reduced pressure to obtain the title compound (2.52 kg).

(LCMS m/z 268.9, 270.9 (MH$^-$), retention time 1.44 minutes, LC conditions NLC-1)

Reference Example D-3: Methyl (S)-4-(3-bromophenyl)-3-hydroxybutanoate (Intermediate D-3)

[Formula 203]

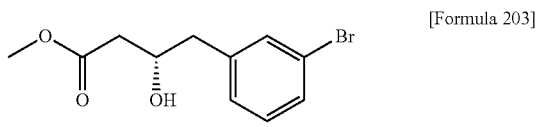

To the intermediate D-2 (2.52 kg), methanol (14.325 kg), water (0.237 kg), and [NH$_2$Me$_2$][(RuCl((S)-dm-segphos))$_2$(u-Cl)$_3$] (82.46 g, TAKASAGO) were added, the mixture was stirred at 60° C. for 6 hours under a hydrogen atmosphere, and then the solvent was evaporated under reduced pressure. Toluene (20.70 kg), and QuadraSil AP (0.60 kg, JOHNSON) were added to the residue, the mixture was stirred at 60° C. for 1 hour, then the reaction mixture was filtered, and the filtration residue was washed with toluene (2.066 kg). The solvent of the filtrate was evaporated under reduced pressure to obtain a concentrate (5.68 kg), and then, to the concentrate, n-heptane (1.22 kg) was added dropwise at 10° C. over 15 minutes, and n-heptane (1.22 kg) was further added dropwise at 5° C. over 50 minutes. The reaction mixture was stirred as it was at 5° C. for 45 minutes, and then filtered. The filtration residue was washed with a mixture of n-heptane (0.48 kg), and toluene (0.24 kg), and dried to obtain the title compound (1.923 kg).

(LCMS m/z 273.0, 275.1 (MH$^+$), retention time 1.36 minutes, LC conditions NLC-1) (Chiral LC: retention time 21.1 minutes, LC conditions Chiral LC-1)

Reference Example D-35: Methyl (S)-3-hydroxy-4-(3-(thiophen-3-ylethynyl)phenyl)butanoate (Intermediate D-35)

[Formula 204]

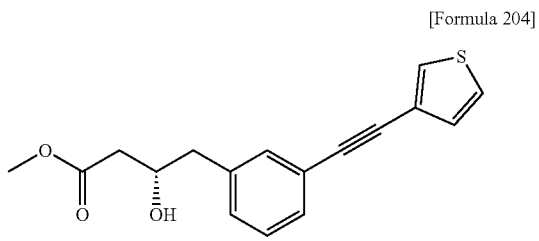 [SMILES: COC(=O)C[C@@H](O)Cc1cccc(C#Cc2ccsc2)c1]

To the intermediate D-3 (558 g), acetonitrile (1386 g), cesium carbonate (665.7 g), X-Phos (48.7 g, Nippon Kagaku), and bis(acetonitrile)palladium(II) dichloride (13.28 g, TCI) were added, and a solution of 3-ethynylthiophene (287.3 g) in acetonitrile (277.2 g) was added dropwise over 30 minutes under a nitrogen atmosphere. The reaction mixture was stirred at 40° C. for 30 minutes, and then at 60° C. for 90 minutes. The reaction mixture was cooled to room temperature, toluene (1208.3 g) and water (3488.2 g) were added to the mixture, and the resulting mixture was stirred for 20 minutes, and then filtered through Celite. The filtration residue was washed with toluene (2416.3 g), the filtrate was stirred for 10 minutes, and then left standing until it separated into an organic layer and an aqueous layer, and the aqueous layer was removed. The organic layer was washed with water (2232.3 g), and then the solvent was evaporated under reduced pressure to obtain the title compound (753.9 g).

(LCMS m/z 301.2 (MH$^+$), retention time 1.65 minutes, LC conditions NLC-1)

Reference Example D-50: Methyl (S)-3-((2-methoxyethoxy)methoxy)-4-(3-(thiophen-3-ylethynyl)phenyl)butanoate (Intermediate D-50)

[Formula 205]

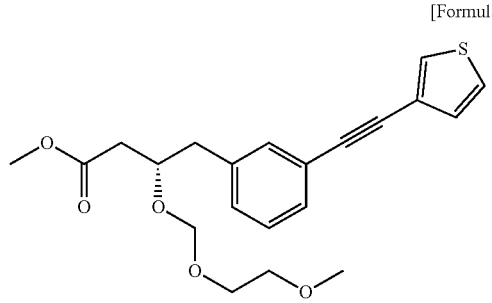

To the intermediate D-35 (753.5 g), toluene (2588.1 g), diisopropylethylamine (334.3 g), and 2-methoxyethoxymethyl chloride (322.2 g) were added under a nitrogen atmosphere, and the mixture was stirred at 80° C. for 150 minutes. The reaction mixture was cooled, water (3107.7 g) was added to the mixture, and the resulting mixture was stirred for 10 minutes, and then filtered. The filtration residue was washed with toluene (1031.6 g), the filtrate was left standing until it separated into an organic layer and an aqueous layer, and the aqueous layer was removed. The organic layer was washed with water (2071.9 g), and then the solvent was evaporated under reduced pressure to obtain an oily substance containing the intermediate D-50 (915.8 g). To this oily substance containing the intermediate D-50 (915.4 g), methanol (2310.7 g), and activated carbon Shirasagi A (292.3 g, Japan EnviroChemicals) were added, and the mixture was stirred at room temperature for 1 hour, and then filtered with filter paper. The filtration residue was washed with methanol (928.8 g), then the filtrate was filtered through a membrane filter having a pore diameter of 0.5 µm, and the filtration residue was washed with methanol (464.2 g). The filtrate was concentrated, toluene (2479.1 g), and QuadraSil MTU (349.6 g, JOHNSON) were added to the concentrate, and the mixture was stirred at 40° C. for 1 hour, and then filtered with filter paper. The filtration residue was washed with toluene (1008.0 g), then the filtrate was filtered through a membrane filter having a pore diameter of 0.5 µm, and the filtration residue was washed with toluene (503.8 g). The filtrate was concentrated under reduced pressure to obtain the title compound (710.9 g).

(LCMS m/z 406.2 (M$^+$NH$_4^+$), retention time 1.88 minutes, LC conditions NLC-1)

Reference Example D-60: (S)-3-((2-Methoxyethoxy)methoxy)-4-(3-(thiophen-3-ylethynyl)phenyl)butanal (Intermediate D-60)

[Formula 206]

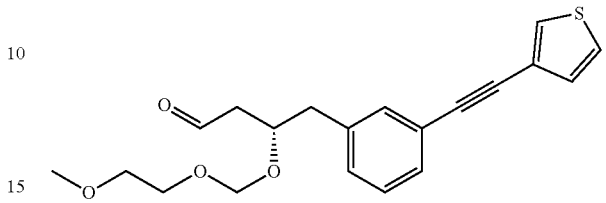

To the intermediate D-50 (355.3 g), toluene (2740.1 g) was added under a nitrogen atmosphere, and the mixture was cooled to −83° C. To this mixture, a 1 mol/L solution of diisobutylaluminum hydride in toluene (571.6 g) was added dropwise over 90 minutes. To the reaction mixture, 1 mol/L hydrochloric acid (1884.1 g) was added, the mixture was stirred at room temperature for 1 hour, toluene (64.3 g) was added to the mixture, the resulting mixture was stirred for 10 minutes, and then left standing until it separated into an organic layer and an aqueous layer, and the aqueous layer was removed. The organic layer was successively washed with 1 mol/L hydrochloric acid (1004.9 g), 1% aqueous sodium hydrogencarbonate (1997.8 g), and water (1978.1 g), and then filtered through a membrane filter having a pore diameter of 0.5 µm. The filtration residue was washed with toluene (214.3 g) to obtain a toluene solution (4061.0 g) containing the title compound (248.5 g).

(LCMS m/z 376.2 (M+NH$_4$+), retention time 1.80 minutes, LC conditions NLC-1)

Reference Example Z-70: Methyl (S)-5-(2-(4-(3-((2-methoxyethoxy)methoxy)-4-(3-(thiophen-3-ylethynyl)phenyl)butyl)-2-oxo-1,3,4-thiadiazinan-3-yl)ethyl)thiophene-2-carboxylate (Intermediate Z-70)

[Formula 207]

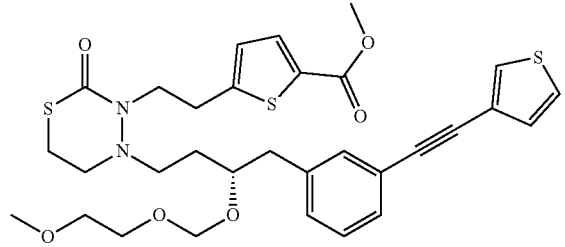

To the intermediate Z-3 (286.3 g), toluene (1959.6 g), acetic acid (474.5 g), and sodium triacetoxyborohydride (498.5 g) were added under a nitrogen atmosphere. The solvent of the solution in toluene (7927.0 g) containing the intermediate D-60 (460.28 g) was evaporated under reduced pressure to obtain a concentrated solution of the intermediate D-60 (1503.9 g), and this solution was added to the reaction mixture at room temperature over 50 minutes. Toluene (245 g) was added to the reaction mixture, and the resulting mixture was stirred for 2 hours, and then successively washed with 5% aqueous sodium hydrogencarbonate (7326.6 g), 5% aqueous sodium hydrogencarbonate (7327.2 g), and water (7071.4 g). The solvent was evaporated under reduced pressure to obtain the title compound (903.8 g).

(LCMS m/z 629.29 (MH+), retention time 2.05 minutes, LC conditions NLC-1)

Reference Example Z-17-S: Methyl (S)-5-(2-(4-(3-hydroxy-4-(3-(thiophen-3-ylethynyl)phenyl)butyl)-2-oxo-1,3,4-thiadiazinan-3-yl)ethyl)thiophene-2-carboxylate (Intermediate Z-17-S)

[Formula 208]

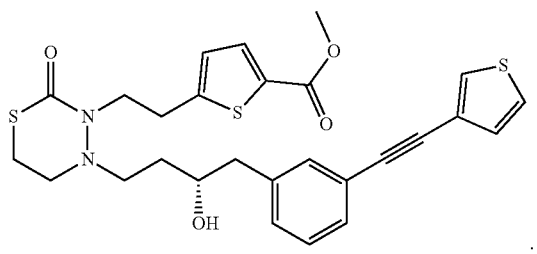

To the intermediate Z-70 (903.5 g), methanol (4293.5 g), and activated carbon Shirasagi A (90.35 g, Japan Enviro-Chemicals) were added, the reaction mixture was stirred at 40° C. for 1 hour, and then filtered, and the filtration residue was washed with methanol (715.1 g). To the filtrate, 36% hydrochloric acid (588.6 g) was added, the mixture was stirred at 40° C. for 6 hours, then toluene (2406.8 g) was added to the mixture, and the resulting mixture was cooled to room temperature. The reaction mixture was successively washed with 5% aqueous sodium hydrogencarbonate (9765.4 g), and water (1685.1 g), and then the solvent was evaporated under reduced pressure. The resulting residue was purified by column chromatography (n-heptane/ethyl acetate) to obtain the title compound (471.6 g).

(LCMS m/z 541.19 (MH+), retention time 1.87 minutes, LC conditions NLC-1)

Example 30: (S)-5-(2-(4-(3-Hydroxy-4-(3-(thiophen-3-ylethynyl)phenyl)butyl)-2-oxo-1,3,4-thiadiazinan-3-yl)ethyl)thiophene-2-carboxylic Acid

[Formula 209]

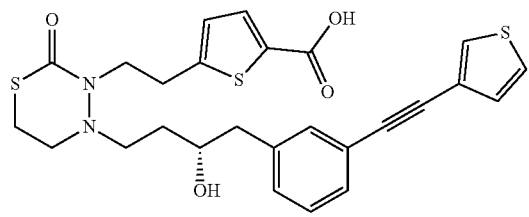

To the intermediate Z-17-S (469.5 g), THF (2393.3 g), and activated carbon Shirasagi A (94.0 g, Japan Enviro-Chemicals) were added, the reaction mixture was stirred at room temperature for 1 hour, and then filtered, and the filtration residue was washed with THF (1597.1 g). To the filtrate, THF (378.9 g), methanol (1421.8 g), and 1 mol/L aqueous sodium hydroxide (1728.2 g) were added, and the mixture was stirred for 17 hours. To the reaction mixture, toluene (2331.5 g), and water (1346.5 g) were added, the mixture was stirred, and left standing until it separated into an organic layer and an aqueous layer, and the organic layer was removed. To the aqueous layer, a mixture of toluene (2332 g), THF (1596 g), and methanol (710 g) was added, the resulting mixture was stirred, and left standing until it separated into an organic layer and an aqueous layer, and the organic layer was removed. Then, the washing with a mixture of toluene, THF, and methanol was performed 3 times in a similar manner. To the aqueous layer, toluene (4663.3 g) was added, the mixture was stirred, and left standing until it separated into an organic layer and an aqueous layer, and the organic layer was removed. To the aqueous layer, 1 mol/L hydrochloric acid was added until pH of the mixture became 7.0, then ethyl acetate (2425.9 g) was added, 1 mol/L hydrochloric acid was further added until pH of the mixture became 2.2, the mixture was stirred for 10 minutes, and then left standing until it separated into an organic layer and an aqueous layer, and the aqueous layer was removed. To the organic layer, ethyl acetate (1347.1 g), and water (897.5 g) were added, the mixture was stirred for 10 minutes, and then left standing until it separated into an organic layer and an aqueous layer, and the aqueous layer was removed. The solvent of the organic layer was evaporated under reduced pressure to obtain a residue containing the title compound (358.6 g). To this residue containing the title compound (358.3 g), methanol (1860.0 g), and activated carbon Shirasagi A (47.6 g, Japan EnviroChemicals) were added, the mixture was stirred at room temperature for 1 hour, and then filtered through a membrane filter having a pore diameter of 0.5 µm, and the filtration residue was washed with methanol (2231.2 g). To the filtrate, activated carbon Shirasagi A (188.6 g, Japan EnviroChemicals) was added, the mixture was stirred at room temperature for 1 hour, and then filtered through filter paper, and the filtration residue was washed with methanol (1490.5 g). The filtrate was filtered through a membrane filter having a pore diameter of 0.2 µm, and the filtration residue was washed with methanol (743.7 g). To the filtrate, activated carbon Shirasagi A (94.0 g, Japan EnviroChemicals) was added, the mixture was stirred at room temperature for 1 hour, and then filtered through a membrane filter having a pore diameter of 0.2 µm, and the filtration residue was washed with methanol (2231.2 g). To the filtrate, activated carbon Shirasagi A (94.1 g, Japan EnviroChemicals) was added, the mixture was stirred at room temperature for 1 hour, and then filtered through a membrane filter having a pore diameter of 0.2 µm, and the filtration residue was washed with methanol (742.9 g). The solvent of the filtrate was evaporated under reduced pressure to obtain the title compound (160.1 g).

(LCMS m/z 527.2 (MH+), retention time 1.26 minutes, LC conditions NLC-1) (Chiral LC: retention time: 21.3 minutes, LC conditions Chiral LC-2)

The compound of Example 30 is the same as the compound of Example 23.

Comparative Example 1: 4-(2-(4-(4-(3-Bromophenyl)-3-hydroxybutyl)-2-oxo-1,3,4-thiadiazinan-3-yl)ethyl)benzoic Acid

[Formula 210]

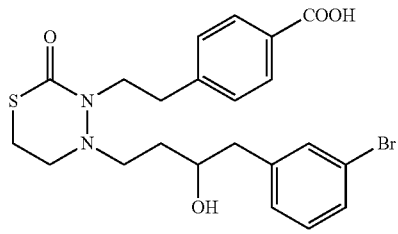

The title compound can be obtained by the preparation method described in International Patent Publication WO2006/080323 (Patent document 8), Example IAH-H072.

Preparation Example 1

Dichloromethane (20 mL) was added to poly(lactic-co-glycolic acid) (RESOMER RG504, produced by Evonik Industries, 2.0 g), which was dissolved by using an ultrasonic washing machine, and the compound of Example 23 (1.6 mg) was further added to the solution, and dissolved. This solution was added portionwise to a 0.1% aqueous solution of polyvinyl alcohol (300 mL) stirred at 3,000 rpm using a homomixer (MARK II produced by PRIMIX Corporation), and the mixture was stirred at room temperature for 10 minutes to obtain an o/w emulsion. This o/w emulsion was stirred at room temperature for 16 hours, dichloromethane was volatilized to solidify the oil phase, and the resultant was centrifuged (3,000 rpm, 20° C., 15 minutes) by using a centrifugation machine. After the supernatant was removed, the precipitates were dispersed in a 0.1% (w/v) solution of Tween 80, the dispersion was passed thorough sieves of 53 μm and 20 μm, and the sample remained on the sieve of 20 μm was centrifuged (3,000 rpm, 20° C., 15 minutes). The supernatant was removed, purified water was added to the precipitates, the mixture was centrifuged again (3,000 rpm, 20° C., 15 minutes), and the supernatant was removed. The precipitates were frozen at −80° C., and dried under reduced pressure (48 hours) to obtain drug-containing microspheres (1.2 g) having an enclosed drug ratio of 0.06%.

Preparation Example 2

Dichloromethane (20 mL) was added to poly(lactic-co-glycolic acid) (RESOMER RG504, produced by Evonik Industries, 2.0 g), which was dissolved by using an ultrasonic washing machine, and the compound of Example 23 (20 mg) was further added to the solution, and dissolved. This solution was added portionwise to a 0.1% aqueous solution of polyvinyl alcohol (300 mL) stirred at 3,000 rpm using a homomixer (MARK II produced by PRIMIX Corporation), and the mixture was stirred at room temperature for 10 minutes to obtain an o/w emulsion. This o/w emulsion was stirred at room temperature for 16 hours, dichloromethane was volatilized to solidify the oil phase, and the resultant was centrifuged (3,000 rpm, 20° C., 15 minutes) by using a centrifugation machine. After the supernatant was removed, the precipitates were dispersed in a 0.1% (w/v) solution of Tween 80, the dispersion was passed thorough sieves of 53 μm and 20 μm, and the sample remained on the sieve of 20 μm was centrifuged (3,000 rpm, 20° C., 15 minutes). The supernatant was removed, then purified water was added to the precipitates, the mixture was centrifuged again (3,000 rpm, 20° C., 15 minutes), and the supernatant was removed. The precipitates were frozen at −80° C., and dried under reduced pressure (48 hours) to obtain drug-containing microspheres (1.3 g) having an enclosed drug ratio of 0.8%.

Preparation Example 3

Dichloromethane (20 mL) was added to poly(lactic-co-glycolic acid) (RESOMER RG504, produced by Evonik Industries, 2.0 g), which was dissolved by using an ultrasonic washing machine, and the compound of Example 23 (124 mg) was further added to the solution, and dissolved. This solution was added portionwise to a 0.1% aqueous solution of polyvinyl alcohol (300 mL) stirred at 3,000 rpm using a homomixer (MARK II produced by PRIMIX Corporation), and the mixture was stirred at room temperature for 10 minutes to obtain an o/w emulsion. This o/w emulsion was stirred at room temperature for 16 hours, dichloromethane was volatilized to solidify the oil phase, and the resultant was centrifuged (3,000 rpm, 20° C., 15 minutes) by using a centrifugation machine. After the supernatant was removed, the precipitates were dispersed in a 0.1% (w/v) solution of Tween 80, the dispersion was passed thorough sieves of 53 μm and 20 μm, and the sample remained on the sieve of 20 μm was centrifuged (3,000 rpm, 20° C., 15 minutes). The supernatant was removed, then purified water was added to the precipitates, the mixture was centrifuged again (3,000 rpm, 20° C., 15 minutes), and the supernatant was removed. The precipitates were frozen at −80° C., and dried under reduced pressure (48 hours) to obtain drug-containing microspheres (1.1 g) having an enclosed drug ratio of 3.7%.

Test Example 1: Measurement of $EP_4$ Agonist Activity

In order to investigate $EP_4$ receptor agonist activity of the compounds of the present invention, production of cAMP was measured in HEK293 cells that were made to stably express the human $EP_4$ receptor.
(1) Measurement Method
By using Refseq Database, prostaglandin E receptor was searched for. As a result, gene information of human $EP_4$ (NM_000958) receptor was obtained. On the basis of this sequence information, the human $EP_4$ receptor gene was cloned by PCR in a conventional manner using human cDNA as the template, and HEK293 cells that were made to stably express the human $EP_4$ receptor were established. When cryopreserved cells of this strain were thawed and used, cells subcultured three times or more within a certain period of time (about 1 to 2 weeks) by using Dulbecco's Modified Eagle's Medium (Dulbecco's Modified Eagle's Medium may be henceforth abbreviated as DMEM) containing 10% FBS, 50 units each of penicillin and streptomycin were used. The subcultured cells were inoculated in wells of a poly-D-lysine-coated 96-well plate at a density of $2 \times 10^4$ to $2.5 \times 10^4$ cells/well, and cultured for one day. The medium in the wells was removed by suction, then DMEM (80 μL) was added to each well, and incubation was performed at 37° C. for 15 minutes. Then, 20 μL of an assay medium (DMEM containing 100 mM HEPES and 1 mM IBMX) containing $PGE_2$ or a test compound (at a concentration 5 times higher than the final concentration) was added to each well to start the reaction. The reaction was allowed at 37° C. for 30 minutes, then the medium was removed by suction, Assay/Lysis Buffer (100 μL) contained in cAMP Screen Kit (produced by Applied Biosystems) was added to terminate the reaction. Then, the reaction mixture was incubated at 37° C. for 30 minutes to prepare a sample for quantification of cAMP, and the amount of cAMP in the sample was quantified according to the method indicated in cAMP Screen Kit. By non-linear regression of the compound concentration and the amount of cAMP, the concentration of the compound required for increasing cAMP to 50% of the maximum increase ($EC_{50}$ value) was calculated by using the Kaleida Graph.

(2) Measurement Results

As shown in Table 1, the compounds of the present invention showed superior $EP_4$ agonist activity. In particular, they showed superior $EP_4$ agonist activity even compared with that of the compound of Comparative Example 1, which is a known compound similar to the compounds of the present invention.

For the compounds for which the $EP_4$ agonist activity was measured two or more times, average values are indicated, if needed. Exp. No. mentioned in the table means example number.

TABLE 1

| Exp. No. | $EC_{50}$ (nM) |
|---|---|
| 1 | 0.045 |
| 2 | 0.035 |
| 3 | 0.13 |
| 4 | 0.34 |
| 5 | 0.3 |
| 6 | 0.56 |
| 7 | 0.09 |
| 8 | 0.08 |
| 9 | 0.09 |
| 10 | 0.065 |
| 11 | 0.09 |
| 12 | 0.6 |
| 13 | 0.34 |
| 14 | 0.3 |
| 15 | 0.63 |
| 16 | 0.4 |
| 17 | 0.026 |
| 18 | 0.1 |
| 19 | 0.1 |
| 20 | 0.07 |
| 21 | 0.5 |
| 22 | 0.055 |
| 23 | 0.033 |
| 24 | 0.3 |
| 25 | 0.095 |
| 26 | 0.17 |
| 27 | 0.09 |
| 28 | 0.087 |
| 29 | 0.16 |
| Comparative Example 1 | 2.5 |

Test Example 2: Receptor Binding Test Using Human EP Receptor-Expressing Cells

In order to evaluate selectivity to each EP receptor subtype, [$^3$H]$PGE_2$ binding-inhibition activities of test compounds for cell membranes on which human $EP_2$, human $EP_3$, and human $EP_4$ receptors were stably expressed were measured.

(1) Measurement Method

As the membrane fractions of the prostaglandin E receptors $EP_2$, $EP_3$, and $EP_4$, 10.0 μg protein/tube each of HTS185M, HTS092M, and HTS142M of Merck Millipore were used, respectively. Each membrane fraction was incubated with a reaction mixture (250 μL/tube) containing a test compound and [$^3$H]$PGE_2$ at 25° C. for 60 minutes. The final concentrations of [$^3$H]$PGE_2$ were 2.56 nmol/L in the $EP_2$ measurement system, 1.54 nmol/L in the $EP_3$ measurement system, and 1.24 nmol/L in the $EP_4$ measurement system. After the reaction, the membrane fraction was collected on filter paper by using a cell harvester, the filter paper was transferred to a measurement vial, and the measurement was performed on a liquid scintillation counter.

The nonspecific binding was determined as binding observed in the presence of excess amount (10 μM) of unlabeled $PGE_2$. The measurement of the [$^3$H]$PGE_2$ binding-inhibiting activity of a test compound was performed by adding the test compound at various concentrations. The following buffers were used for the reaction.

Buffer for $EP_2$: 50 mmol/L HEPES-NaOH (pH 7.4) containing 5 mmol/L $MgCl_2$, 1 mmol/L $CaCl_2$, and 0.2% BSA Buffer for $EP_3$: 50 mmol/L Tris-HCl buffer containing 10 mmol/L $MgCl_2$, and 1 mmol/L EDTA Buffer for $EP_4$: 50 mmol/L HEPES-NaOH (pH7.4) containing 5 mmol/L $MgCl_2$, 1 mmol/L $CaCl_2$, and 0.2% BSA A dose-response curve for the [$^3$H]$PGE_2$ binding-inhibiting activity was created for each test compound, and the concentration of the test compound that inhibits 50% of the binding of $PGE_2$ and the receptor ($IC_{50}$ value) was calculated.

(2) Measurement Results

As shown in Table 2, the compounds of the present invention showed superior $EP_4$ selectivity. Exp. No. mentioned in the table means example number.

TABLE 2

| | $IC_{50}$ (nM) | | |
|---|---|---|---|
| Exp. No. | $EP_2$ | $EP_3$ | $EP_4$ |
| 23 | >1000 | >1000 | 4.35 |
| 24 | >1000 | >1000 | 43.0 |
| 25 | >1000 | >1000 | 10.9 |
| 26 | >1000 | >1000 | 16.2 |

Test Example 3: Neo-Osteogenesis Action in Rat Femur

In order to investigate osteogenesis-promoting action of the compounds of the present invention, the compounds were allowed to act on rat femurs, and the formed new bone was evaluated.

(1) Measurement Method

Eight weeks old female SD rats (Charles River Japan) were fixed in the side lying position under triple anesthesia (medetomidine hydrochloride, midazolam, and butorphanol tartrate). After hair of the left femoral region was shaved with a hair clipper, and disinfection treatment was performed with 70% ethanol, an in situ-solidified gel solution of a test compound, specifically, a test compound dissolved in poly(lactic-co-glycolic acid) (RESOMER RG502H, produced by Evonik Industries)/poly(lactic-co-glycolic acid)-polyethylene glycol block copolymer (5050 DLG mPEG 5000, produced by Lakeshore Biomaterials)/N-methyl-2-pyrroridone (produced by Wako) (weight ratio 47%/3%/50%), was filled in a 1-mL syringe, a 21 G injection needle was attached to the syringe, and the needle was transdermally stabbed from the quadriceps to the periosteum near the center of the femoral diaphyseal. Then, 100 μg as the amount of the test compound, or 50 μL as the administration volume of the solution was injected between the quadriceps and the periosteum, and the injection needle was drawn out. To the rats of the control group, the aforementioned in situ-solidified gel solution alone was administered. One week after the administration of the drug solution, the triple anesthesia was given to the animals, and they were fixed in the supine position, and euthanized by bleeding. The left femur was extracted, circumferential tissues such as muscles were removed, the bone mineral content of the whole femur was measured by using a bone mineral analyzer DCS-600EX (produced by ALOKA), then it was divided into three portions along the long axis, and the bone mineral content of the center part (diaphysis) was evaluated. The test was performed with the groups each consisting of 6 animals.

(2) Measurement Results

In the groups administered with the typical compounds of the present invention, bone mineral content of the left femur diaphysis increased compared with the control group (Tables 3 to 5). On the other hand, the bone mineral content of the diaphysis of the right femur, to which the drug solution was not administered, was not affected. On the basis of these results, it was confirmed that the compounds of the present invention are useful as a bone formation-promoting agent used by local administration. For all the compound administration groups, death of the animals was not observed, the side reactions observed for $PGE_2$ administration was not observed, either, and thus it was demonstrated that the compounds of the present invention can be safely administered.

The test results are mentioned for each test.

TABLE 3

| | Bone mineral content of femur ⅓ center region (mg) | |
|---|---|---|
| Exp. No. | Left femur (administered with compound) | Right femur (no administration of compound) |
| Control group | 69.4 ± 3.3 | 62.9 ± 2.2 |
| 3 | 80.2 ± 2.6 | 66.7 ± 2.7 |
| 6 | 81.3 ± 3.6 | 64.7 ± 2.4 |
| 8 | 98.7 ± 4.1 | 68.0 ± 1.2 |
| 13 | 82.0 ± 3.4 | 65.5 ± 2.7 |

TABLE 4

| | Bone mineral content of femur ⅓ center region (mg) | |
|---|---|---|
| Exp. No. | Left femur (administered with compound) | Right femur (no administration of compound) |
| Control group | 65.4 ± 1.9 | 61.6 ± 1.5 |
| 10 | 78.0 ± 1.5 | 61.1 ± 0.5 |
| 19 | 85.8 ± 2.3 | 59.6 ± 1.4 |
| 20 | 79.4 ± 5.2 | 58.7 ± 3.6 |
| 22 | 79.5 ± 1.9 | 60.3 ± 2.7 |

TABLE 5

| | Bone mineral content of femur ⅓ center region (mg) | |
|---|---|---|
| Exp. No. | Left femur (administered with compound) | Right femur (no administration of compound) |
| Control group | 68.0 ± 2.4 | 63.4 ± 2.1 |
| 23 | 82.7 ± 6.7 | 58.9 ± 2.9 |
| 24 | 80.7 ± 4.0 | 61.5 ± 2.3 |
| 25 | 79.1 ± 4.0 | 61.0 ± 2.1 |
| 26 | 87.0 ± 1.6 | 65.9 ± 1.2 |

Test Example 4: Neo-Osteogenesis Action in Dog Femur

In order to investigate an osteogenesis-promoting action of the compounds of the present invention, for influence of administration of microspheres containing a test compound in the vicinity of the femur of dog, osteogenesis-promoting action was evaluated by measuring new bone formed after the administration.

(1) Measurement Method

Nine to eleven months old female beagle dogs (KITAYAMA LABES) were anesthetized by administration of a 1:1 mixture of ketamine hydrochloride (Ketalar 500 mg, Daiichi Sankyo Propharma Co., Ltd.) and xylazine (Selactar 2% Injection, Bayer Yakuhin, Ltd.) at a dose of about 0.5 mL/kg, and isoflurane listed in Japanese Pharmacopoeia (Elucaine, Mylan Pharmaceutical) was used for maintenance anesthesia, which was administered with an inhaler IMPAC6 (VetEquip Inc.). After hair of the femoral region of the right hind leg was shaved, and disinfection treatment was performed, 350 µL of a microsphere suspension obtained by suspending microspheres (prepared according to the method of Preparation Example 1 or 2) containing a test compound (compound of Example 23) in a CMC solution was transdermally administered around the periosteum of the femoral diaphysis by using a 1-mL injection syringe and a 21 G injection needle. The doses of the test compound were 0.01, 0.1, 1.0, 10, and 100 µg/site, and the aforementioned microspheres were used in an amount corresponding to each dose. As a control group, a drug liquid obtained by suspending the microspheres not containing the test compound in 350 µL of the CMC solution alone was administered. Four weeks after the administration of the drug liquid, the animals were euthanized by bleeding under pentobarbital sodium (Somnopentyl) anesthesia. The femurs of both sides were extracted, immersed in a 10% neutral buffered formalin solution, and stored. The bone mineral content of the femur was measured by using Discovery X-ray bone density analyzer (produced by Toyo Medic). The test was performed with the groups each consisting of 4 dogs (2) Measurement Results Four weeks after the administration of the aforementioned microsphere suspension to the femoral diaphyses of the dogs, the bone mineral content of the femurs increased with the doses of 1.0, 10, and 100 µg as the administration amount of the test compound in a dose-dependent manner compared with the control group (Table 6). On the basis of these results, it was confirmed that the compounds of the present invention are useful as an osteogenesis-promoting agent used by local administration. For all the compound administration groups, death of the animals was not observed, the side reactions usually observed for $PGE_2$ administration was not observed, either, and thus it was demonstrated that the aforementioned microsphere preparation containing the compounds of the present invention can be safely administered.

TABLE 6

| | Bone mineral content of femur ⅓ center region (g) | |
|---|---|---|
| | Left femur (no administration of compound) | Right femur (administered with compound) |
| Control group | 2.6 ± 0.2 | 2.9 ± 0.3 |
| 0.01 μg | 2.9 ± 0.4 | 2.9 ± 0.4 |
| 0.1 μg | 2.6 ± 0.1 | 2.7 ± 0.2 |
| 1.0 μg | 3.0 ± 0.1 | 4.1 ± 0.4 |
| 10 μg | 2.8 ± 0.3 | 6.4 ± 0.7 |
| 100 μg | 2.7 ± 0.4 | 8.2 ± 1.1 |

Test Example 5: Fracture Healing-Promoting Action in Rat Femur Closed Fracture Model In order to investigate fracture healing-promoting action of the compounds of the present invention, influence of injection of microspheres containing a test compound at a fracture site of a rat femur closed fracture model was confirmed.
(1) Measurement Method
Thirteen weeks old female SD rats (Japan SLC) were fixed in the side lying position under triple anesthesia (medetomidine hydrochloride, midazolam, and butorphanol tartrate). After hair of a region from the left knee to the femoral region was shaved with a hair clipper, and disinfection treatment was performed with povidone-iodine listed in Japanese Pharmacopoeia (Isocline solution for animals, 20 mg of povidone-iodine listed in Japanese Pharmacopoeia in 1 mL, Meiji Seika Pharma), the skin of the knee part and the medial great muscle of the lateral part of the patella were excised, and the patella was shifted from the femoral head. A drill bit attached to a trephine was put on the intercondylar fossa of the exposed femoral head, and manually rotated to make a bore. A Kirschner wire (Mizuho Co., Ltd.) having a diameter of 1.2 mm preliminarily cut in a length of 31 mm was inserted into the medullary cavity of the femur through the bore. Then, the left femoral region was fixed on a three-point bending test jig of a small desktop universal testing machine (EZ Test, Shimadzu Corp.), and closed fracture of the femoral diaphyseal was caused by giving a dynamic load. Whether fracture was successfully introduced or not was confirmed by confirming generation of a complete transverse fracture in the femoral diaphyseal on an X-ray image obtained with a soft X-ray generator (M-100W, Softex) and a digital X-ray sensor (NX-04, RF Co., Ltd.). A microsphere suspension obtained by suspending microspheres (prepared according to the method of Preparation Example 3) containing a test compound (compound of Example 23) in a CMC solution was injected into the fracture part in a volume of 100 μL as the administration volume (containing 100 or 300 μg of the test compound). As the control group, a drug liquid obtained by suspending the microspheres not containing the aforementioned test compound in the CMC solution (100 μL) alone was administered. One, two, and three weeks after the generation of fracture, soft X-ray images were taken under isoflurane anesthesia, and the areas of the callus part in the X-ray images were quantified by using Image J. Four weeks after the generation of fracture, soft X-ray images were taken under triple anesthesia, the animals were fixed in the supine position, and euthanized by bleeding, and the left femurs were extracted. By confirming presence or absence of continuity of the callus under blinding in the soft X-ray images obtained 4 weeks after the generation of fracture, bone union was determined. The femur samples were cryopreserved until implementation of a bone strength test, and torsional strength was measured on the test day by using a bone strength measurement apparatus (MZ-500S, Maruto Instrument Co., Ltd.).

This test can also be performed by using dogs instead of rats.
(2) Measurement Results
In the test compound administration group, two week after the generation of fracture and thereafter, increase of fracture callus area was observed (Table 7), and the bone union rate determined on the basis of the X-ray images obtained 25 days after the generation of fracture was clearly improved (Table 8), compared with the control group. In the femurs extracted from the animals of the test compound administration group four weeks after the generation of fracture, increase of bone strength determined by the torsion test (maximum torque) was observed compared with the control group (Table 8). On the basis of these results, it was confirmed that the compounds of the present invention are useful as a bone union-promoting agent in a fracture healing process. For all the compound administration groups, death of the animals was not observed, the side reactions usually observed for $PGE_2$ administration was not observed, either, and thus it was demonstrated that the aforementioned microsphere preparation containing the compound of the present invention can be safely administered.

TABLE 7

| | Callus area (mm²) | | |
|---|---|---|---|
| | One week after fracture | Two weeks after fracture | Three weeks after fracture |
| Control group | 1.98 ± 1.52 | 22.3 ± 4.1 | 27.4 ± 4.4 |
| 100 μg | 5.24 ± 2.87 | 28.6 ± 4.7 | 35.9 ± 6.3 |
| 300 μg | 6.01 ± 2.75 | 28.9 ± 3.8 | 33.8 ± 6.8 |

TABLE 8

| | Bone union rate after 25 days (%) | Maximum torque (N · cm) |
|---|---|---|
| Control group | 61.1 | 18.8 ± 6.1 |
| 100 μg | 90.0 | 20.4 ± 7.1 |
| 300 μg | 85.7 | 26.3 ± 11.7 |

Test Example 6: Bone union-promoting action in dog lumbar vertebrae posterolateral fixation model In order to investigate a bone union-promoting action in the spinal fusion of the compounds of the present invention, influence of mixing of microspheres containing a test compound at the time of autologous bone grafting was confirmed by using a lumbar vertebrae posterolateral fixation model.
(1) Measurement Method
Twelve to thirteen months old male beagle dogs (KITAYAMA LABES) were anesthetized by administration of a 1:1 mixture of ketamine hydrochloride (Ketalar 500 mg, Daiichi Sankyo Propharma Co., Ltd.) and xylazine (Selactar 2% Injection, Bayer Yakuhin, Ltd.) at a dose of about 0.5 mL/kg, and Japanese Pharmacopoeia-listed isoflurane (Elucaine, produced by Mylan Pharmaceutical) was inhaled with an inhaler IMPAC6 (VetEquip Inc.) to maintain the anesthesia. The animal was fixed in the prone position, hair of a wide area over the right and left spina iliaca posterior superiors, part around iliac crest, and lower back was shaved, and disinfection treatment was performed with povidone-iodine listed in Japanese Pharmacopoeia (Isocline solution for animals, 20 mg of povidone-iodine listed in Japanese Pharmacopoeia in 1 mL, Meiji Seika Pharma) and ethanol for disinfection (Wako Pure Chemical Industries). The skin and soft tissue were cut and opened from the spina iliaca posterior superior along the iliac crest using a scalpel, and then the muscles covering the iliac crest were separated under the periosteum to expose the iliac crest. About 2 g each of the right and left iliums were extracted by using a rongeur and bone scissors, and astriction was performed. The collected ilium, from which the soft tissues were removed, was finely broken with bone scissors, and thereby made into chips of 1 mm size to obtain 2 g each of bone grafts for right and left. Then, the skin was dissected along the spinous processes of lower back with a scalpel, the left and right lumbodorsal fascias were dissected, and then the transverse processes of the fourth and fifth lumbar vertebrae were exposed while the multifidus muscle and longissimus muscle were separated and dissected between the fascias thereof. The soft tissues adhering to the transverse processes were removed, and then decortication of the cortical bone on the surface of the transverse processes was performed with an electric drill (OS-40MV2, Osada Electric Co., Ltd.) to prepare a bone graft bed. The bone graft (2 g) prepared above was sufficiently mixed with a microsphere suspension obtained by suspending microspheres containing a test compound (compound of Example 23) in an amount corresponding to 10, 30, or 100 μg of the test compound (prepared according to the method of Preparation Example 1) in 800 μL of a CMC solution, embedded and grafted on the transverse processes of the fourth and fifth lumbar vertebrae, and the bone graft bed between the transverse processes. After the autologous bone grafting, the lumbodorsal fascia, subcutaneous tissues, and skin were sutured, and the surgical site was disinfected. Twelve weeks after the operation, the animals were euthanized with overdose (30 mg/kg) of sodium pentobarbiturate (Somnopentyl, Kyoritsuseiyaku Corporation), and then the lumbar vertebrae were extracted. Bone union was judged by manually confirming movability of the fourth and fifth lumbar vertebrae (manual palpation) under blinding, and soft X-ray images were obtained from one direction by using Softex M-60 (Softex). Each soft X-ray image was evaluated by one person under blinding in accordance with the evaluation criteria shown in Table 9. The test was performed with the groups each consisting of 5 animals.

TABLE 9

| Grade | Evaluation criteria |
| --- | --- |
| 3 | Osteogenesis advanced at the grafting site, and the graft mass crosslinked the transverse processes, and fused to the transverse processes, vertebral arch, or centrum with uniform continuity. |

TABLE 9-continued

| Grade | Evaluation criteria |
| --- | --- |
| 2 | Osteogenesis advanced at the grafting site, and the graft mass crosslinked the transverse processes, and fused to the transverse processes, vertebral arch, or centrum, but they did not constitute one mass, and continuity between transverse processes was only partial, or gaps or radiolucent lines were observed in a part of the graft mass. |
| 1 | Advance of osteogenesis was observed mainly around transverse processes, but the graft mass between the transverse processes did not have continuity, and definite gaps or radiolucent lines interrupting the graft mass were observed. |
| 0 | Osteogenesis was not observed, and the graft material did not change, or was absorbed and disappeared. |

(2) Measurement results

When lumbar vertebra samples were extracted, and osteogenesis was evaluated on the basis of degree of calcification using soft X-ray images, in the control group where the microspheres not containing the test compound was mixed in the autologous graft ilium, movability was observed between the 4th and 5th lumbar vertebrae, but calcification between transverse processes was not observed in the soft X-ray images in all the five examples. On the other hand, in the group where the microspheres containing the test compound was administered, at each of the doses of 10, 30, or 100 μg, it was judged that movability was observed between the 4th and 5th lumbar vertebrae in one example out of five examples, but no movability was observed in the four other examples. In the soft X-ray images, promotion of osteogenes and osseous continuity were observed between the 4th and 5th lumbar vertebra transverse processes, namely, the continuity score was 2 or higher, at all the doses. In addition, the score increased in a dose-dependent manner (Table 10, 2.4±0.5, 2.6±0.5, and 2.8±0.4, respectively).

On the basis of these results, it was confirmed that the compounds of the present invention are useful as an agent for promoting bone union in the spinal fusion surgery based on autologous bone grafting. For all the compound administration groups, death of the animals was not observed, the side reactions usually observed for $PGE_2$ administration was not observed, either, and thus it was demonstrated that the aforementioned microspheres containing the compound of the present invention can be safely administered in the spinal fusion surgery.

TABLE 10

| | Control group | 10 μg/site | 30 μg/site | 100 μg/site |
| --- | --- | --- | --- | --- |
| Manual evaluation of bone union | 0/5 | 4/5 | 4/5 | 4/5 |
| Continuity score based on soft X-ray image (Mean ± SD) | 0 ± 0 | 2.4 ± 0.5 | 2.6 ± 0.5 | 2.8 ± 0.4 |

What is claimed is:

1. The compound mentioned below, or a salt thereof;

[Formula 13]

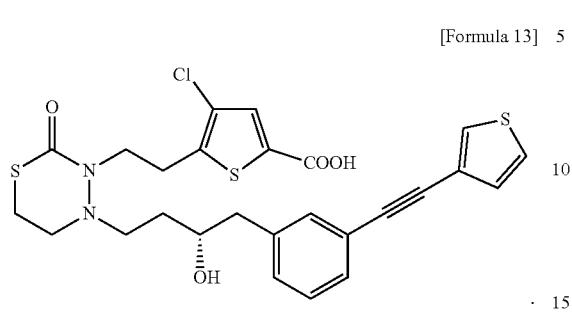

2. The compound mentioned below, or a salt thereof;

[Formula 14]

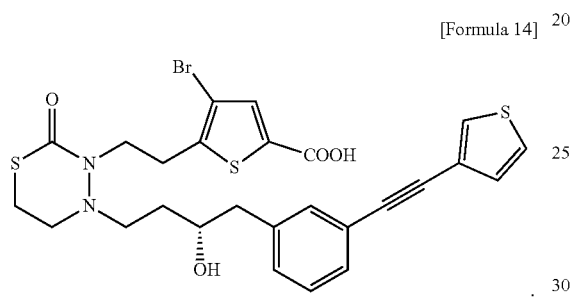

3. The compound mentioned below, or a salt thereof;

[Formula 15]

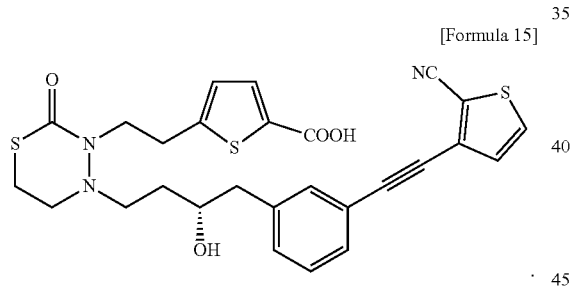

4. The compound mentioned below, or a salt thereof;

[Formula 16]

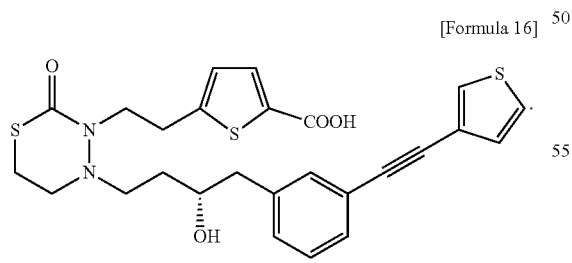

5. The compound mentioned below, or a salt thereof;

[Formula 17]

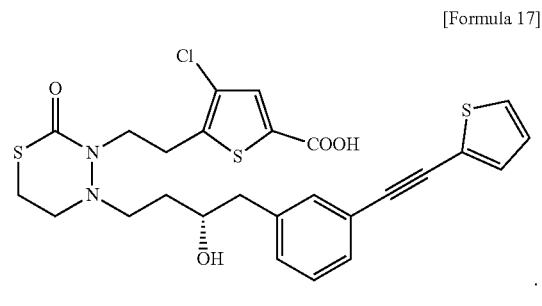 [SMILES: O=C(O)c1cc(Cl)c(CCN2C(=O)SCCN2CC[C@@H](O)Cc2cccc(C#Cc3cccs3)c2)s1]

6. The compound mentioned below, or a salt thereof;

[Formula 18]

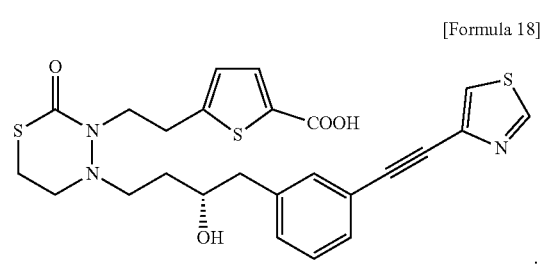 [SMILES: O=C(O)c1ccc(CCN2C(=O)SCCN2CC[C@@H](O)Cc2cccc(C#Cc3cscn3)c2)s1]

7. The compound mentioned below, or a salt thereof;

[Formula 19]

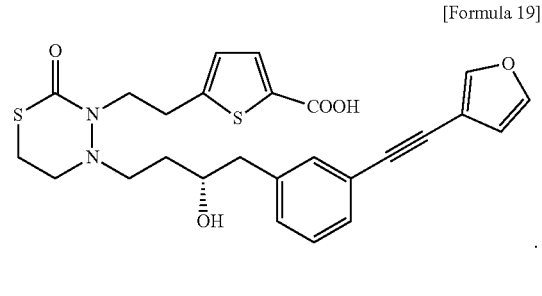 [SMILES: O=C(O)c1ccc(CCN2C(=O)SCCN2CC[C@@H](O)Cc2cccc(C#Cc3ccoc3)c2)s1]

8. A pharmaceutical composition containing the compound according to any one of claims 1 to 7 or a pharmaceutically acceptable salt thereof as an active ingredient, and a pharmaceutically acceptable carrier.

9. A method for therapeutic treatment and/or promotion of healing of fracture, which comprises administering to a patient in need thereof a pharmaceutical composition according to claim 8.

10. A method for promotion of bone union in spinal fusion surgeries, which comprises administering to a patient in need thereof a pharmaceutical composition according to claim 8.

* * * * *